(12) United States Patent
Tagaya et al.

(10) Patent No.: US 10,808,009 B2
(45) Date of Patent: Oct. 20, 2020

(54) PEPTIDE CONJUGATES

(71) Applicant: BIONIZ, LLC, Irvine, CA (US)

(72) Inventors: Yutaka Tagaya, Rockville, MD (US); Nazli Azimi, San Juan Capistrano, CA (US)

(73) Assignee: BIONIZ, LLC, Irvine, CA (US)

( * ) Notice: Subject to any disclaimer, the term of this patent is extended or adjusted under 35 U.S.C. 154(b) by 0 days.

(21) Appl. No.: 15/957,806

(22) Filed: Apr. 19, 2018

(65) Prior Publication Data

US 2018/0237475 A1 Aug. 23, 2018

Related U.S. Application Data

(63) Continuation of application No. 15/179,900, filed on Jun. 10, 2016, now Pat. No. 9,951,105, which is a continuation-in-part of application No. 14/522,240, filed on Sep. 11, 2015, now Pat. No. 9,675,672, which is a continuation of application No. 13/868,725, filed on Apr. 23, 2013, now Pat. No. 9,133,243, which is a continuation of application No. 13/589,017, filed on Aug. 17, 2012, now Pat. No. 8,455,449, which is a continuation of application No. PCT/US2012/021566, filed on Jan. 17, 2012, said application No. 14/852,240 is a continuation of application No. 13/980,305, filed as application No. PCT/US2012/021566 on Jan. 17, 2012, now Pat. No. 9,133,244, said application No. 15/179,900 is a continuation-in-part of application No. PCT/US2014/069597, filed on Dec. 10, 2014.

(60) Provisional application No. 61/527,049, filed on Aug. 24, 2011, provisional application No. 61/433,890, filed on Jan. 18, 2011, provisional application No. 61/914,063, filed on Dec. 10, 2013.

(51) Int. Cl.

| A61K 38/00 | (2006.01) |
|---|---|
| A61K 38/10 | (2006.01) |
| A61K 38/20 | (2006.01) |
| A61K 47/64 | (2017.01) |
| A61K 8/64 | (2006.01) |
| C07K 7/08 | (2006.01) |
| C07K 7/06 | (2006.01) |
| C07K 14/54 | (2006.01) |
| A61Q 19/00 | (2006.01) |
| A61Q 19/08 | (2006.01) |
| A61Q 3/00 | (2006.01) |
| A61Q 7/00 | (2006.01) |
| C07K 14/52 | (2006.01) |

(52) U.S. Cl.
CPC ............ *C07K 7/08* (2013.01); *A61K 8/64* (2013.01); *A61K 38/20* (2013.01); *A61K 47/642* (2017.08); *A61K 47/643* (2017.08); *A61Q 3/00* (2013.01); *A61Q 7/00* (2013.01); *A61Q 19/00* (2013.01); *A61Q 19/004* (2013.01); *A61Q 19/08* (2013.01); *C07K 7/06* (2013.01); *C07K 14/52* (2013.01); *C07K 14/54* (2013.01); *A61K 38/00* (2013.01); *A61K 38/10* (2013.01)

(58) Field of Classification Search
CPC ........ A61K 38/00; A61K 38/10; A61K 38/20; A61K 47/642; A61K 47/643; A61K 8/64; A61Q 19/00; A61Q 19/004; A61Q 19/08; A61Q 3/00; A61Q 7/00; C07K 7/00; C07K 14/52; C07K 14/54; C07K 7/06; C07K 7/08
USPC ........................................ 530/300; 514/1.1
See application file for complete search history.

(56) References Cited

U.S. PATENT DOCUMENTS

| 4,518,584 A | 5/1985 | Mark et al. |
|---|---|---|
| 5,700,913 A | 12/1997 | Taniguchi et al. |
| 5,795,966 A | 8/1998 | Grabstein et al. |
| 6,013,480 A | 1/2000 | Grabstein et al. |
| 6,028,186 A | 2/2000 | Tasset et al. |
| 6,127,387 A | 10/2000 | Huang et al. |
| 6,168,783 B1 | 1/2001 | Grabstein et al. |
| 6,261,559 B1 | 7/2001 | Levitt et al. |
| 6,307,024 B1 | 10/2001 | Novak et al. |
| 6,323,027 B1 | 11/2001 | Burkly et al. |

(Continued)

FOREIGN PATENT DOCUMENTS

| AU | 2017200489 A1 | 2/2017 |
|---|---|---|
| CN | 1478098 | 2/2004 |

(Continued)

OTHER PUBLICATIONS

Yannpolsky et al, "The Exchangeability of Amino Acids in Proteins," Genetics, 2005, 170: 1459-1472.*

(Continued)

*Primary Examiner* — Julie Ha
(74) *Attorney, Agent, or Firm* — Knobbe, Martens, Olson & Bear, LLP

(57) ABSTRACT

Methods and compositions related to the selective, specific disruption of multiple ligand-receptor signaling interactions, such as ligand-receptor interactions implicated in disease, are disclosed. These interactions may involve multiple cytokines in a single receptor family or multiple ligand receptor interactions from at least two distinct ligand-receptor families. The compositions may comprise polypeptides having composite sequences that comprise sequence fragments of two or more ligand binding sites. The methods and compositions may involve sequence fragments of two or more ligand binding sites that are arranged to conserve the secondary structure of each of the ligands from which the sequence fragments were taken.

12 Claims, 28 Drawing Sheets

Specification includes a Sequence Listing.

(56) References Cited

U.S. PATENT DOCUMENTS

| | | |
|---|---|---|
| 6,686,178 B2 | 2/2004 | Novak et al. |
| 6,770,745 B2 | 8/2004 | Burkly et al. |
| 6,793,919 B2 | 9/2004 | Mohler |
| 6,797,263 B2 | 9/2004 | Strom et al. |
| 6,811,780 B2 | 11/2004 | Furfine et al. |
| 6,838,433 B2 | 1/2005 | Serlupi-Crescenzi |
| 6,955,807 B1 | 11/2005 | Shanafelt et al. |
| 7,105,653 B2 | 9/2006 | Shanafelt et al. |
| 7,148,333 B2 | 12/2006 | Cox, III |
| 7,192,578 B2 | 3/2007 | Levitt et al. |
| 7,235,240 B2 | 6/2007 | Grabstein et al. |
| 7,314,623 B2 | 1/2008 | Grusby et al. |
| 7,347,995 B2 | 3/2008 | Strom et al. |
| 7,423,123 B2 | 9/2008 | Boisvert et al. |
| 7,473,765 B2 | 1/2009 | Novak et al. |
| 7,632,814 B2 | 12/2009 | Hazlehurst |
| 7,700,088 B2 | 4/2010 | Levitt et al. |
| 7,731,946 B2 | 6/2010 | Grusby et al. |
| 7,785,580 B2 | 8/2010 | Pan et al. |
| 7,786,072 B2 | 8/2010 | Verdine et al. |
| 7,645,449 B2 | 12/2010 | Stassi et al. |
| 7,910,123 B2 | 3/2011 | McKay |
| 7,959,908 B2 | 6/2011 | Nelson et al. |
| 8,110,180 B2 | 2/2012 | Novak et al. |
| 8,211,420 B2 | 7/2012 | Bondensgaard |
| 8,455,449 B2 | 6/2013 | Tagaya |
| 8,512,946 B2 * | 8/2013 | Mirkin ............... G01N 33/5434 435/283.1 |
| 9,133,243 B2 | 9/2015 | Tagaya |
| 9,133,244 B2 | 9/2015 | Tagaya |
| 9,675,672 B2 | 6/2017 | Stevanov |
| 9,951,105 B2 | 4/2018 | Tagaya |
| 9,959,384 B2 | 5/2018 | Azimi et al. |
| 10,030,058 B2 | 7/2018 | Azimi |
| 10,030,059 B2 | 7/2018 | Azimi |
| 10,227,382 B2 | 3/2019 | Tagaya |
| 2002/0114781 A1 | 8/2002 | Strom et al. |
| 2003/0049798 A1 | 3/2003 | Carter et al. |
| 2003/0108549 A1 | 6/2003 | Carter et al. |
| 2004/0009150 A1 | 1/2004 | Nelson et al. |
| 2004/0136954 A1 | 7/2004 | Grusby et al. |
| 2005/0124044 A1 | 6/2005 | Cunningham et al. |
| 2006/0034892 A1 | 2/2006 | Ueno |
| 2006/0039902 A1 | 2/2006 | Young et al. |
| 2006/0236411 A1 | 10/2006 | Dreher et al. |
| 2006/0263857 A1 | 11/2006 | Lefrancois et al. |
| 2007/0048266 A1 | 3/2007 | Nelson |
| 2008/0038275 A1 | 2/2008 | Martin |
| 2008/0108552 A1 | 5/2008 | Hazelhurst |
| 2008/0166338 A1 | 7/2008 | Leonard |
| 2009/0136511 A1 | 5/2009 | Santos Savio et al. |
| 2009/0148403 A1 | 6/2009 | Bosivert et al. |
| 2009/0253864 A1 | 10/2009 | Peschke et al. |
| 2009/0258357 A1 | 10/2009 | Ruebn |
| 2010/0099742 A1 | 4/2010 | Stassi |
| 2010/0135958 A1 | 6/2010 | Hwu |
| 2010/0196309 A1 | 8/2010 | Bondensgaard et al. |
| 2010/0266531 A1 | 10/2010 | Hsieh |
| 2011/0081327 A1 | 4/2011 | Nicolette |
| 2011/0091515 A1 * | 4/2011 | Zilberman ............... A61L 15/44 424/409 |
| 2011/0142833 A1 | 6/2011 | Young |
| 2011/0245090 A1 | 10/2011 | Abbas |
| 2011/0311475 A1 | 12/2011 | Borte |
| 2012/0329728 A1 | 12/2012 | Tagaya |
| 2013/0052127 A1 * | 2/2013 | Sasaki ................... A61K 31/711 424/1.29 |
| 2013/0095102 A1 | 4/2013 | Levin |
| 2013/0217858 A1 | 8/2013 | Tagaya et al. |
| 2016/0000877 A1 | 1/2016 | Tagaya et al. |
| 2016/0306918 A1 | 10/2016 | Azimi |
| 2017/0051015 A1 | 2/2017 | Tagaya et al. |
| 2017/0101452 A1 | 4/2017 | Azimi |
| 2017/0204153 A1 | 7/2017 | Tagaya |
| 2017/0240607 A1 | 8/2017 | Azimi |
| 2019/0070263 A1 | 3/2019 | Azimi |
| 2019/0194255 A1 | 6/2019 | Tagaya |

FOREIGN PATENT DOCUMENTS

| | | |
|---|---|---|
| CN | 1703423 | 11/2005 |
| CN | 103501805 A | 1/2014 |
| CN | 103501805 B | 9/2018 |
| EP | 1525213 | 4/2005 |
| EP | 2665486 A1 | 11/2013 |
| EP | 3359556 A1 | 8/2018 |
| JP | 2004-525076 | 8/2004 |
| JP | 2005-508179 | 3/2005 |
| JP | 2017222635 A | 12/2017 |
| JP | 6395379 B2 | 9/2018 |
| WO | WO 8702990 A1 | 5/1987 |
| WO | WO 00/72864 A1 | 12/2000 |
| WO | WO 2003040313 A1 | 5/2003 |
| WO | WO 03087320 | 10/2003 |
| WO | WO 2004084835 A2 | 10/2004 |
| WO | WO 2005014642 A2 | 2/2005 |
| WO | WO 2005030196 A2 | 4/2005 |
| WO | WO 2005067956 A2 | 7/2005 |
| WO | WO 2005105830 A1 | 11/2005 |
| WO | WO 2005112983 A2 | 12/2005 |
| WO | WO 2006105538 A2 | 5/2006 |
| WO | WO 2006111524 A2 | 10/2006 |
| WO | WO 2006113331 A1 | 10/2006 |
| WO | WO 2008049920 A2 | 2/2008 |
| WO | WO 2009100035 A2 | 8/2009 |
| WO | WO 2009108341 A1 | 9/2009 |
| WO | WO 2009132821 A1 | 11/2009 |
| WO | WO 2010039533 A2 | 4/2010 |
| WO | WO 2010076339 A1 | 7/2010 |
| WO | WO 2010103031 A1 | 9/2010 |
| WO | WO 2010133828 A1 | 11/2010 |
| WO | WO 2011070214 A2 | 6/2011 |
| WO | WO 2011133948 A2 | 10/2011 |
| WO | WO 2012006585 A2 | 1/2012 |
| WO | WO 2012012531 A2 | 1/2012 |
| WO | WO 2012/099886 | 7/2012 |
| WO | WO 2012/175222 A1 | 12/2012 |
| WO | WO 2015/089217 A2 | 6/2015 |
| WO | WO 2015/089217 A3 | 6/2015 |
| WO | WO 2017/062685 A1 | 4/2017 |
| WO | WO 2017062865 A8 | 6/2018 |
| WO | WO 2018/187499 A1 | 10/2018 |

OTHER PUBLICATIONS

Antony, et al., "Interleukin-2-Dependent Mechanisms of Tolerance and Immunity In Vivo," J. Immunol. 176: 5255-5266, 2006.
Azimi, N., "Human T Cell Lymphotropic Virus Type I Tax Protein Trans-Activates Interleukin 15 Gene Transcription Through an NF-kappaB Site," Proc. Natl. Acad. Sci. USA 95:2452-2457, 1998.
Azimi, N., "Involvement of IL-15 In The Pathogenesis of Human T Lymphotropic Virus Type-I-Associated Myelopathy/Tropical Spastic Paraparesis: Implications for Therapy with a Monoclonal Antibody Directed to the IL-2/15Rbeta Receptor," J. Immunol. 163:4064-4072, 1999.
Azimi, N., et al., "How Does Interleukin 15 Contribute to the Pathogenesis of HTLV Type-1 Associated Myelopathy/Tropical Spastic Paraparesis?" AIDS Res. Hum. Retroviruses 16:1717-1722, 2000.
Azimi, N., et al., "IL-15 Plays a Major Role in the Persistence of Tax-specific CD8 Cells in HAM/TSP patients," Proc. Natl. Acad. Sci. 98:14559-14564, 2001.
Bazan, J.F., "Hematopoietic Receptors and Helical cytokines," Immunol. Today 11:350-354, 1990.
Bernard et al., dentification of an Interleukin-15α Receptor-binding Site on Human Interleukin-15*, The Journal of Biological Chemistry (2004)279:24313-24322.
Bettini, M., and D.A. Vignali, "Regulatory T Cells and Inhibitory Cytokines in Autoimmunity," Curr. Opin. Immunol. 21:612-618, 2009.

(56) References Cited

OTHER PUBLICATIONS

Bodd, M., et al., "HLA-DQ2-Restricted Gluten-Reactive T cells Produce IL-21 but not IL-17 or IL-22," Mucosal Immunol. 3:594-601, 2010.
Bonsch, et al Species-specific Agonist/Antagonist Activities of Human Interleukin-4 Variants Suggest Distinct Ligand Binding Properties of Human and Murine Common Receptor γ Chain*, The Journal of Biological Chemistry (1995) 270:8452-8457.
DE Rezende, L.C., et al., "Regulatory T Cells as a Target for Cancer Therapy," Arch. Immunol. Ther. Exp. 58:179-190, 2010.
Decision of Rexamination Received Jun. 27, 2017 in Chinese Application 201280010348.8.
Definition of composite from www.merriam-sebster.com/dictionary/composite, pp. 1-5. Accessed Feb. 17, 2015.
Definition of derivative from http://cancerweb.ncl.ac.uk/omd/about.html, pp. 1-5. Accessed Jul. 7, 2005.
Dubois, S., et al., "IL-15R alpha Recycles and Presents IL-15 in Trans to Neighboring Cells," Immunity 17:537-547, 2002.
Extended EP Search report dated May 22, 2014 for PCT/US2012/021566.
Fehniger, T.A., "Fatal Leukemia in Interleukin 15 Transgenic Mice Follows Early Expansions in Natural Killer and Memory Phenotype CD8+ T Cells," J. Exp. Med. 193:219-231, 2001.
Final Office Action dated Feb. 24, 2015 for U.S. Appl. No. 13/868,725.
Final Office Action dated Nov. 29, 2016 for JP Patent Application 2013-550541.
Fisher, A.G. et al., "Lymphoproliferative disorders in an IL-7 transgenic mouse line," Leukemia 2, 1993, pp. 66-68.
Gong, J.H. et al., Characterization of a human cell line (NK-92) with phenotypical and functional characteristics of activated natural killer cells. Leukemia 8, 1994, pp. 652-658.
Hennighausen, L., and G.W. Robinson, "Interpretation of Cytokine Signaling Through the Transcription Factors STAT5A and STAT5B," Genes Dev. 22:711-721, 2008.
Hines, L et at. Interleukin 15, partial [synthetic construct]. NCBI PDS Accession No. AAX36174, interleukin 15, partial [synthetic construct]. Submitted Jan. 5, 2005; downloaded from the internet <https://www.ncbi.nlm.nih.gov/protein/60811495/> on Dec. 14, 2016, p. 1.
Hodge, D.L., et al., IL-2 and IL-12 Alter NK Cell Responsiveness to IFN-Gamma-Inducible Protein 10 by Down-Regulating CXCR3 Expression, J. Immun. 168:6090-6098, 2002.
International Preliminary Report on Patentability dated Jul. 23, 2013 for PCT/US2012/021566.
International Preliminary Report on Patentability issued Jun. 14, 2016 for PCT/US2012/062870.
International Search Report and Written Opinion dated Jan. 17, 2017 for PCT/US2016/055845.
International Search Report and Written Opinion of the International Searching Authority in International Application No. PCT/US2012/021566 dated May 10, 2012.
International Search Report dated Jun. 26, 2015 for PCT/US14/69597.
Klingemann, H.G. et al., "A cytotoxic NK-cell line (NK-92) for ex vivo purging of leukemia from blood," Blood Marrow Transplant 2, 1996, pp. 68-75.
Krause, C.D. and S. Pestka, "Evolution of the Class 2 Cytokines and Receptors, and Discovery of New Friends and Relatives," Pharmacol. and Therapeutics 106:299-346, 2005.
Kundig, T.M. et al. "Immune Responses of the interleukin-2-deficient mice," Science 262, 1993, pp. 1059-1061.
Le Buanec, H., et al., "Control of Allergic Reactions in Mice by an Active Anti-Murine IL-4 Immunization," Vaccine 25:7206-7216, 2007.
Littman, D.R., and A.Y. Rudensky, "Th17 and Regulatory T Cells in Mediating and Restraining Inflammation," Cell 140(6):845-858, 2010.
Miyagawa, F., et al., "IL-15 Serves as a Costimulator in Determining the Activity of Autoreactive CD8 T Cells in an Experimental Mouse Model of Graft-Versus-Host-Like Disease," J. Immunol. 181:1109-1119, 2008.
NCBI Accession No. ABF82250, Accessed Aug. 11, 2014.
NCBI Accession No. BAA96385, Accessed Aug. 11, 2014.
NCBI Accession No. NP_999580, Accessed Aug. 11, 2014.
NCBI Accession No. ACT78884, Accessed Aug. 11, 2014.
NCBI Accession No. NP_999288, Accessed Aug. 11, 2014.
Noguchi, M., et al., "Interleukin 2 Receptor Gamma Chain Mutation Results in X-linked Severe Combined Immunodeficiency in Humans," Cell 73:147-157, 1993.
Notice of Acceptance dated October 19, 2016 for AU Application 2012207456.
Notice of Allowance dated Feb. 19, 2013 for U.S. Appl. No. 13/589,017.
Notice of Allowance dated Feb. 6, 2017 for U.S. Appl. No. 14/852,240.
Notice of Allowance dated May 11, 2015 for U.S. Appl. No. 13/868,725.
Notice of Allowance dated May 4, 2015 for U.S. Appl. No. 13/980,305.
Notification of Re-examination issued Mar. 24, 2017 for CN Patent Application 201280010348.8.
O'Shea, J.J., "Targeting the Jak/STAT Pathway for Immunosuppression," Ann. Rheum. Dis. 63:(Suppl. II):ii67-71, 2004.
Office Action dated Aug. 18, 2014 for U.S. Appl. No. 13/868,725.
Office Action dated Aug. 3, 2017for U.S. Appl. No. 15/103,804.
Office Action dated Aug. 8, 2017for U.S. Appl. No. 15/585,666.
Office Action dated Jan. 26, 2016 for JP Patent Application 2013-550541.
Office Action dated Jul. 2, 2014 for corresponding CN Application 201280010348.8.
Office Action dated Jul. 4, 2016 for Chinese Patent Application No. 201280010348.8.
Office Action dated Nov. 12, 2014 for U.S. Appl. No. 13/980,305.
Office Action dated Oct. 26, 2016 in EP Patent Application No. 12736203.6.
Office Action dated Oct. 18, 2014 for U.S. Appl. No. 13/868,725.
Office Action dated Oct. 22, 2015 for AU Application 2012207456.
Office Action dated Oct. 27, 2015 for Chinese Patent Application No. 201280010348.8.
Office Action dated Sep. 6, 2016 for U.S. Appl. No. 14/852,240.
Office Action dated Apr. 28, 2015 for Chinese Patent Application No. 201280010348.8.
Office Action dated Oct. 23, 2017 in U.S. Appl. No. 15/287,517.
Oh, U., and S. Jacobson, "Treatment of HTLV-I-Associated Myelopathy / Tropical Spastic Paraparesis: Towards Rational Targeted Therapy," Neurol. Clin. 26:781-785, 2008.
Orzaez, M., et al., "Peptides and Peptide Mimics as Modulators of Apoptotic Pathways," Chem. Med. Chem. 4:146-160, 2009.
Paul, W.E., "Pleiotropy and Redundancy: T Cell-Derived Lymphokines in the Immune Response," Cell 57:521-524, 1989.
Pesu, M., "Jak3, Severe Combined Immunodeficiency, and a New Class of Immunosuppressive Drugs," Immunol. Rev. 203:127-142, 2005.
Pesu, M., Laurence, et al., "Therapeutic Targeting of Janus Kinases," Immunol. Rev. 223:132-142, 2008.
Restriction Requirement dated Feb. 28, 2017 for U.S. Appl. No. 15/179,900.
Restriction Requirement dated Jul. 25, 2017 in U.S. Appl. No. 15/287,517.
Restriction Requirement dated Jun. 24, 2014 for U.S. Appl. No. 13/980,305.
Restriction Requirement dated Mar. 24, 2017 for U.S. Appl. No. 15/103,804.
Restriction Requirement dated May 9, 2014 for U.S. Appl. No. 13/868,725.
Rochman, Y., et al., "New Insights into the Regulation of T Cells by Gamma C Family Cytokines," Nat. Rev. Immunol. 9:480-490, 2009.
Sakaguchi, S., et al., "Regulatory T Cells and Immune Tolerance," Cell 133:775-787, 2008.

(56) References Cited

OTHER PUBLICATIONS

Sato, N., et al., "Development of an IL-15-Autocrine CD8 T-cell Leukemia in IL-15 Transgenic mice requires the cis-expression of IL-15R apha," Blood 2011.
Sugamura, K., et al., "The Common Gamma-Chain for Multiple Cytokine Receptors," Adv. Immunol. 59:225-277, 1995.
Sugamura, K., et al., "The Interleukin-2 Receptor Gamma Chain: Its Role in the Multiple Cytokine Receptor Complexes and T Cell Development in XSCID," Annu. Rev. Immunol. 14:179-205, 1996.
Supplementary European Search Report dated May 22, 2014 for European Application No. 12784848.9.
Tagaya, Y., "Memory CD8 T Cells Now Join 'Club 21,'" J. Leuk. Biol. 87:13-15, 2010.
Tagaya, Y., et al., "Identification of a Novel Receptor/Signal Transduction Pathway for IL-15/T in Mast Cells," EMBO J. 15:4928-4939, 1996.
Takai, K. et al., The Wheat-Germ Cell-Free Expression System, Curr. Pharm. Biotechnol. 11, 2010, pp. 272-278.
Takeshita, T., et al., "Cloning of the Gamma Chain of the Human IL-2 Receptor," Science 257:379-382, 1992.
Tanaka, T., et al., "A Novel Monoclonal Antibody Against Murine IL-2 Receptor Beta-Chain. Characterization of Receptor Expression in Normal Lymphoid Cells and EL-4 Cells," J. Immunol. 147:2222-2228, 1991.
Waldmann, T.A., Anti-Tac (daclizumab, Zenapax) in the Treatment of Leukemia, Autoimmune Diseases, and in the Prevention of Allograft Rejection: A 25-Year Personal Odyssey, J. Clin. Immunol. 27:1-18, 2007.
Water is naturally occurring from www.biology-online.org/dictionary/Water, pp. 1-3, Accesssed Apr. 24, 2014.
Examination Report dated Nov. 14, 2018 in Australian Patent Application No. 2016334085.
Extended European Search Report dated Mar. 28, 2019 in European Patent Application No. 16854367.6.
Final Office Action dated Dec. 13, 2017 for U.S. Appl. No. 15/585,666.
International Preliminary Report on Patentability issued Apr. 10, 2018 for PCT/US2016/055845.
International Search Report and Written Opinion dated Aug. 23, 2018 for PCT/US2018/026125.
Notice of Allowance dated Dec. 15, 2017 in U.S. Appl. No. 15/179,900.
Notice of Allowance dated Dec. 19, 2017 for U.S. Appl. No. 15/103,804.
Notification of Allowance dated May 31, 2018 for CN Patent Application 201280010348.8.
Notice of Allowance dated Mar. 26, 2018 in U.S. Appl. No. 15/287,517.
Notice of Allowance dated Mar. 26, 2018 in U.S. Appl. No. 15/585,666.
Notice of Allowance dated Oct. 22, 2018 for U.S. Appl. No. 15/474,312.
Olosz, F. et al. Structural Baisis for Binding Multiple Ligands by the Common Cytokine Receptor [gamma] -chain, Journal of Biological Chemistry, vol. 277, No. 14, pp. 12047-12052, (2002).
Office Action dated Jul. 24, 2017 in U.S. Appl. No. 15/179,900.
Office Action dated Oct. 4, 2017 in European Patent Application No. 12736203.6.
Office Action dated Nov. 22, 2017 in Canadian Application No. 2,824,51.
Office Action dated Feb. 9, 2018 in Australian Application No. 2017200489.
Office Action dated Feb. 20, 2018 for JP Patent Application 2013-550541.
Office Action dated May 8, 2018 in JP Patent Application No. 2017-90501.
Office Action dated Jun. 22, 2018 for U.S. Appl. No. 15/474,312.
Office Action dated Nov. 23, 2018 in Canadian Application No. 2,824,51.
Office Action dated Nov. 26, 2018 in European Patent Application No. 12736203.6.
Restriction Requirement dated Jan. 26, 2018 for U.S. Appl. No. 15/474,312.
Restriction Requirement dated Apr. 8, 2019 for U.S. Appl. No. 15/964,717.
Notice of Allowance dated Jul. 5, 2019 for EP Patent Application No. 12736203.6.
Office Action dated Apr. 23, 2019 in JP Patent Application No, 2017-90501.
Office Action dated Jun. 4, 2019 in JP Patent Application No. 2018-517887.
Office Action dated Sep. 9, 2019 for U.S. Appl. No. 15/964,717.
Office Action dated Sep. 25, 2019 for KR Patent Application No. 10-2018-7013183.
Office Action dated Oct. 28, 2019 for AU Patent Application No. 2016334085.
Office Action dated Dec. 19, 2019 in Canadian Application No. 2,824,515.
Notice of Publication, dated Jan. 21, 2020, in Brazilian Application No. 1120130180463, and translation thereof.
Formal Office Action regarding National Genetic Patrimony/Traditional Knowledge, dated Feb. 11, 2020, in Brazilian Application No. 1120130180463, and translation thereof.
Extended European Search Report dated Jan. 20, 2020 in international application No. EP19206731.
Final Office Action dated Feb. 26, 2020 for U.S. Appl. No. 15/964,717.
Kluczyk et al., The two-headed peptide inhibitors of interleukin-1 action, Peptides, vol. 21, pp. 1411-1420, 2000.
Notice of Acceptance dated Jan. 14, 2019 in Australian Application No. 2017200489.
Office Action dated Feb. 4, 2020 in in Canadian Application No. 3000207.
Office Action dated Mar. 27, 2020 in in European Application No. 16854367.6.
Office Action dated Oct. 23, 2019 for KR Patent Application No. 10-2018-7013183.
Kang et al., Rational Design of Interleukin-21 Antagonist through Selective Elimination of the C Binding Epitope, The Journal of Biological Chemistry, vol. 285, No. 16, pp. 12223-12231, 2010.

* cited by examiner

Alignment of the D-helix region sequence of human γc-family cytokines

| | |

The consensus sequence for the γc- and the IL-2/IL-15-box.

| γc-Box | | D/E | F | L | Polar E Q N | Polar S/R | Non-polar | Non-polar I/K | | Aliphatic L/I | Non-polar | Q | Charged | | I/K | | T | S |
|---|---|---|---|---|---|---|---|---|---|---|---|---|---|---|---|---|---|---|
| IL-2/IL-15 box | | | | | | | | | | | | Q | | | I | | | |
| 1 | 2 | 3 | 4 | 5 | 6 | 7 | 8 | 9 | 10 | 11 | 12 | 13 | 14 | 15 | 16 | 17 | 18 | 19 |

Fig. 1B.

D-helix

*Fig. 8A*

```
(SEQ ID NO:134) IL-15              ------------ECEEIKEFLQSFVHIVQMFI--NTS
(SEQ ID NO:135) IL-2               ---------------TIVEFLNRWITFCQSII-STLT
(SEQ ID NO:136) IL-21              ---------------PLEFLERFKSLLQKMIHQHLS
(SEQ ID NO:137) IL-4               ------------NQSTLENFLERLKTIMREKYSKCSS
(SEQ ID NO:138) IL-7               LEENKSLKEQKKL-NDLCFLKRLLQEIKTCW-NKIL
(SEQ ID NO:139) IL-9               ---------------NALTFLKSLLEIFQREKMRGMR
                                                **:         :
                                                ●━━━━━━━━━━●
                                                   The γc-Box
```

*Fig. 8B*
```
(SEQ ID NO:155) IL-15     IKEFLQSFVHIVQMFINT-S
(SEQ ID NO:156) IL-9      IVEFLNRWITFCQSIISTLT
                          * ***: :: : * :*.* :
                              ◄---------►
                               IL-2/15 box
```

*Fig. 8C* aa position: 1-2-3-4-5-6-7-8-9-10-11-12-13-14-15-16-17-18-19
(SEQ ID NO:34) I-K-E-F-L-Q*-R*-F*-I*-H*-I*-V*-Q-S-I*-I-N-T-S ☐ : AA common to IL-2/IL-15
☐ : From the IL-15 sequence
☐ : From the IL-2 sequence
* : Chemical property conserved

Fig. 9A

| | Peptide ID | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|---|
| SEQ ID NO: 1 | Peptide ID | | E | F | L | Q | | | | | H/T | | | Q | M/S | | | N/S | T | S |
| SEQ ID NO: 2 | YT001 | I | V | E | F | L | Q | R | W | I | H | I | V | Q | M | F | I | S | T | S |
| SEQ ID NO: 3 | YT002 | I | V | E | F | L | Q | R | F | I | H | I | C | Q | M | F | I | S | T | S |
| SEQ ID NO: 4 | YT003 | I | V | E | F | L | Q | S | W | I | H | I | C | Q | M | F | I | S | T | S |
| SEQ ID NO: 5 | YT004 | I | K | E | F | L | Q | R | W | I | H | I | C | Q | M | F | I | S | T | S |
| SEQ ID NO: 6 | YT005 | I | V | E | F | L | Q | R | F | I | H | I | V | Q | M | | I | S | T | S |
| SEQ ID NO: 7 | YT006 | I | V | E | F | L | Q | S | W | I | H | I | V | Q | M | | I | S | T | S |
| SEQ ID NO: 8 | YT007 | I | K | E | F | L | Q | R | W | I | H | I | V | Q | M | | I | S | T | S |
| SEQ ID NO: 9 | YT008 | I | V | E | F | L | Q | S | F | I | H | I | C | Q | M | | I | S | T | S |
| SEQ ID NO: 10 | YT009 | I | K | E | F | L | Q | R | F | I | H | I | C | Q | M | | I | S | T | S |
| SEQ ID NO: 11 | YT010 | I | K | E | F | L | Q | S | W | I | H | I | C | Q | M | | I | S | T | S |
| SEQ ID NO: 12 | YT011 | I | K | E | F | L | Q | S | F | I | H | I | C | Q | M | | I | S | T | S |
| SEQ ID NO: 13 | YT012 | I | K | E | F | L | Q | S | W | I | H | I | V | Q | M | | I | S | T | S |
| SEQ ID NO: 14 | YT013 | I | K | E | F | L | Q | R | F | I | H | I | V | Q | M | | I | S | T | S |
| SEQ ID NO: 15 | YT014 | I | V | E | F | L | Q | S | F | I | H | I | V | Q | M | | I | S | T | S |
| SEQ ID NO: 16 | YT015 | I | K | E | F | L | Q | S | W | I | H | I | C | Q | M | | I | S | T | S |
| SEQ ID NO: 17 | YT016 | I | K | E | F | L | Q | R | F | I | H | I | C | Q | M | F | I | S | T | S |
| SEQ ID NO: 18 | YT017 | I | V | E | F | L | Q | S | F | I | H | I | C | Q | M | F | I | S | T | S |
| SEQ ID NO: 19 | YT018 | I | K | E | F | L | Q | R | W | I | H | I | V | Q | M | F | I | S | T | S |
| SEQ ID NO: 20 | YT019 | I | V | E | F | L | Q | S | W | I | H | I | V | Q | M | F | I | S | T | S |
| SEQ ID NO: 21 | YT020 | I | V | E | F | L | Q | R | F | I | H | I | V | Q | M | F | I | S | T | S |
| SEQ ID NO: 22 | YT021 | I | V | E | F | L | Q | R | W | I | H | I | V | Q | S | F | I | N | T | S |
| SEQ ID NO: 23 | YT022 | I | V | E | F | L | Q | R | F | I | H | I | C | Q | S | F | I | N | T | S |
| SEQ ID NO: 24 | YT023 | I | V | E | F | L | Q | S | W | I | H | I | C | Q | S | F | I | N | T | S |
| SEQ ID NO: 25 | YT024 | I | K | E | F | L | Q | R | W | I | H | I | C | Q | S | F | I | N | T | S |
| SEQ ID NO: 26 | YT025 | I | V | E | F | L | Q | R | F | I | H | I | V | Q | S | | I | N | T | S |
| SEQ ID NO: 27 | YT026 | I | V | E | F | L | Q | S | W | I | H | I | V | Q | S | | I | N | T | S |
| SEQ ID NO: 28 | YT027 | I | K | E | F | L | Q | R | W | I | H | I | V | Q | S | | I | N | T | S |
| SEQ ID NO: 29 | YT028 | I | V | E | F | L | Q | S | F | I | H | I | C | Q | S | | I | N | T | S |
| SEQ ID NO: 30 | YT029 | I | K | E | F | L | Q | R | F | I | H | I | C | Q | S | | I | N | T | S |
| SEQ ID NO: 31 | YT030 | I | K | E | F | L | Q | S | W | I | H | I | C | Q | S | | I | N | T | S |
| SEQ ID NO: 32 | YT031 | I | K | E | F | L | Q | S | F | I | H | I | C | Q | S | | I | N | T | S |
| SEQ ID NO: 33 | YT032 | I | K | E | F | L | Q | S | W | I | H | I | V | Q | S | | I | N | T | S |
| SEQ ID NO: 34 | YT033 | I | K | E | F | L | Q | R | F | I | H | I | V | Q | S | | I | N | T | S | = BNZ13 |
| SEQ ID NO: 35 | YT034 | I | V | E | F | L | Q | S | F | I | H | I | V | Q | S | | I | N | T | S |
| SEQ ID NO: 36 | YT035 | I | K | E | F | L | Q | S | W | I | H | I | C | Q | S | | I | N | T | S |
| SEQ ID NO: 37 | YT036 | I | K | E | F | L | Q | R | F | I | H | I | C | Q | S | F | I | N | T | S |
| SEQ ID NO: 38 | YT037 | I | V | E | F | L | Q | S | F | I | H | I | C | Q | S | F | I | N | T | S |
| SEQ ID NO: 39 | YT038 | I | K | E | F | L | Q | R | W | I | H | I | V | Q | S | F | I | N | T | S |
| SEQ ID NO: 40 | YT039 | I | V | E | F | L | Q | S | W | I | H | I | V | Q | S | F | I | N | T | S |
| SEQ ID NO: 41 | YT040 | I | V | E | F | L | Q | R | F | I | H | I | V | Q | S | F | I | N | T | S |

*Fig. 9B*

| | Peptide ID | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|---|
| SEQ ID NO: 1 | Peptide ID | | I | E | F | L | Q | | | | H/T | | | Q | M/S | | | I | N/S | T | S |
| SEQ ID NO: 42 | YT041 | | I | V | E | F | L | Q | R | W | I | T | I | V | Q | M | F | I | N | T | S |
| SEQ ID NO: 43 | YT042 | | I | V | E | F | L | Q | R | F | I | T | I | C | Q | M | F | I | N | T | S |
| SEQ ID NO: 44 | YT043 | | I | V | E | F | L | Q | S | W | I | T | I | C | Q | M | F | I | N | T | S |
| SEQ ID NO: 45 | YT044 | | I | K | E | F | L | Q | R | W | I | T | I | C | Q | M | F | I | N | T | S |
| SEQ ID NO: 46 | YT045 | | I | V | E | F | L | Q | R | F | I | T | I | V | Q | M | I | I | N | T | S |
| SEQ ID NO: 47 | YT046 | | I | V | E | F | L | Q | S | W | I | T | I | V | Q | M | I | I | N | T | S |
| SEQ ID NO: 48 | YT047 | | I | K | E | F | L | Q | R | W | I | T | I | V | Q | M | I | I | N | T | S |
| SEQ ID NO: 49 | YT048 | | I | V | E | F | L | Q | S | F | I | T | I | C | Q | M | I | I | N | T | S |
| SEQ ID NO: 50 | YT049 | | I | K | E | F | L | Q | R | F | I | T | I | C | Q | M | I | I | N | T | S |
| SEQ ID NO: 51 | YT050 | | I | K | E | F | L | Q | S | W | I | T | I | C | Q | M | I | I | N | T | S |
| SEQ ID NO: 52 | YT051 | | I | K | E | F | L | Q | S | F | I | T | I | C | Q | M | I | I | N | T | S |
| SEQ ID NO: 53 | YT052 | | I | K | E | F | L | Q | S | W | I | T | I | V | Q | M | I | I | N | T | S |
| SEQ ID NO: 54 | YT053 | | I | K | E | F | L | Q | R | F | I | T | I | V | Q | M | I | I | N | T | S |
| SEQ ID NO: 55 | YT054 | | I | V | E | F | L | Q | S | F | I | T | I | V | Q | M | I | I | N | T | S |
| SEQ ID NO: 56 | YT055 | | I | K | E | F | L | Q | S | W | I | T | I | C | Q | M | F | I | N | T | S |
| SEQ ID NO: 57 | YT056 | | I | K | E | F | L | Q | R | F | I | T | I | C | Q | M | F | I | N | T | S |
| SEQ ID NO: 58 | YT057 | | I | V | E | F | L | Q | S | F | I | T | I | C | Q | M | F | I | N | T | S |
| SEQ ID NO: 59 | YT058 | | I | K | E | F | L | Q | R | W | I | T | I | V | Q | M | F | I | N | T | S |
| SEQ ID NO: 60 | YT059 | | I | V | E | F | L | Q | S | W | I | T | I | V | Q | M | F | I | N | T | S |
| SEQ ID NO: 61 | YT060 | | I | V | E | F | L | Q | R | F | I | T | I | V | Q | M | F | I | N | T | S |
| SEQ ID NO: 62 | YT061 | | I | V | E | F | L | Q | R | W | I | T | I | V | Q | S | F | I | N | T | S |
| SEQ ID NO: 63 | YT062 | | I | V | E | F | L | Q | R | F | I | T | I | C | Q | S | F | I | N | T | S |
| SEQ ID NO: 64 | YT063 | | I | V | E | F | L | Q | S | W | I | T | I | C | Q | S | F | I | N | T | S |
| SEQ ID NO: 65 | YT064 | | I | K | E | F | L | Q | R | W | I | T | I | C | Q | S | F | I | N | T | S |
| SEQ ID NO: 66 | YT065 | | I | V | E | F | L | Q | R | F | I | T | I | V | Q | S | I | I | N | T | S |
| SEQ ID NO: 67 | YT066 | | I | V | E | F | L | Q | S | W | I | T | I | V | Q | S | I | I | N | T | S |
| SEQ ID NO: 68 | YT067 | | I | K | E | F | L | Q | R | W | I | T | I | V | Q | S | I | I | N | T | S |
| SEQ ID NO: 69 | YT068 | | I | V | E | F | L | Q | S | F | I | T | I | C | Q | S | I | I | N | T | S |
| SEQ ID NO: 70 | YT069 | | I | K | E | F | L | Q | R | F | I | T | I | C | Q | S | I | I | N | T | S |
| SEQ ID NO: 71 | YT070 | | I | K | E | F | L | Q | S | W | I | T | I | C | Q | S | I | I | N | T | S |
| SEQ ID NO: 72 | YT071 | | I | K | E | F | L | Q | S | F | I | T | I | C | Q | S | I | I | N | T | S |
| SEQ ID NO: 73 | YT072 | | I | K | E | F | L | Q | S | W | I | T | I | V | Q | S | I | I | N | T | S |
| SEQ ID NO: 74 | YT073 | | I | K | E | F | L | Q | R | F | I | T | I | V | Q | S | I | I | N | T | S |
| SEQ ID NO: 75 | YT074 | | I | V | E | F | L | Q | S | F | I | T | I | V | Q | S | I | I | N | T | S |
| SEQ ID NO: 76 | YT075 | | I | K | E | F | L | Q | S | W | I | T | I | C | Q | S | F | I | N | T | S |
| SEQ ID NO: 77 | YT076 | | I | K | E | F | L | Q | R | F | I | T | I | C | Q | S | F | I | N | T | S |
| SEQ ID NO: 78 | YT077 | | I | V | E | F | L | Q | S | F | I | T | I | C | Q | S | F | I | N | T | S |
| SEQ ID NO: 79 | YT078 | | I | K | E | F | L | Q | R | W | I | T | I | V | Q | S | F | I | N | T | S |
| SEQ ID NO: 80 | YT079 | | I | V | E | F | L | Q | S | W | I | T | I | V | Q | S | F | I | N | T | S |
| SEQ ID NO: 81 | YT080 | | I | V | E | F | L | Q | R | F | I | T | I | V | Q | S | F | I | N | T | S |

*Fig. 9C*

| | Peptide ID | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|---|
| SEQ ID NO: 1 | | I | | E | F | L | Q | | | I | H/T | I | | Q | M/S | | I | N/S | T | S |
| SEQ ID NO: 82 | YT081 | I | V | E | F | L | Q | R | W | I | T | I | V | Q | M | F | I | S | T | S |
| SEQ ID NO: 83 | YT082 | I | V | E | F | L | Q | R | F | I | T | I | C | Q | M | F | I | S | T | S |
| SEQ ID NO: 84 | YT083 | I | V | E | F | L | Q | S | W | I | T | I | C | Q | M | F | I | S | T | S |
| SEQ ID NO: 85 | YT084 | I | K | E | F | L | Q | R | W | I | T | I | C | Q | M | F | I | S | T | S |
| SEQ ID NO: 86 | YT085 | I | V | E | F | L | Q | R | F | I | T | I | V | Q | M | I | I | S | T | S |
| SEQ ID NO: 87 | YT086 | I | V | E | F | L | Q | S | W | I | T | I | V | Q | M | I | I | S | T | S |
| SEQ ID NO: 88 | YT087 | I | K | E | F | L | Q | R | W | I | T | I | V | Q | M | I | I | S | T | S |
| SEQ ID NO: 89 | YT088 | I | V | E | F | L | Q | S | F | I | T | I | C | Q | M | I | I | S | T | S |
| SEQ ID NO: 90 | YT089 | I | K | E | F | L | Q | R | F | I | T | I | C | Q | M | I | I | S | T | S |
| SEQ ID NO: 91 | YT090 | I | K | E | F | L | Q | S | W | I | T | I | C | Q | M | I | I | S | T | S |
| SEQ ID NO: 92 | YT091 | I | K | E | F | L | Q | S | F | I | T | I | C | Q | M | I | I | S | T | S |
| SEQ ID NO: 93 | YT092 | I | K | E | F | L | Q | S | W | I | T | I | V | Q | M | I | I | S | T | S |
| SEQ ID NO: 94 | YT093 | I | K | E | F | L | Q | R | F | I | T | I | V | Q | M | I | I | S | T | S |
| SEQ ID NO: 95 | YT094 | I | V | E | F | L | Q | S | F | I | T | I | V | Q | M | I | I | S | T | S |
| SEQ ID NO: 96 | YT095 | I | K | E | F | L | Q | S | W | I | T | I | C | Q | M | F | I | S | T | S |
| SEQ ID NO: 97 | YT096 | I | K | E | F | L | Q | R | F | I | T | I | C | Q | M | F | I | S | T | S |
| SEQ ID NO: 98 | YT097 | I | V | E | F | L | Q | S | F | I | T | I | C | Q | M | F | I | S | T | S |
| SEQ ID NO: 99 | YT098 | I | K | E | F | L | Q | R | W | I | T | I | V | Q | M | F | I | S | T | S |
| SEQ ID NO: 100 | YT099 | I | V | E | F | L | Q | S | W | I | T | I | V | Q | M | F | I | S | T | S |
| SEQ ID NO: 101 | YT100 | I | V | E | F | L | Q | R | F | I | T | I | V | Q | M | F | I | S | T | S |
| SEQ ID NO: 102 | YT101 | I | V | E | F | L | Q | R | W | I | H | I | V | Q | S | F | I | S | T | S |
| SEQ ID NO: 103 | YT102 | I | V | E | F | L | Q | R | F | I | H | I | C | Q | S | F | I | S | T | S |
| SEQ ID NO: 104 | YT103 | I | V | E | F | L | Q | S | W | I | H | I | C | Q | S | F | I | S | T | S |
| SEQ ID NO: 105 | YT104 | I | K | E | F | L | Q | R | W | I | H | I | C | Q | S | F | I | S | T | S |
| SEQ ID NO: 106 | YT105 | I | V | E | F | L | Q | R | F | I | H | I | V | Q | S | I | I | S | T | S |
| SEQ ID NO: 107 | YT106 | I | V | E | F | L | Q | S | W | I | H | I | V | Q | S | I | I | S | T | S |
| SEQ ID NO: 108 | YT107 | I | K | E | F | L | Q | R | W | I | H | I | V | Q | S | I | I | S | T | S |
| SEQ ID NO: 109 | YT108 | I | V | E | F | L | Q | S | F | I | H | I | C | Q | S | I | I | S | T | S |
| SEQ ID NO: 110 | YT109 | I | K | E | F | L | Q | R | F | I | H | I | C | Q | S | I | I | S | T | S |
| SEQ ID NO: 111 | YT110 | I | K | E | F | L | Q | S | W | I | H | I | C | Q | S | I | I | S | T | S |
| SEQ ID NO: 112 | YT111 | I | K | E | F | L | Q | S | F | I | H | I | C | Q | S | I | I | S | T | S |
| SEQ ID NO: 113 | YT112 | I | K | E | F | L | Q | S | W | I | H | I | V | Q | S | I | I | S | T | S |
| SEQ ID NO: 114 | YT113 | I | K | E | F | L | Q | R | F | I | H | I | V | Q | S | I | I | S | T | S |
| SEQ ID NO: 115 | YT114 | I | V | E | F | L | Q | S | F | I | H | I | V | Q | S | I | I | S | T | S |
| SEQ ID NO: 116 | YT115 | I | K | E | F | L | Q | S | W | I | H | I | C | Q | S | F | I | S | T | S |
| SEQ ID NO: 117 | YT116 | I | K | E | F | L | Q | R | F | I | H | I | C | Q | S | F | I | S | T | S |
| SEQ ID NO: 118 | YT117 | I | V | E | F | L | Q | S | F | I | H | I | C | Q | S | F | I | S | T | S |
| SEQ ID NO: 119 | YT118 | I | K | E | F | L | Q | R | W | I | H | I | V | Q | S | F | I | S | T | S |
| SEQ ID NO: 120 | YT119 | I | V | E | F | L | Q | S | W | I | H | I | V | Q | S | F | I | S | T | S |
| SEQ ID NO: 121 | YT120 | I | V | E | F | L | Q | R | F | I | H | I | V | Q | S | F | I | S | T | S |

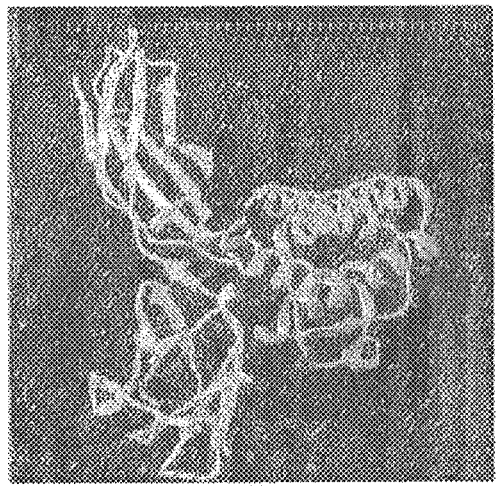
Fig. 9D
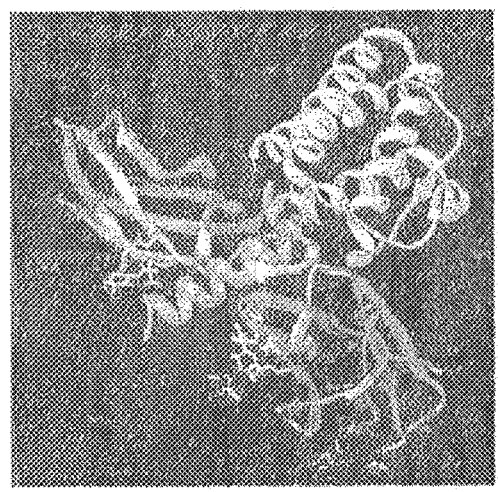 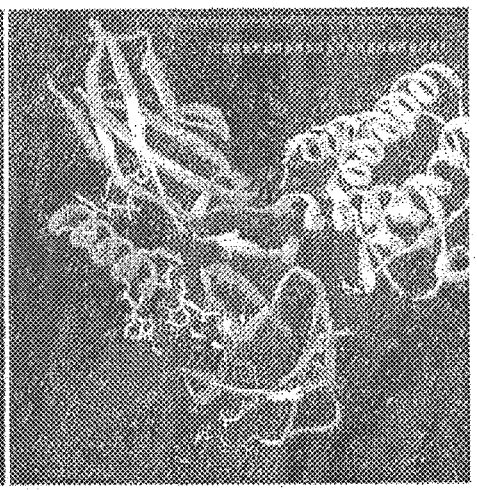
Fig. 9E Fig. 9F
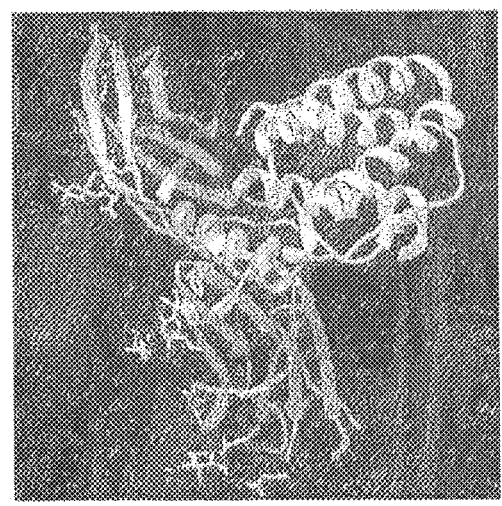 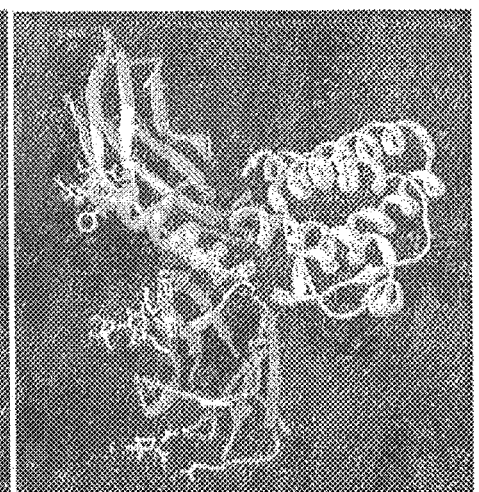
Fig. 9G Fig. 9H

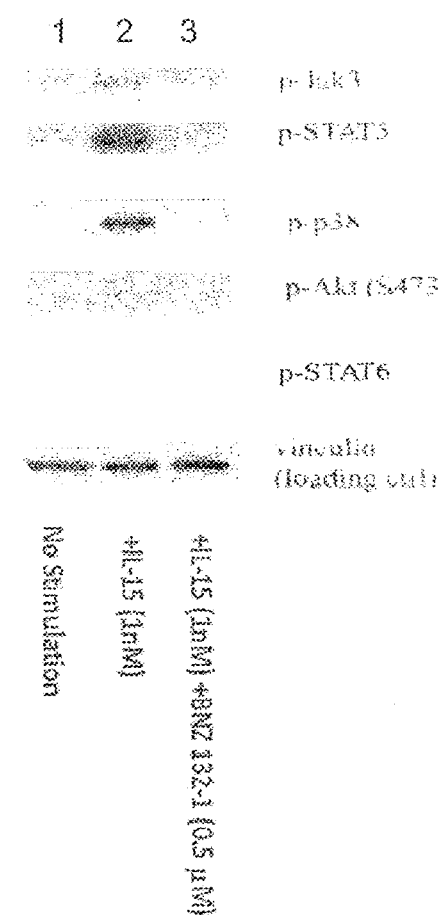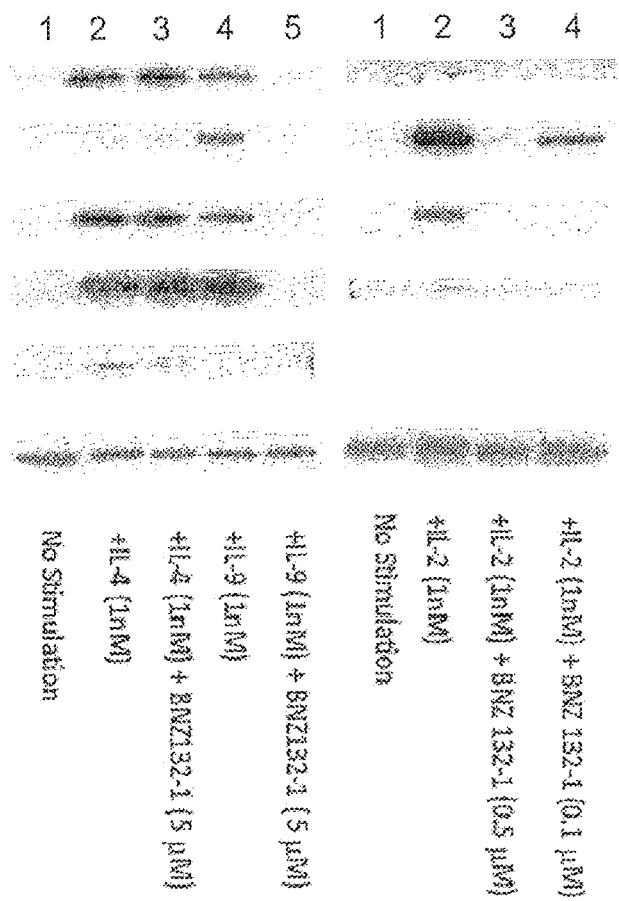
Fig. 13A  Fig. 13B  Fig. 13C

SEQUENCE LISTING

<160> NUMBER OF SEQ ID NOS: 161

<210> SEQ ID NO 1
<211> LENGTH: 14
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (7)..(7)
<223> OTHER INFORMATION: Xaa can be His or Thr
<220> FEATURE:
<221> NAME/KEY: misc_feature
<222> LOCATION: (10)..(10)
<223> OTHER INFORMATION: Xaa can be Met or Ser
<220> FEATURE:
<221> NAME/KEY: misc_feature
<222> LOCATION: (12)..(12)
<223> OTHER INFORMATION: Xaa can be Asn or Ser

<400> SEQUENCE: 1

Ile Glu Phe Leu Gln Ile Xaa Ile Gln Xaa Ile Xaa Thr Ser
1               5                   10

<210> SEQ ID NO 2
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 2

Ile Val Glu Phe Leu Gln Arg Trp Ile His Ile Val Gln Met Phe Ile
1               5                   10                  15

Ser Thr Ser

<210> SEQ ID NO 3
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 3

Ile Val Glu Phe Leu Gln Arg Phe Ile His Ile Cys Gln Met Phe Ile
1               5                   10                  15

Ser Thr Ser

<210> SEQ ID NO 4
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 4

Ile Val Glu Phe Leu Gln Ser Trp Ile His Ile Cys Gln Met Phe Ile
1               5                   10                  15

Ser Thr Ser

<210> SEQ ID NO 5
<211> LENGTH: 19
<212> TYPE: PRT
<213> ORGANISM: Artificial Sequence
<220> FEATURE:
<223> OTHER INFORMATION: Synthetic Peptide

```
<400> SEQUENCE: 5

Ile Lys Glu Phe Leu Gln Arg Trp Ile His Ile Cys Gln Met Phe Ile
1               5                   10                  15

Ser Thr Ser

<210> SEQ ID NO 6
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 6

Ile Val Glu Phe Leu Gln Arg Phe Ile His Ile Val Gln Met Ile Ile
1               5                   10                  15

Ser Thr Ser

<210> SEQ ID NO 7
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 7

Ile Val Glu Phe Leu Gln Ser Trp Ile His Ile Val Gln Met Ile Ile
1               5                   10                  15

Ser Thr Ser

<210> SEQ ID NO 8
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 8

Ile Lys Glu Phe Leu Gln Arg Trp Ile His Ile Val Gln Met Ile Ile
1               5                   10                  15

Ser Thr Ser

<210> SEQ ID NO 9
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 9

Ile Val Glu Phe Leu Gln Ser Phe Ile His Ile Cys Gln Met Ile Ile
1               5                   10                  15

Ser Thr Ser

<210> SEQ ID NO 10
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 10

Ile Lys Glu Phe Leu Gln Arg Phe Ile His Ile Cys Gln Met Ile Ile
```

```
1               5                   10                  15

Ser Thr Ser

<210> SEQ ID NO 11
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 11

Ile Lys Glu Phe Leu Gln Ser Trp Ile His Ile Cys Gln Met Ile Ile
1               5                   10                  15

Ser Thr Ser

<210> SEQ ID NO 12
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 12

Ile Lys Glu Phe Leu Gln Ser Phe Ile His Ile Cys Gln Met Ile Ile
1               5                   10                  15

Ser Thr Ser

<210> SEQ ID NO 13
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 13

Ile Lys Glu Phe Leu Gln Ser Trp Ile His Ile Val Gln Met Ile Ile
1               5                   10                  15

Ser Thr Ser

<210> SEQ ID NO 14
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 14

Ile Lys Glu Phe Leu Gln Arg Phe Ile His Ile Val Gln Met Ile Ile
1               5                   10                  15

Ser Thr Ser

<210> SEQ ID NO 15
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 15

Ile Val Glu Phe Leu Gln Ser Phe Ile His Ile Val Gln Met Ile Ile
1               5                   10                  15

Ser Thr Ser
```

```
<210> SEQ ID NO 16
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 16

Ile Lys Glu Phe Leu Gln Ser Trp Ile His Ile Cys Gln Met Phe Ile
1               5                   10                  15

Ser Thr Ser

<210> SEQ ID NO 17
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 17

Ile Lys Glu Phe Leu Gln Arg Phe Ile His Ile Cys Gln Met Phe Ile
1               5                   10                  15

Ser Thr Ser

<210> SEQ ID NO 18
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 18

Ile Val Glu Phe Leu Gln Ser Phe Ile His Ile Cys Gln Met Phe Ile
1               5                   10                  15

Ser Thr Ser

<210> SEQ ID NO 19
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 19

Ile Lys Glu Phe Leu Gln Arg Trp Ile His Ile Val Gln Met Phe Ile
1               5                   10                  15

Ser Thr Ser

<210> SEQ ID NO 20
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 20

Ile Val Glu Phe Leu Gln Ser Trp Ile His Ile Val Gln Met Phe Ile
1               5                   10                  15

Ser Thr Ser

<210> SEQ ID NO 21
<211> LENGTH: 19
<212> TYPE: PRT
```

```
<213> ORGANISM: Artificial Sequence
<220> FEATURE:
<223> OTHER INFORMATION: Synthetic Peptide

<400> SEQUENCE: 21

Ile Val Glu Phe Leu Gln Arg Phe Ile His Ile Val Gln Met Phe Ile
1               5                   10                  15

Ser Thr Ser

<210> SEQ ID NO 22
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 22

Ile Val Glu Phe Leu Gln Arg Trp Ile His Ile Val Gln Ser Phe Ile
1               5                   10                  15

Asn Thr Ser

<210> SEQ ID NO 23
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 23

Ile Val Glu Phe Leu Gln Arg Phe Ile His Ile Cys Gln Ser Phe Ile
1               5                   10                  15

Asn Thr Ser

<210> SEQ ID NO 24
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 24

Ile Val Glu Phe Leu Gln Ser Trp Ile His Ile Cys Gln Ser Phe Ile
1               5                   10                  15

Asn Thr Ser

<210> SEQ ID NO 25
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 25

Ile Lys Glu Phe Leu Gln Arg Trp Ile His Ile Cys Gln Ser Phe Ile
1               5                   10                  15

Asn Thr Ser

<210> SEQ ID NO 26
<211> LENGTH: 19
<212> TYPE: PRT
<213> ORGANISM: Artificial Sequence
<220> FEATURE:
<223> OTHER INFORMATION: Synthetic Peptide
```

-continued

<400> SEQUENCE: 26

Ile Val Glu Phe Leu Gln Arg Phe Ile His Ile Val Gln Ser Ile Ile
1               5                   10                  15

Asn Thr Ser

<210> SEQ ID NO 27
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 27

Ile Val Glu Phe Leu Gln Ser Trp Ile His Ile Val Gln Ser Ile Ile
1               5                   10                  15

Asn Thr Ser

<210> SEQ ID NO 28
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 28

Ile Lys Glu Phe Leu Gln Arg Trp Ile His Ile Val Gln Ser Ile Ile
1               5                   10                  15

Asn Thr Ser

<210> SEQ ID NO 29
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 29

Ile Val Glu Phe Leu Gln Ser Phe Ile His Ile Cys Gln Ser Ile Ile
1               5                   10                  15

Asn Thr Ser

<210> SEQ ID NO 30
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 30

Ile Lys Glu Phe Leu Gln Arg Phe Ile His Ile Cys Gln Ser Ile Ile
1               5                   10                  15

Asn Thr Ser

<210> SEQ ID NO 31
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 31

Ile Lys Glu Phe Leu Gln Ser Trp Ile His Ile Cys Gln Ser Ile Ile
1               5                   10                  15

Asn Thr Ser

<210> SEQ ID NO 32
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 32

Ile Lys Glu Phe Leu Gln Ser Phe Ile His Ile Cys Gln Ser Ile Ile
1               5                   10                  15

Asn Thr Ser

<210> SEQ ID NO 33
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 33

Ile Lys Glu Phe Leu Gln Ser Trp Ile His Ile Val Gln Ser Ile Ile
1               5                   10                  15

Asn Thr Ser

<210> SEQ ID NO 34
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 34

Ile Lys Glu Phe Leu Gln Arg Phe Ile His Ile Val Gln Ser Ile Ile
1               5                   10                  15

Asn Thr Ser

<210> SEQ ID NO 35
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 35

Ile Val Glu Phe Leu Gln Ser Phe Ile His Ile Val Gln Ser Ile Ile
1               5                   10                  15

Asn Thr Ser

<210> SEQ ID NO 36
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 36

Ile Lys Glu Phe Leu Gln Ser Trp Ile His Ile Cys Gln Ser Phe Ile
1               5                   10                  15

Asn Thr Ser

```
<210> SEQ ID NO 37
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 37

Ile Lys Glu Phe Leu Gln Arg Phe Ile His Ile Cys Gln Ser Phe Ile
1               5                   10                  15

Asn Thr Ser

<210> SEQ ID NO 38
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 38

Ile Val Glu Phe Leu Gln Ser Phe Ile His Ile Cys Gln Ser Phe Ile
1               5                   10                  15

Asn Thr Ser

<210> SEQ ID NO 39
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 39

Ile Lys Glu Phe Leu Gln Arg Trp Ile His Ile Val Gln Ser Phe Ile
1               5                   10                  15

Asn Thr Ser

<210> SEQ ID NO 40
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 40

Ile Val Glu Phe Leu Gln Ser Trp Ile His Ile Val Gln Ser Phe Ile
1               5                   10                  15

Asn Thr Ser

<210> SEQ ID NO 41
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 41

Ile Val Glu Phe Leu Gln Arg Phe Ile His Ile Val Gln Ser Phe Ile
1               5                   10                  15

Asn Thr Ser

<210> SEQ ID NO 42
<211> LENGTH: 19
<212> TYPE: PRT
<213> ORGANISM: Artificial Sequence
```

<220> FEATURE:
<223> OTHER INFORMATION: Synthetic Peptide

<400> SEQUENCE: 42

Ile Val Glu Phe Leu Gln Arg Trp Ile Thr Ile Val Gln Met Phe Ile
1               5                   10                  15

Asn Thr Ser

<210> SEQ ID NO 43
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 43

Ile Val Glu Phe Leu Gln Arg Phe Ile Thr Ile Cys Gln Met Phe Ile
1               5                   10                  15

Asn Thr Ser

<210> SEQ ID NO 44
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 44

Ile Val Glu Phe Leu Gln Ser Trp Ile Thr Ile Cys Gln Met Phe Ile
1               5                   10                  15

Asn Thr Ser

<210> SEQ ID NO 45
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 45

Ile Lys Glu Phe Leu Gln Arg Trp Ile Thr Ile Cys Gln Met Phe Ile
1               5                   10                  15

Asn Thr Ser

<210> SEQ ID NO 46
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 46

Ile Val Glu Phe Leu Gln Arg Phe Ile Thr Ile Val Gln Met Ile Ile
1               5                   10                  15

Asn Thr Ser

<210> SEQ ID NO 47
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 47

```
Ile Val Glu Phe Leu Gln Ser Trp Ile Thr Ile Val Gln Met Ile Ile
1               5                   10                  15

Asn Thr Ser

<210> SEQ ID NO 48
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 48

Ile Lys Glu Phe Leu Gln Arg Trp Ile Thr Ile Val Gln Met Ile Ile
1               5                   10                  15

Asn Thr Ser

<210> SEQ ID NO 49
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 49

Ile Val Glu Phe Leu Gln Ser Phe Ile Thr Ile Cys Gln Met Ile Ile
1               5                   10                  15

Asn Thr Ser

<210> SEQ ID NO 50
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 50

Ile Lys Glu Phe Leu Gln Arg Phe Ile Thr Ile Cys Gln Met Ile Ile
1               5                   10                  15

Asn Thr Ser

<210> SEQ ID NO 51
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 51

Ile Lys Glu Phe Leu Gln Ser Trp Ile Thr Ile Cys Gln Met Ile Ile
1               5                   10                  15

Asn Thr Ser

<210> SEQ ID NO 52
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 52

Ile Lys Glu Phe Leu Gln Ser Phe Ile Thr Ile Cys Gln Met Ile Ile
1               5                   10                  15
```

Asn Thr Ser

<210> SEQ ID NO 53
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 53

Ile Lys Glu Phe Leu Gln Ser Trp Ile Thr Ile Val Gln Met Ile Ile
1               5                   10                  15

Asn Thr Ser

<210> SEQ ID NO 54
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 54

Ile Lys Glu Phe Leu Gln Arg Phe Ile Thr Ile Val Gln Met Ile Ile
1               5                   10                  15

Asn Thr Ser

<210> SEQ ID NO 55
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 55

Ile Val Glu Phe Leu Gln Ser Phe Ile Thr Ile Val Gln Met Ile Ile
1               5                   10                  15

Asn Thr Ser

<210> SEQ ID NO 56
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 56

Ile Lys Glu Phe Leu Gln Ser Trp Ile Thr Ile Cys Gln Met Phe Ile
1               5                   10                  15

Asn Thr Ser

<210> SEQ ID NO 57
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 57

Ile Lys Glu Phe Leu Gln Arg Phe Ile Thr Ile Cys Gln Met Phe Ile
1               5                   10                  15

Asn Thr Ser

<210> SEQ ID NO 58

<211> LENGTH: 19
<212> TYPE: PRT
<213> ORGANISM: Artificial Sequence
<220> FEATURE:
<223> OTHER INFORMATION: Synthetic Peptide

<400> SEQUENCE: 58

Ile Val Glu Phe Leu Gln Ser Phe Ile Thr Ile Cys Gln Met Phe Ile
1               5                   10                  15

Asn Thr Ser

<210> SEQ ID NO 59
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 59

Ile Lys Glu Phe Leu Gln Arg Trp Ile Thr Ile Val Gln Met Phe Ile
1               5                   10                  15

Asn Thr Ser

<210> SEQ ID NO 60
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 60

Ile Val Glu Phe Leu Gln Ser Trp Ile Thr Ile Val Gln Met Phe Ile
1               5                   10                  15

Asn Thr Ser

<210> SEQ ID NO 61
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 61

Ile Val Glu Phe Leu Gln Arg Phe Ile Thr Ile Val Gln Met Phe Ile
1               5                   10                  15

Asn Thr Ser

<210> SEQ ID NO 62
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 62

Ile Val Glu Phe Leu Gln Arg Trp Ile Thr Ile Val Gln Ser Phe Ile
1               5                   10                  15

Asn Thr Ser

<210> SEQ ID NO 63
<211> LENGTH: 19
<212> TYPE: PRT
<213> ORGANISM: Artificial Sequence
<220> FEATURE:

<223> OTHER INFORMATION: Synthetic Peptide

<400> SEQUENCE: 63

Ile Val Glu Phe Leu Gln Arg Phe Ile Thr Ile Cys Gln Ser Phe Ile
1               5                   10                  15

Asn Thr Ser

<210> SEQ ID NO 64
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 64

Ile Val Glu Phe Leu Gln Ser Trp Ile Thr Ile Cys Gln Ser Phe Ile
1               5                   10                  15

Asn Thr Ser

<210> SEQ ID NO 65
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 65

Ile Lys Glu Phe Leu Gln Arg Trp Ile Thr Ile Cys Gln Ser Phe Ile
1               5                   10                  15

Asn Thr Ser

<210> SEQ ID NO 66
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 66

Ile Val Glu Phe Leu Gln Arg Phe Ile Thr Ile Val Gln Ser Ile Ile
1               5                   10                  15

Asn Thr Ser

<210> SEQ ID NO 67
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 67

Ile Val Glu Phe Leu Gln Ser Trp Ile Thr Ile Val Gln Ser Ile Ile
1               5                   10                  15

Asn Thr Ser

<210> SEQ ID NO 68
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 68

-continued

Ile Lys Glu Phe Leu Gln Arg Trp Ile Thr Ile Val Gln Ser Ile Ile
1               5                   10                  15

Asn Thr Ser

<210> SEQ ID NO 69
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 69

Ile Val Glu Phe Leu Gln Ser Phe Ile Thr Ile Cys Gln Ser Ile Ile
1               5                   10                  15

Asn Thr Ser

<210> SEQ ID NO 70
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 70

Ile Lys Glu Phe Leu Gln Arg Phe Ile Thr Ile Cys Gln Ser Ile Ile
1               5                   10                  15

Asn Thr Ser

<210> SEQ ID NO 71
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 71

Ile Lys Glu Phe Leu Gln Ser Trp Ile Thr Ile Cys Gln Ser Ile Ile
1               5                   10                  15

Asn Thr Ser

<210> SEQ ID NO 72
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 72

Ile Lys Glu Phe Leu Gln Ser Phe Ile Thr Ile Cys Gln Ser Ile Ile
1               5                   10                  15

Asn Thr Ser

<210> SEQ ID NO 73
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 73

Ile Lys Glu Phe Leu Gln Ser Trp Ile Thr Ile Val Gln Ser Ile Ile
1               5                   10                  15

Asn Thr Ser

<210> SEQ ID NO 74
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 74

Ile Lys Glu Phe Leu Gln Arg Phe Ile Thr Ile Val Gln Ser Ile Ile
1               5                   10                  15

Asn Thr Ser

<210> SEQ ID NO 75
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 75

Ile Val Glu Phe Leu Gln Ser Phe Ile Thr Ile Val Gln Ser Ile Ile
1               5                   10                  15

Asn Thr Ser

<210> SEQ ID NO 76
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 76

Ile Lys Glu Phe Leu Gln Ser Trp Ile Thr Ile Cys Gln Ser Phe Ile
1               5                   10                  15

Asn Thr Ser

<210> SEQ ID NO 77
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 77

Ile Lys Glu Phe Leu Gln Arg Phe Ile Thr Ile Cys Gln Ser Phe Ile
1               5                   10                  15

Asn Thr Ser

<210> SEQ ID NO 78
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 78

Ile Val Glu Phe Leu Gln Ser Phe Ile Thr Ile Cys Gln Ser Phe Ile
1               5                   10                  15

Asn Thr Ser

<210> SEQ ID NO 79
<211> LENGTH: 19

<212> TYPE: PRT
<213> ORGANISM: Artificial Sequence
<220> FEATURE:
<223> OTHER INFORMATION: Synthetic Peptide

<400> SEQUENCE: 79

Ile Lys Glu Phe Leu Gln Arg Trp Ile Thr Ile Val Gln Ser Phe Ile
1               5                   10                  15

Asn Thr Ser

<210> SEQ ID NO 80
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 80

Ile Val Glu Phe Leu Gln Ser Trp Ile Thr Ile Val Gln Ser Phe Ile
1               5                   10                  15

Asn Thr Ser

<210> SEQ ID NO 81
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 81

Ile Val Glu Phe Leu Gln Arg Phe Ile Thr Ile Val Gln Ser Phe Ile
1               5                   10                  15

Asn Thr Ser

<210> SEQ ID NO 82
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 82

Ile Val Glu Phe Leu Gln Arg Trp Ile Thr Ile Val Gln Met Phe Ile
1               5                   10                  15

Ser Thr Ser

<210> SEQ ID NO 83
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 83

Ile Val Glu Phe Leu Gln Arg Phe Ile Thr Ile Cys Gln Met Phe Ile
1               5                   10                  15

Ser Thr Ser

<210> SEQ ID NO 84
<211> LENGTH: 19
<212> TYPE: PRT
<213> ORGANISM: Artificial Sequence
<220> FEATURE:
<223> OTHER INFORMATION: Synthetic Peptide

```
<400> SEQUENCE: 84

Ile Val Glu Phe Leu Gln Ser Trp Ile Thr Ile Cys Gln Met Phe Ile
1               5                   10                  15

Ser Thr Ser

<210> SEQ ID NO 85
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 85

Ile Lys Glu Phe Leu Gln Arg Trp Ile Thr Ile Cys Gln Met Phe Ile
1               5                   10                  15

Ser Thr Ser

<210> SEQ ID NO 86
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 86

Ile Val Glu Phe Leu Gln Arg Phe Ile Thr Ile Val Gln Met Ile Ile
1               5                   10                  15

Ser Thr Ser

<210> SEQ ID NO 87
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 87

Ile Val Glu Phe Leu Gln Ser Trp Ile Thr Ile Val Gln Met Ile Ile
1               5                   10                  15

Ser Thr Ser

<210> SEQ ID NO 88
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 88

Ile Lys Glu Phe Leu Gln Arg Trp Ile Thr Ile Val Gln Met Ile Ile
1               5                   10                  15

Ser Thr Ser

<210> SEQ ID NO 89
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 89

Ile Val Glu Phe Leu Gln Ser Phe Ile Thr Ile Cys Gln Met Ile Ile
```

-continued

```
1               5                  10                 15

Ser Thr Ser

<210> SEQ ID NO 90
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 90

Ile Lys Glu Phe Leu Gln Arg Phe Ile Thr Ile Cys Gln Met Ile Ile
1               5                  10                 15

Ser Thr Ser

<210> SEQ ID NO 91
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 91

Ile Lys Glu Phe Leu Gln Ser Trp Ile Thr Ile Cys Gln Met Ile Ile
1               5                  10                 15

Ser Thr Ser

<210> SEQ ID NO 92
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 92

Ile Lys Glu Phe Leu Gln Ser Phe Ile Thr Ile Cys Gln Met Ile Ile
1               5                  10                 15

Ser Thr Ser

<210> SEQ ID NO 93
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 93

Ile Lys Glu Phe Leu Gln Ser Trp Ile Thr Ile Val Gln Met Ile Ile
1               5                  10                 15

Ser Thr Ser

<210> SEQ ID NO 94
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 94

Ile Lys Glu Phe Leu Gln Arg Phe Ile Thr Ile Val Gln Met Ile Ile
1               5                  10                 15

Ser Thr Ser
```

```
<210> SEQ ID NO 95
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 95

Ile Val Glu Phe Leu Gln Ser Phe Ile Thr Ile Val Gln Met Phe Ile
1               5                   10                  15

Ser Thr Ser

<210> SEQ ID NO 96
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 96

Ile Lys Glu Phe Leu Gln Ser Trp Ile Thr Ile Cys Gln Met Phe Ile
1               5                   10                  15

Ser Thr Ser

<210> SEQ ID NO 97
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 97

Ile Lys Glu Phe Leu Gln Arg Phe Ile Thr Ile Cys Gln Met Phe Ile
1               5                   10                  15

Ser Thr Ser

<210> SEQ ID NO 98
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 98

Ile Val Glu Phe Leu Gln Ser Phe Ile Thr Ile Cys Gln Met Phe Ile
1               5                   10                  15

Ser Thr Ser

<210> SEQ ID NO 99
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 99

Ile Lys Glu Phe Leu Gln Arg Trp Ile Thr Ile Val Gln Met Phe Ile
1               5                   10                  15

Ser Thr Ser

<210> SEQ ID NO 100
<211> LENGTH: 19
<212> TYPE: PRT
```

```
<213> ORGANISM: Artificial Sequence
<220> FEATURE:
<223> OTHER INFORMATION: Synthetic Peptide

<400> SEQUENCE: 100

Ile Val Glu Phe Leu Gln Ser Trp Ile Thr Ile Val Gln Met Phe Ile
1               5                   10                  15

Ser Thr Ser

<210> SEQ ID NO 101
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 101

Ile Val Glu Phe Leu Gln Arg Phe Ile Thr Ile Val Gln Met Phe Ile
1               5                   10                  15

Ser Thr Ser

<210> SEQ ID NO 102
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 102

Ile Val Glu Phe Leu Gln Arg Trp Ile His Ile Val Gln Ser Phe Ile
1               5                   10                  15

Ser Thr Ser

<210> SEQ ID NO 103
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 103

Ile Val Glu Phe Leu Gln Arg Phe Ile His Ile Cys Gln Ser Phe Ile
1               5                   10                  15

Ser Thr Ser

<210> SEQ ID NO 104
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 104

Ile Val Glu Phe Leu Gln Ser Trp Ile His Ile Cys Gln Ser Phe Ile
1               5                   10                  15

Ser Thr Ser

<210> SEQ ID NO 105
<211> LENGTH: 19
<212> TYPE: PRT
<213> ORGANISM: Artificial Sequence
<220> FEATURE:
<223> OTHER INFORMATION: Synthetic Peptide
```

```
<400> SEQUENCE: 105

Ile Lys Glu Phe Leu Gln Arg Trp Ile His Ile Cys Gln Ser Phe Ile
1               5                   10                  15

Ser Thr Ser

<210> SEQ ID NO 106
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 106

Ile Val Glu Phe Leu Gln Arg Phe Ile His Ile Val Gln Ser Ile Ile
1               5                   10                  15

Ser Thr Ser

<210> SEQ ID NO 107
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 107

Ile Val Glu Phe Leu Gln Ser Trp Ile His Ile Val Gln Ser Ile Ile
1               5                   10                  15

Ser Thr Ser

<210> SEQ ID NO 108
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 108

Ile Lys Glu Phe Leu Gln Arg Trp Ile His Ile Val Gln Ser Ile Ile
1               5                   10                  15

Ser Thr Ser

<210> SEQ ID NO 109
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 109

Ile Val Glu Phe Leu Gln Ser Phe Ile His Ile Cys Gln Ser Ile Ile
1               5                   10                  15

Ser Thr Ser

<210> SEQ ID NO 110
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 110

Ile Lys Glu Phe Leu Gln Arg Phe Ile His Ile Cys Gln Ser Ile Ile
1               5                   10                  15
```

Ser Thr Ser

<210> SEQ ID NO 111
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 111

Ile Lys Glu Phe Leu Gln Ser Trp Ile His Ile Cys Gln Ser Ile Ile
1               5                   10                  15

Ser Thr Ser

<210> SEQ ID NO 112
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 112

Ile Lys Glu Phe Leu Gln Ser Phe Ile His Ile Cys Gln Ser Ile Ile
1               5                   10                  15

Ser Thr Ser

<210> SEQ ID NO 113
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 113

Ile Lys Glu Phe Leu Gln Ser Trp Ile His Ile Val Gln Ser Ile Ile
1               5                   10                  15

Ser Thr Ser

<210> SEQ ID NO 114
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 114

Ile Lys Glu Phe Leu Gln Arg Phe Ile His Ile Val Gln Ser Ile Ile
1               5                   10                  15

Ser Thr Ser

<210> SEQ ID NO 115
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 115

Ile Val Glu Phe Leu Gln Ser Phe Ile His Ile Val Gln Ser Ile Ile
1               5                   10                  15

Ser Thr Ser

```
<210> SEQ ID NO 116
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 116

Ile Lys Glu Phe Leu Gln Ser Trp Ile His Ile Cys Gln Ser Phe Ile
1               5                   10                  15

Ser Thr Ser

<210> SEQ ID NO 117
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 117

Ile Lys Glu Phe Leu Gln Arg Phe Ile His Ile Cys Gln Ser Phe Ile
1               5                   10                  15

Ser Thr Ser

<210> SEQ ID NO 118
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 118

Ile Val Glu Phe Leu Gln Ser Phe Ile His Ile Cys Gln Ser Phe Ile
1               5                   10                  15

Ser Thr Ser

<210> SEQ ID NO 119
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 119

Ile Lys Glu Phe Leu Gln Arg Trp Ile His Ile Val Gln Ser Phe Ile
1               5                   10                  15

Ser Thr Ser

<210> SEQ ID NO 120
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 120

Ile Val Glu Phe Leu Gln Ser Trp Ile His Ile Val Gln Ser Phe Ile
1               5                   10                  15

Ser Thr Ser

<210> SEQ ID NO 121
<211> LENGTH: 19
<212> TYPE: PRT
<213> ORGANISM: Artificial Sequence
```

```
<220> FEATURE:
<223> OTHER INFORMATION: Synthetic Peptide

<400> SEQUENCE: 121

Ile Val Glu Phe Leu Gln Arg Phe Ile His Ile Val Gln Ser Phe Ile
1               5                   10                  15

Ser Thr Ser

<210> SEQ ID NO 122
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 122

Met Thr Thr His Leu Ile Leu Arg Ser Phe Lys Glu Phe Leu Gln Ser
1               5                   10                  15

Ser Ile Arg Ala Ile Arg Gln Met
            20

<210> SEQ ID NO 123
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 123

Leu Leu His Ser Leu Glu Val Leu Ser Arg Ala Val Arg Glu Leu Leu
1               5                   10                  15

Leu Leu Leu Ser Lys Ala
            20

<210> SEQ ID NO 124
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 124

Leu Thr His Leu Ile Glu Arg Ser Ser Arg Ala Val Leu Gln Ser Leu
1               5                   10                  15

Leu Arg Ala Ser Arg Gln
            20

<210> SEQ ID NO 125
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 125

Ala Gly Gly Leu His Leu Thr Leu Asp Trp Ala Val Arg Gly Leu Leu
1               5                   10                  15

Leu Leu Lys Thr Arg Leu
            20

<210> SEQ ID NO 126
<211> LENGTH: 23
<212> TYPE: PRT
<213> ORGANISM: Artificial Sequence
```

```
<220> FEATURE:
<223> OTHER INFORMATION: Synthetic Peptide

<400> SEQUENCE: 126

Val Leu Gln Glu Leu Ser Gln Trp Thr Val Arg Ser Ile His Asp Leu
1               5                   10                  15

Arg Phe Ile Ser Ser His Gln
            20

<210> SEQ ID NO 127
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 127

Val Phe Pro Ala Lys Val Leu Gly Leu Arg Val Cys Gly Leu Tyr Arg
1               5                   10                  15

Glu Trp Leu Ser Arg Thr
            20

<210> SEQ ID NO 128
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 128

Ala Leu Arg Lys Gly Val Arg Arg Thr Arg Pro Ser Arg Lys Gly Lys
1               5                   10                  15

Arg Leu Met Thr Arg Gly
            20

<210> SEQ ID NO 129
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 129

Phe Gln Lys Lys Leu Gly Cys Gln Leu Leu Gly Lys Tyr Lys Gln Ile
1               5                   10                  15

Ile Ala Val Leu Ala Gln
            20

<210> SEQ ID NO 130
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 130

Ile Lys Glu Phe Leu Gln Ser Phe Ile His Ile Val Gln Ser Ile Ile
1               5                   10                  15

Asn Thr

<210> SEQ ID NO 131
<211> LENGTH: 23
<212> TYPE: PRT
<213> ORGANISM: Artificial Sequence
```

```
<220> FEATURE:
<223> OTHER INFORMATION: Synthetic Peptide

<400> SEQUENCE: 131

Ser Leu Thr His Leu Ile Glu Arg Ser Ser Arg Ala Val Leu Gln Ser
1               5                   10                  15

Leu Leu Arg Ala Ser Arg Gln
            20

<210> SEQ ID NO 132
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 132

Gly Ser Gly Gly
1

<210> SEQ ID NO 133
<211> LENGTH: 24
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa can be Cys(acetylamino-propyl-mPEG40k)

<400> SEQUENCE: 133

Xaa Gly Ser Gly Gly Ile Lys Glu Phe Leu Gln Arg Phe Ile His Ile
1               5                   10                  15

Val Gln Ser Ile Ile Asn Thr Ser
            20

<210> SEQ ID NO 134
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 134

Glu Cys Glu Glu Ile Lys Glu Phe Leu Gln Ser Phe Val His Ile Val
1               5                   10                  15

Gln Met Phe Ile Asn Thr Ser
            20

<210> SEQ ID NO 135
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 135

Thr Ile Val Glu Phe Leu Asn Arg Trp Ile Thr Phe Cys Gln Ser Ile
1               5                   10                  15

Ile Ser Thr Leu Thr
            20

<210> SEQ ID NO 136
<211> LENGTH: 21
```

```
<212> TYPE: PRT
<213> ORGANISM: Artificial Sequence
<220> FEATURE:
<223> OTHER INFORMATION: Synthetic Peptide

<400> SEQUENCE: 136

Pro Leu Glu Phe Leu Glu Arg Phe Lys Ser Leu Leu Gln Lys Met Ile
1               5                   10                  15

His Gln His Leu Ser
            20

<210> SEQ ID NO 137
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 137

Asn Gln Ser Thr Leu Glu Asn Phe Leu Glu Arg Leu Lys Thr Ile Met
1               5                   10                  15

Arg Glu Lys Tyr Ser Lys Cys Ser Ser
            20                  25

<210> SEQ ID NO 138
<211> LENGTH: 34
<212> TYPE: PRT
<213> ORGANISM: Artificial Sequence
<220> FEATURE:
<223> OTHER INFORMATION: Synthetic Peptide

<400> SEQUENCE: 138

Leu Glu Glu Asn Lys Ser Leu Lys Glu Gln Lys Lys Leu Asn Asp Leu
1               5                   10                  15

Cys Phe Leu Lys Arg Leu Leu Gln Glu Ile Lys Thr Cys Trp Asn Lys
            20                  25                  30

Ile Leu

<210> SEQ ID NO 139
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 139

Asn Ala Leu Thr Phe Leu Glu Ser Leu Leu Glu Leu Phe Gln Lys Glu
1               5                   10                  15

Lys Met Arg Gly Met Arg
            20

<210> SEQ ID NO 140
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 140

Ile Lys Glu Phe Leu Gln Arg Phe Ile His Ile Val Gln Ser Ile Ile
1               5                   10                  15

Asn Thr Ser
```

<210> SEQ ID NO 141
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 141

Ile Lys Glu Phe Leu Gln Ser Phe Ile His Ile Val Gln Ser Ile Ile
1               5                   10                  15

Asn Thr Ser

<210> SEQ ID NO 142
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 142

Tyr Asn Arg Ser Thr Ser Pro Trp Asn Leu His Arg Asn Glu Asp Pro
1               5                   10                  15

Glu Arg Tyr Pro Ser Val Ile Trp Glu Ala Lys Cys
            20                  25

<210> SEQ ID NO 143
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 143

Asn Ser Arg Ile Ser Pro Trp Arg Tyr Glu Leu Asp Arg Asp Leu Asn
1               5                   10                  15

Arg Leu Pro Gln Asp Leu Tyr His Ala Arg Cys
            20                  25

<210> SEQ ID NO 144
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 144

Tyr Ser Arg Ser Thr Ser Pro Trp Arg Tyr His Arg Asp Arg Asp Pro
1               5                   10                  15

Asn Arg Tyr Pro Ser Asp Leu Tyr His Ala Lys Cys
            20                  25

<210> SEQ ID NO 145
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 145

Asn Lys Arg Ser Leu Ser Pro Trp Gly Tyr Ser Ile Asn His Asp Pro
1               5                   10                  15

Ser Arg Ile Pro Val Asp Leu Pro Glu Ala Arg Cys
            20                  25

-continued

```
<210> SEQ ID NO 146
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 146

His Gln Arg Ser Ile Ser Pro Trp Arg Tyr Arg Val Asp Thr Asp Glu
1               5                   10                  15

Asp Arg Tyr Pro Gln Lys Leu Ala Phe Ala Glu Cys
            20                  25

<210> SEQ ID NO 147
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 147

Asn Leu Arg Ser Val Ser Pro Trp Ala Tyr Arg Ile Ser Tyr Asp Pro
1               5                   10                  15

Ala Arg Tyr Pro Arg Tyr Leu Pro Glu Ala Tyr Cys
            20                  25

<210> SEQ ID NO 148
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 148

Asn Ser Arg Ile Ser Pro Trp Arg Tyr Glu Leu Asp Arg Asp Leu Asn
1               5                   10                  15

Arg Leu Pro Gln Asp Leu Tyr His Ala Arg Cys
            20                  25

<210> SEQ ID NO 149
<211> LENGTH: 41
<212> TYPE: PRT
<213> ORGANISM: Artificial Sequence
<220> FEATURE:
<223> OTHER INFORMATION: Synthetic Peptide

<400> SEQUENCE: 149

Ile Lys Glu Phe Leu Gln Ser Phe Ile His Ile Val Gln Ser Ile Ile
1               5                   10                  15

Asn Thr Ser Leu Thr His Leu Ile Glu Arg Ser Ser Arg Ala Val Leu
            20                  25                  30

Gln Ser Leu Leu Arg Ala Ser Arg Gln
        35                  40

<210> SEQ ID NO 150
<211> LENGTH: 54
<212> TYPE: PRT
<213> ORGANISM: Artificial Sequence
<220> FEATURE:
<223> OTHER INFORMATION: Synthetic Peptide

<400> SEQUENCE: 150

Ile Lys Glu Phe Leu Gln Ser Phe Ile His Ile Val Gln Ser Ile Ile
1               5                   10                  15
```

Asn Thr Ser Ala Ser Ala Ser Ala Ser Ala Ser Ala
            20                  25                  30

Leu Thr His Leu Ile Glu Arg Ser Arg Ala Val Leu Gln Ser Leu
            35                  40                  45

Leu Arg Ala Ser Arg Gln
        50

<210> SEQ ID NO 151
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 151

Ala Ser Ala Ser Ala Ser Ala Ser Ala Ser Ala
1               5                   10

<210> SEQ ID NO 152
<211> LENGTH: 96
<212> TYPE: PRT
<213> ORGANISM: Artificial Sequence
<220> FEATURE:
<223> OTHER INFORMATION: Synthetic Peptide

<400> SEQUENCE: 152

Ile Lys Glu Phe Leu Gln Ser Phe Ile His Ile Val Gln Ser Ile Ile
1               5                   10                  15

Asn Thr Ser Ala Ser Ala Ser Ala Ser Ala Ser Ala Ser Ala
            20                  25                  30

Leu Thr His Leu Ile Glu Arg Ser Arg Ala Val Leu Gln Ser Leu
            35                  40                  45

Leu Arg Ala Ser Arg Gln Ala Ser Ala Ser Ala Ser Ala Ser
        50                  55                  60

Ala Ser Ala Tyr Ser Arg Ser Thr Ser Pro Trp Arg Tyr His Arg Asp
65                  70                  75                  80

Arg Asp Pro Asn Arg Tyr Leu Pro Ser Asp Leu Tyr His Ala Lys Cys
                85                  90                  95

<210> SEQ ID NO 153
<211> LENGTH: 47
<212> TYPE: PRT
<213> ORGANISM: Artificial Sequence
<220> FEATURE:
<223> OTHER INFORMATION: Synthetic Peptide

<400> SEQUENCE: 153

Ile Lys Glu Phe Leu Gln Ser Phe Val His Ile Val Gln Met Phe Ile
1               5                   10                  15

Asn Thr Ser Thr Ala Arg Glu Ser Ala Leu Thr His Leu Ile Glu Arg
            20                  25                  30

Ser Ser Arg Ala Val Leu Gln Ser Leu Leu Arg Ala Ser Arg Gln
            35                  40                  45

<210> SEQ ID NO 154
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 154

```
Thr Ala Arg Glu Ser Ala
1               5
```

```
<210> SEQ ID NO 155
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 155

Ile Lys Glu Phe Leu Gln Ser Phe Val His Ile Val Gln Met Phe Ile
1               5                   10                  15

Asn Thr Ser
```

```
<210> SEQ ID NO 156
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 156

Ile Val Glu Phe Leu Asn Arg Trp Ile Thr Phe Cys Gln Ser Ile
1               5                   10                  15

Ile Ser Thr Leu Thr
            20
```

```
<210> SEQ ID NO 157
<211> LENGTH: 11
<212> TYPE: PRT
<213> ORGANISM: Artificial Sequence
<220> FEATURE:
<223> OTHER INFORMATION: Gamma-c-cytokine inhibitory peptide
<220> FEATURE:
<221> NAME/KEY: VARIANT
<222> LOCATION: (1)...(1)
<223> OTHER INFORMATION: Xaa = Asp or Glu
<220> FEATURE:
<221> NAME/KEY: VARIANT
<222> LOCATION: (4)...(4)
<223> OTHER INFORMATION: Xaa = Glu, Gln or Asn
<220> FEATURE:
<221> NAME/KEY: VARIANT
<222> LOCATION: (5)...(5)
<223> OTHER INFORMATION: Xaa = Ser or Arg
<220> FEATURE:
<221> NAME/KEY: VARIANT
<222> LOCATION: (6)...(6)
<223> OTHER INFORMATION: Xaa = any amino acid
<220> FEATURE:
<221> NAME/KEY: VARIANT
<222> LOCATION: (7)...(7)
<223> OTHER INFORMATION: Xaa = Ile or Lys
<220> FEATURE:
<221> NAME/KEY: VARIANT
<222> LOCATION: (8)...(8)
<223> OTHER INFORMATION: Xaa = any amino acid
<220> FEATURE:
<221> NAME/KEY: VARIANT
<222> LOCATION: (9)...(9)
<223> OTHER INFORMATION: Xaa = Leu or Ile
<220> FEATURE:
<221> NAME/KEY: VARIANT
<222> LOCATION: (10)...(10)
<223> OTHER INFORMATION: Xaa = any amino acid

<400> SEQUENCE: 157

Xaa Phe Leu Xaa Xaa Xaa Xaa Xaa Xaa Xaa Gln
1               5                   10
```

```
<210> SEQ ID NO 158
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 158

Ala Leu Thr Phe Leu Glu Ser Leu Leu Glu Leu Phe Gln Lys Glu
1               5                  10                  15

Lys Met Arg Gly Met Arg
            20

<210> SEQ ID NO 159
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 159

Leu Glu Asn Phe Leu Glu Arg Leu Lys Thr Ile Met Arg Glu Lys
1               5                  10                  15

Tyr Ser Lys Cys Ser Ser
            20

<210> SEQ ID NO 160
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 160

Asp Leu Cys Phe Leu Lys Arg Leu Leu Gln Glu Ile Lys Thr Cys
1               5                  10                  15

Trp Lys Ile Leu

<210> SEQ ID NO 161
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 161

Pro Lys Glu Phe Leu Glu Arg Phe Lys Ser Leu Leu Gln Lys Met
1               5                  10                  15

Ile His Gln His Leu Ser
            20
```

PEPTIDE CONJUGATES

CROSS REFERENCE TO RELATED APPLICATIONS

This application is a continuation application of U.S. application Ser. No. 15/179,900, filed Jun. 10, 2016, which is a continuation-in-part of U.S. application Ser. No. 14/852,240, filed Sep. 11, 2015, now U.S. Pat. No. 9,675,672, which is a continuation of U.S. application Ser. No. 13/868,725, filed Apr. 23, 2013, now U.S. Pat. No. 9,133,243, which is a continuation of U.S. application Ser. No. 13/589,017, filed Aug. 17, 2012, now U.S. Pat. No. 8,455,449, which is a continuation of International Application No. PCT/US2012/021566, filed Jan. 17, 2012, in the English language, which claims the benefit of U.S. Provisional Patent Application No. 61/433,890, filed Jan. 18, 2011, and U.S. Provisional Patent Application No. 61/527,049, filed Aug. 24, 2011, the contents of each of which are incorporated herein by reference in their entireties. U.S. application Ser. No. 14/852,240, filed Sep. 11, 2015, is also a continuation of U.S. application Ser. No. 13/980,305, filed Jul. 17, 2013, now U.S. Pat. No. 9,133,244, which is a U.S. National Stage Application under 35 U.S.C. § 371 of International Application No. PCT/US2012/021566, filed Jan. 17, 2012, the contents of each of which are incorporated herein by reference in their entireties. In addition, U.S. application Ser. No. 15/179,900, filed Jun. 10, 2016 is also a continuation-in-part of International Application No. PCT/US2014/069597, filed Dec. 10, 2014, which claims the benefit of U.S. Provisional Patent Application No. 61/914,063, filed Dec. 10, 2013, the contents of each of which are incorporated herein by reference in their entireties.

REFERENCE TO ELECTRONIC SEQUENCE LISTING

The present application is being filed along with an Electronic Sequence Listing. The Electronic Sequence Listing is provided as a file entitled BION001P4C1SEQLIST.txt, created and last modified on Apr. 18, 2018, which is 48,859 bytes in size. The information in the electronic format of the Electronic Sequence Listing is incorporated herein by reference in its entirety.

FIELD

In one aspect, the embodiments relate to peptide antagonists of γc-family cytokines, a group of mammalian cytokines that are mainly produced by epithelial, stromal and immune cells and control the normal and pathological activation of a diverse array of lymphocytes. The present embodiments also relate to the therapeutic uses of such peptides for the treatment of certain human diseases. The present embodiments also relate to the cosmeceutical applications of such peptides. Description of target diseases, cosmeceutical applications, as well as methods of administration, production, and commercialization of the peptides are disclosed.

In another aspect, the embodiments relate to single-polypeptide specific inhibitors of multiple members of ligand-receptor signaling families and the method of making thereof.

Aberrant signaling is implicated in the pathogenesis of a number of diseases. Correcting these aberrant signaling pathways show promise in addressing these diseases. However, there is substantial redundancy in signaling, and there is substantial risk of side effects when signaling is blocked too broadly.

Ligand-receptor interactions are central to many signaling pathways. Thus, disrupting ligand-receptor interactions or the signaling generated therefrom is a focus of therapeutic research. However, ligands or their receptors are often members of multi-member protein families, sometimes having only modest sequence variation. Thus, it has been a major challenge to specifically target ligands or receptors implicated in a defective signaling pathway without having deleterious effects on structurally related ligands or receptors having diverse, and often essential, signaling roles.

BACKGROUND

Cytokines are a diverse group of soluble factors that mediate various cell functions, such as, growth, functional differentiation, and promotion or prevention of programmed cell death (apoptotic cell death). Cytokines, unlike hormones, are not produced by specialized glandular tissues, but can be produced by a wide variety of cell types, such as epithelial, stromal or immune cells.

More than 100 cytokines have been identified so far and are considered to have developed by means of gene duplications from a pool of primordial genes (See Bazan, J. F. 1990, Immunol. Today 11:350-354). In support of this view, it is common for a group of cytokines to share a component in their multi-subunit receptor system. The most well-documented shared cytokine subunit in T cells is the common γ subunit (γc-subunit). The γc-subunit is shared by 6 known cytokines (Interleukin-2 (IL-2), Interleukin-4 (IL-4), Interleukin-7 (IL-7), Interleukin-9 (IL-9), Interleukin-15 (IL-15), and Interleukin-21 (IL-21), collectively called the "γc-cytokines" or "γc-family cytokines") and plays an indispensable role in transducing cell activation signals for all these cytokines. Additionally, for each of the γc-cytokines, there are one or two private cytokine-specific receptor subunits that when complexed with the γc-subunit, give rise to a fully functional receptor. (See Rochman et al., 2009, Nat Rev Immunol. 9: 480-90.)

The γc-family cytokines are a group of mammalian cytokines that are mainly produced by epithelial, stromal and immune cells and control the normal and pathological activation of a diverse array of lymphocytes. These cytokines are critically required for the early development of T cells in the thymus as well as their homeostasis in the periphery. For example, in the absence of the γc-subunit, T, B and NK cells do not develop in mice. (See Sugamura et al., 1996, Annu. Rev. Immunol. 14:179-205).

Pathologies Associated with the γc-Cytokines

Recent studies have indicated that dysregulation of expression and dysfunction of the γc-cytokines could lead to a wide variety of human immunologic and hematopoietic diseases.

IL-2

While IL-2 was historically considered a prototype T cell growth factor, the generation of a knockout mouse lacking IL-2 expression revealed that IL-2 is not critical for the growth or developmental of conventional T cells in vivo. Over-expression of IL-2, however, leads to a preferential expansion of a subset of T-cells; the regulatory T cells (T-regs). (See Antony et al., 2006, J. Immunol. 176:5255-66.) T-regs suppress the immune responses of other cells and thus act to maintain peripheral tolerance (reviewed in Sakaguchi et al., 2008, Cell 133:775-87). Breakdown of peripheral tolerance is thought to cause autoimmune diseases in humans. Thus, the immunosuppressive function of T-regs is thought to prevent the development of autoimmune diseases (See Sakaguchi et al., 2008, Cell 133:775-87). T-regs have also been implicated in cancer, where solid tumors and hematologic malignancies have been associated with elevated numbers of T-regs (See De Rezende et al., 2010, Arch. Immunol. Ther. Exp. 58:179-190).

IL-4

IL-4 is a non-redundant cytokine involved in the differentiation of T helper cells into the Th2 (T-helper type 2) subset, which promotes the differentiation of premature B cells into IgE producing plasma cells. IgE levels are elevated in allergic asthma. Thus, IL-4 is implicated in the development of allergic Asthma. Antibodies targeting IL-4 can be used to treat or even prevent the onset of allergic asthma. (See Le Buanec et al., 2007, Vaccine 25:7206-16.)

IL-7

IL-7 is essential for B cell development and the early development of T cells in the thymus. In mice, the abnormal expression of IL-7 causes T-cell-associated leukemia. (See Fisher et al., 1993, Leukemia 2:S66-68.) However, in humans, misregulation of IL-7 does not appear to cause T-cell-associated leukemia. In humans, up-regulation of IL-7 either alone or in combination with another γc-cytokine family member, IL-15, has been implicated in Large Granular Lymphocyte (LGL) leukemia.

IL-9

The role of IL-9 is still rather uncharacterized compared to other γc-cytokine family members. Mice depleted of the IL-9 gene appear normal and do not lack any subsets of cells in the lymphoid and hematopoietic compartments. Recent studies, however, reveal an in vivo role for IL-9 in the generation of Th17 (T-helper induced by interleukin-17) cells (See Littman et al., 2010, Cell 140(6):845-58; and Nowak et al., 2009, J. Exp. Med. 206: 1653-60).

IL-15

IL-15 is critically involved in the development of NK cells, NK-T cells, some subsets of intraepithelial lymphocytes (IELs), γδ-T cells, and memory-phenotype CD8 T-cells (See Waldmann, 2007, J. Clin. Immunol. 27:1-18; and Tagaya et al., 1996, EMBO J. 15:4928-39.) Over-expression of IL-15 in mice leads to the development of NK-T cell and CD8 cell type T cell leukemia (See Fehniger et al., 2001, J. Exp. Med. 193:219-31; Sato et al. 2011 Blood in press). These experimentally induced leukemias appear similar to LGL (large-granular lymphocyte) leukemia in humans, since in both instances the leukemic cells express CD8 antigen.

It is also suspected that IL-15-mediated autocrine mechanisms may be involved in the leukemic transformation of CD4 T lymphocytes. (See Azimi et al., 1998, Proc. Natl. Acad. Sci. 95:2452-7; Azimi et al., 1999, J. Immunol. 163:4064-72; Azimi et al., 2000, AIDS Res. Hum. Retroviruses 16:1717-22; and Azimi et al., 2001, Proc. Natl. Acad. Sci. 98:14559-64). For example, CD4-tropic HTLV-I, which causes Adult T cell leukemia in humans, induces autocrine growth of virus-transformed T cells through the production of IL-15 and IL-15Rα (Azimi et al., 1998, Proc. Natl. Acad. Sci. 95:2452-7).

In addition to leukemic transformation, recent studies implicate IL-15 in the pathological development of Celiac disease (CD), an autoimmune disease. IL-15 is known to stimulate the differentiation of NK, CD8 and intestinal intraepithelial lymphocyte (IEL) cells into lymphokine-activated killer (LAK) cells by inducing the expression of cytolytic enzymes (i.e., Granzyme and Perforin) as well as interferon-γ. Celiac Disease (denoted CD from herein) is an immune-mediated enteropathy that is triggered by the consumption of gluten-containing food in individuals that express specific HLA-DQ alleles. The prevalence of this disease is 1% in the western population. The only current treatment for CD is the complete elimination of gluten from the patient's diet. The pathology of CD is mainly caused by extensive damage to the intestinal mucosa, which is caused by activated CD8 T cells that have infiltrated to the intestinal lamina propria. These CD8 T cells appear to be activated through mechanisms involving IL-15. One recent publication demonstrated in mice that ectopic over-expression of IL-15 by enterocytes leads to the development of enteropathy, which closely resembles the lesions in CD patients. Neutralization of IL-15 activity dramatically diminished the pathological changes. Thus, an intervention blocking the activation of CD8 T cells by IL-15 appears to provide an alternative strategy in managing CD to the conventional gluten-free diet.

IL-21

IL-21 is the most recently discovered member of the γc-family. Unlike other family members, IL-21 does not appear to have potent growth-promoting effects. Instead, IL-21 is thought to function more as a differentiation factor than a factor controlling cellular proliferation (See Tagaya, 2010, J. Leuk. Biol. 87:13-15).

Current Strategies for Treating γc-Cytokine-Mediated Disorders

Because the γc-cytokines are thought to be involved in numerous human diseases, several methods of treating γc-cytokine-implicated diseases by inhibiting γc-cytokine family activities have been proposed. These methods include the use of cytokine-specific monoclonal antibodies to neutralize the targeted cytokine's activity in vivo; use of monoclonal antibodies targeting the private cytokine-specific receptor subunits (subunits other than the shared γc-subunit) to selectively inhibit cytokine activity; and use of chemical inhibitors that block the downstream intracellular cytokine signal transduction pathway. While cytokine-specific antibodies are often the first choice in designing therapeutics, cytokines that share receptor components display overlapping functions (See Paul, W. E., 1989, Cell 57:521-24) and more than one cytokine can co-operate to cause a disease (see example described below). Thus, approaches involving neutralization of a single cytokine may not be effective in the treatment of cytokine-implicated human diseases.

Strategies for designing therapeutics that inhibit the function of multiple cytokines via antibodies which recognize a shared receptor component have also been proposed. However, the multi-subunit nature of cytokine receptor systems and the fact that functional receptors for a single cytokine can assume different configurations makes this approach difficult. For example, a functional IL-15 receptor can be either IL-15Rβ/γc or IL-15Rα/β/γc. (See Dubois et al., 2002, Immunity 17:537-47.) An antibody against the IL-15Rβ receptor (TMβ1), is an efficient inhibitor of the IL-15 function, but only when the IL-15Rα molecule is absent from the receptor complex. (See Tanaka et al., 1991, J. Immunol. 147:2222-28.) Thus, the effectiveness of a monoclonal anti-receptor antibody, whether raised against a shared or a private subunit, can be context-dependent and is unpredictable in vivo.

Although clinical use of monoclonal antibodies against biologically active factors or receptors associated with the pathogenesis of diseases is an established practice, there are few demonstrations of successful outcomes. Moreover, establishment of a clinically-suited monoclonal antibody treatment is a long and difficult process, with the successful generation of a neutralizing antibody largely a matter of luck. For example, due to the critical importance of the γc-subunit in mediating signaling by γc-family cytokines, many attempts to generate polyclonal and monoclonal antibodies against the γc-subunit have been made and there exist many commercial antibodies recognizing the γc-subunit in mice and in humans. Curiously, however, none of these anti-γc-subunit antibodies block the function of the γc-cytokines.

Another problem with the therapeutic use of monoclonal antibodies is that monoclonal antibodies are usually generated by immunizing rodents with human proteins, so the generated antibody is a foreign protein and thus highly immunogenic. To circumvent this problem, the amino acid sequence of the monoclonal antibody is molecularly modified so that the antibody molecule is recognized as a human immunoglobulin (a process called humanization), but this process requires time and expense.

Targeting JAK3, as an Existing Alternative Example for the Inhibition of Multiple γc-Cytokines The interaction between the γc-subunit and a γc-cytokine leads to the activation of an intracellular protein tyrosine kinase called Janus kinase 3 (Jak3). Jak3, in turn, phosphorylates multiple signaling molecules including STAT5, and PI3 kinase. The interaction of the γc-subunit and Jak3 is very specific. In fact, there is no other receptor molecule that recruits Jak3 for signal transduction. (See O'Shea, 2004, Ann. Rheum. Dis. 63:(suppl. II):ii67-7.) Thus, the inhibition of cytokine signaling through the γc-subunit can be accomplished by blocking the activity of Jak3 kinase. Accordingly, multiple chemical inhibitors that target the kinase activity of Jak3 have been introduced to the market. (See Pesu et al., 2008, Immunol. Rev. 223:132-142.) One such example is CP690,550.

The major shortcoming of these protein kinase inhibitors is the lack of specificity to Jak3 kinase. These drugs intercept the binding of ATP (adenosine-triphosphate) molecules to Jak3 kinase, a common biochemical reaction for many protein kinases, and thus tend to block the action of multiple intracellular protein kinases that are unrelated to Jak3 kinase whose actions are critically needed for the well-being of normal cells in various tissues. Thus, more specific inhibitors of signaling through the γc-subunit are needed.

There is therefore a great need for an alternative strategy for treating γc-cytokine-implicated diseases.

SUMMARY

One embodiment relates to an isolated or purified peptide, consisting essentially of a 19-mer amino acid sequence I-K-E-F-L-Q-R-F-I-H-I-V-Q-S-I-I-N-T-S(SEQ ID NO: 34) (referred to herein as "BNZ-γ" (BNZ-gamma)).

Another embodiment relates to a method for blocking signaling by one or more γc-cytokine family members, comprising contacting a cell with an isolated or purified peptide consisting essentially of amino acid sequence I-K-E-F-L-Q-R-F-I-H-I-V-Q-S-I-I-N-T-S (SEQ ID NO: 34).

Another embodiment relates to a method for blocking signaling by one or more γc-cytokine family members, comprising contacting a cell with an isolated or purified peptide consisting essentially of amino acid sequence I-K-E-F-L-Q-R-F-I-H-I-V-Q-S-I-I-N-T-S (SEQ ID NO: 34), wherein the cell is an immune cell.

Another embodiment relates to a method for blocking signaling by one or more γc-cytokine family members, comprising contacting a cell with an isolated or purified peptide consisting essentially of amino acid sequence I-K-E-F-L-Q-R-F-I-H-I-V-Q-S-I-I-N-T-S (SEQ ID NO: 34), wherein the γc-cytokine family member is selected from the group consisting of: IL-2, IL-4, IL-7, IL-9, IL-15, or IL-21.

Another embodiment relates to derivative peptides of a peptide consisting of amino acid sequence I-K-E-F-L-Q-R-F-I-H-I-V-Q-S-I-I-N-T-S(SEQ ID NO: 34), wherein the derivative peptide has similar physico-chemical properties as the peptide consisting of amino acid sequence I-K-E-F-L-Q-R-F-I-H-I-V-Q-S-I-I-N-T-S(SEQ ID NO: 34), but the derivative peptide has distinct biological activity.

Another embodiment relates to a custom peptide wherein the amino acid sequence of the custom peptide differs from amino acid sequence I-K-E-F-L-Q-R-F-I-H-I-V-Q-S-I-I-N-T-S(SEQ ID NO: 34) by conservative substitution of one or more amino acids.

Another embodiment relates to a custom peptide, consisting essentially of a 19-mer amino acid sequence I-K-E-F-L-Q-R-F-I-H-I-V-Q-S-I-I-N-T-S(SEQ ID NO: 34).

Another embodiment relates to a custom peptide wherein the amino acid sequence of the custom peptide differs from amino acid sequence I-K-E-F-L-Q-R-F-I-H-I-V-Q-S-I-I-N-T-S(SEQ ID NO: 34) by substituting another polar amino acid for the glutamine (Q) at the 6-position.

Another embodiment relates to a custom peptide wherein the amino acid sequence of the custom peptide differs from the amino acid sequence I-K-E-F-L-Q-R-F-I-H-I-V-Q-S-I-I-N-T-S(SEQ ID NO: 34) by substitution of one or more amino acids with similar biochemical properties to the amino acids comprising sequence I-K-E-F-L-Q-R-F-I-H-I-V-Q-S-I-I-N-T-S(SEQ ID NO: 34).

Another embodiment relates to custom peptide derivatives of the amino acid sequence I-K-E-F-L-Q-R-F-I-H-I-V-Q-S-I-I-N-T-S, wherein the amino acid sequence of the custom peptide has similar physico-chemical properties as a peptide of the amino acid sequence I-K-E-F-L-Q-R-F-I-H-I-V-Q-S-I-I-N-T-S(SEQ ID NO: 34), but has distinct biological activity, wherein the amino acid sequence of the custom peptide shares at least 50% sequence homology to the amino acid sequence I-K-E-F-L-Q-R-F-I-H-I-V-Q-S-I-I-N-T-S(SEQ ID NO: 34).

Another embodiment relates to a conjugation of a peptide consisting essentially of amino acid sequence I-K-E-F-L-Q-R-F-I-H-I-V-Q-S-I-I-N-T-S(SEQ ID NO: 34) to the N-termini, C-termini and/or to the side residues of existing biological proteins/peptides for efficient delivery and improved biological stability in vivo. Examples of such conjugations are BSA, albumin, Fc region of IgG, other biological proteins that function as scaffold, Poly Ethylene Glycol or (PEG) at different molecular weights or other similar moieties.

Another embodiment relates to conjugation of custom peptide derivatives of the amino acid sequence I-K-E-F-L-Q-R-F-I-H-I-V-Q-S-I-I-N-T-S(SEQ ID NO: 34) to the N-termini, C-termini and/or to the side residues of existing biological proteins/peptides, wherein the amino acid sequence of the custom peptide has similar physico-chemical properties as a peptide of the amino acid sequence I-K-E-F-L-Q-R-F-I-H-I-V-Q-S-I-I-N-T-S(SEQ ID NO: 34), but has distinct biological activity, wherein the amino acid sequence of the custom peptide shares at least 50% sequence homology to the amino acid sequence I-K-E-F-L-Q-R-F-I-H-I-V-Q-S-I-I-N-T-S(SEQ ID NO: 34). Examples of such conjugations are albumin, Fc region of IgG, other biological proteins that function as scaffold, or Poly Ethylene Glycol or (PEG) at different molecular weights or other similar moieties.

Another embodiment relates a method of inhibiting γc-cytokine activity comprising, contacting a γc-cytokine with a peptide consisting essentially of amino acid sequence I-K-E-F-L-Q-R-F-I-H-I-V-Q-S-I-I-N-T-S(SEQ ID NO: 34).

Another embodiment relates to polyclonal and monoclonal antibodies raised against an immunogenic peptide comprising amino acid sequence I-K-E-F-L-Q-R-F-I-H-I-V-Q-S-I-I-N-T-S(SEQ ID NO: 34).

Another embodiment relates to polyclonal and monoclonal antibodies raised against custom peptide derivatives of the amino acid sequence I-K-E-F-L-Q-R-F-I-H-I-V-Q-S-I-I-N-T-S(SEQ ID NO: 34), wherein the amino acid sequence of the custom peptide has similar physico-chemical properties as a peptide of the amino acid sequence I-K-E-F-L-Q-R-F-I-H-I-V-Q-S-I-I-N-T-S(SEQ ID NO: 34), but has distinct biological activity, and wherein the amino acid sequence of the custom peptide shares at least 50% sequence homology to the amino acid sequence I-K-E-F-L-Q-R-F-I-H-I-V-Q-S-I-I-N-T-S(SEQ ID NO: 34).

Disclosed herein, in one aspect, are methods and compositions related to the selective, specific disruption of multiple ligand-receptor signaling interactions. In some embodiments these interactions involve multiple cytokines in a single receptor family. In some embodiments multiple ligand receptor interactions from at least two distinct ligand-receptor families are disrupted. In some embodiments the compositions comprise polypeptides having composite sequences that comprise sequence fragments of two or more ligand binding sites. In some embodiments the sequence fragments of two or more ligand binding sites are arranged to conserve the secondary structure of each of the ligands from which the sequence fragments were taken.

Methods and compositions disclosed herein relate to the selective blocking of specific ligand-receptor interactions within ligand-receptor families and, optionally, across two or more than two ligand-receptor families.

One aspect of the disclosures provided herein relates to a method of designing an antagonist peptide against a family of cytokines that share a common receptor, in such a way to selectively inhibit binding interfaces of a first group of the cytokines among the family of the cytokines with the common receptor but not all of the cytokines of the family. The method may comprise obtaining amino-acid sequences of the first group of the cytokines, identifying, from the amino acid sequences of the first group of the cytokines, receptor binding sites or amino acids necessary to the binding of the first group of cytokines with the common receptor, and designing a composite peptide sequence that comprises at least part of the receptor binding sites and/or the amino acids necessary to the binding of the first group of the cytokines with the common receptor.

Another aspect of the disclosures provided herein relates to a method of designing a first inhibitor polypeptide of a first ligand-receptor complex and a second ligand receptor complex, comprising the steps of obtaining the polypeptide sequence of a first ligand, obtaining the polypeptide sequence of a second ligand, identifying a structurally conserved region common to the first ligand and the second ligand, wherein the region of the first ligand interacts with a receptor of the first ligand, and the region of the second ligand interacts with a receptor of the second ligand, and composing a chimeric polypeptide sequence consistent with or comprising the structurally conserved region, the chimeric polypeptide having a sequence comprising sequence fragments of the first ligand and the second ligand, wherein a polypeptide comprising the chimeric polypeptide sequence selectively inhibits a first ligand-receptor complex of the first ligand and a second ligand-receptor complex of the second ligand.

In some embodiments, the polypeptide may not inhibit a third ligand-receptor complex of a third ligand. In some other embodiments, the third ligand may comprise a polypeptide sequence that is not substantially more different from the first ligand or from the second ligand than said first ligand is from the second ligand.

In other embodiments, the first ligand-receptor complex and the second ligand-receptor complex may comprise a common receptor component.

In other embodiments, the first ligand-receptor complex, the second ligand-receptor complex and the third ligand-receptor complex may comprise a common receptor component.

In other embodiments, each of the sequence fragments may be fewer than 11 residues. In still other embodiments, each of the sequence fragments may be fewer than 10 residues. In still other embodiments, each of the sequence fragments may be fewer than 6 residues. In still other embodiments, each of the sequence fragments may be fewer than 4 residues.

In other embodiments, the chimeric polypeptide may comprise at least three sequence fragments of the first ligand.

In some other embodiments, each of the sequence fragments may uniquely map to a single ligand. In still other embodiments, at least one of the sequence fragments may map to at least two ligands.

In other embodiments, the structurally conserved region may comprise a helix comparable to the native helix structure of the original ligand that binds to the receptor.

In other embodiments, the first ligand may be a chemokine. In still other embodiments, the first ligand may be a hormone. In still other embodiments, the first ligand may be a growth factor. In still other embodiments, the first ligand may be a cytokine. In still other embodiments, the first ligand may be selected from IL-2, IL-4, IL-7, IL-9, IL-15, IL-21, IL-6, IL-11, CNTF, CT-1, OSM, LIF, IL-27, IL-17A, IL-17B, IL-17C, IL-17D, IL-17E (IL-25), and IL-17F.

In some other embodiments, the second ligand may be selected from IL-2, IL-4, IL-7, IL-9, IL-15, IL-21, IL-6, IL-11, CNTF, CT-1, OSM, LIF, IL-27, IL-17A, IL-17B, IL-17C, IL-17D, IL-17E (IL-25), and IL-17F.

In still other embodiments, the third ligand may be selected from IL-2, IL-4, IL-7, IL-9, IL-15, IL-21, IL-6, IL-11, CNTF, CT-1, OSM, LIF, IL-27, IL-17A, IL-17B, IL-17C, IL-17D, IL-17E (IL-25), and IL-17F.

In other embodiments, the first ligand may be a pathogen ligand. The pathogen may be a virus, an *eubacterium*, or a eukaryote.

In still some other embodiments, the method may further comprise inhibiting a fourth ligand-receptor complex, the method further comprising providing a second inhibitor polypeptide sequence, wherein the second inhibitor polypeptide sequence may comprise a sequence of a target region of the fourth ligand of the fourth ligand receptor complex.

In still some other embodiments, the ligand of the fourth ligand-receptor complex may be selected from the list consisting of IL-2, IL-4, IL-7, IL-9, IL-15, IL-21, IL-6, IL-11, CNTF, CT-1, OSM, LIF, IL-27, IL-17A, IL-17B, IL-17C, IL-17D, IL-17E (IL-25), and IL-17F.

In still some other embodiments, the second inhibitor polypeptide sequence may be covalently tethered to the first inhibitor polypeptide.

In still some other embodiments, the second inhibitor polypeptide sequence may be covalently tethered to the first inhibitor polypeptide through any of structure selected from direct binding, a linker comprising PEG, a polypeptide linker sequence, or a hydrocarbon linker.

In still some other embodiments, the second inhibitor polypeptide sequence may be non-covalently bound to the first inhibitor polypeptide.

In still some other embodiments, the method may further comprise providing a hydrophobic intermediary to which the first inhibitor polypeptide and the second polypeptide are non-covalently bound. The provided hydrophobic intermediary may comprise a lipid.

Still another aspect of the disclosures provided herein relates to a composition for the selective simultaneous inhibition of at least a first ligand-receptor complex and a second ligand-receptor complex, the composition comprising a first polypeptide having an amino acid sequence comprising a plurality of sequence fragments of the first ligand and a plurality of sequence fragments of the second ligand.

In some embodiments, each of the sequence fragments may comprise not more than 10, 9, 8, 7, 6, 5, 4, or 3 consecutive residues of the first ligand or the second ligand.

In still some other embodiments, each of the sequence fragments may uniquely map to a unique ligand.

In still some other embodiments, at least one of the sequence fragments may map to at least two ligands.

In still some other embodiments, the polypeptide may comprise at least three nonconsecutive sequence fragments of the first ligand of at least one residue.

In still some other embodiments, the fragments may be selected from a structurally conserved region common to the first ligand and the second ligand.

In still some other embodiments, at least one of the ligands may be a cytokine.

In still some other embodiments, at least one of the ligands may be a growth factor.

In still some other embodiments, at least one of the ligands may be a hormone.

In still some other embodiments, at least one of the ligands may be a pathogen ligand.

In still some other embodiments, the pathogen may be a eukaryotic pathogen.

In still some other embodiments, the pathogen may be a eubacterial pathogen.

In still some other embodiments, the pathogen may be a viral pathogen

In still some other embodiments, the first polypeptide may inhibit a first ligand-receptor complex and a second ligand-receptor complex.

In still some other embodiments, the first polypeptide may not inhibit a third ligand-receptor complex.

In still some other embodiments, a third ligand of the third ligand-receptor complex may be about as similar in sequence identity to the first ligand and about as similar in sequence identity to the second ligand as the first ligand is to the second ligand.

In still some other embodiments, the first ligand, the second ligand and a third ligand of the third ligand-receptor complex may be members of a common ligand family.

In still some other embodiments, the method may further comprise a second polypeptide sequence having an amino acid sequence comprising an at least a sequence fragment of a fourth ligand.

In still some other embodiments, the first polypeptide sequence and the second polypeptide sequence may be tethered to one another.

In still some other embodiments, the first polypeptide sequence and the second polypeptide sequence may be covalently bound to one another.

In still some other embodiments, the first polypeptide sequence and the second polypeptide sequence may be covalently bound to a polypeptide linker to form a single polypeptide comprising the first polypeptide sequence and the second polypeptide sequence and the linker polypeptide sequence.

In still some other embodiments, the first polypeptide sequence and the second polypeptide sequence may be covalently bound directly to one another without an intervening polypeptide linker to form a single polypeptide comprising the first polypeptide sequence and the second polypeptide sequence.

In still some other embodiments, the first polypeptide sequence and the second polypeptide sequence may not be covalently bound to one another.

In still some other embodiments, the first polypeptide sequence and the second polypeptide sequence may be tethered by a hydrophobic linker.

In still some other embodiments, the first polypeptide sequence and the second polypeptide sequence may be bound to one another by a linker comprising PEG.

In still some other embodiments, the polypeptide may inhibit a fourth ligand-receptor complex.

In still some other embodiments, the composition may be for use in specifically inhibiting multiple ligand-receptor complexes in a mammalian cell.

In still some other embodiments, non-targeted ligand-receptor complexes may not be affected by the composition.

In still some other embodiments, the multiple ligand-receptor complexes may be implicated in a disease.

In some other aspect, the disclosures provided herein relates to a method of designing an antagonist polypeptide against a family of cytokines that bind to a common receptor, such that binding of only a subset of the family of cytokines to the common receptor is selectively inhibited by the antagonist polypeptide, the method comprising obtaining amino-acid sequences of the subset of the family of cytokines, identifying from the amino acid sequences of the subset, receptor binding sites or amino acids involved in binding of the subset, or both, and designing a composite polypeptide sequence that comprises at least part of the identified receptor binding sites or the amino acids involved in binding of the subset, or both, wherein each of the identified receptor binding sites or the amino acids involved in binding of the subset, or both comprises a gamma c-subunit.

In still some other aspect, the disclosures provided herein relates to a method of designing a first inhibitor polypeptide of a first ligand-receptor complex and a second ligand receptor complex, comprising the steps of obtaining the polypeptide sequence of a first ligand, obtaining the polypeptide sequence of a second ligand, identifying a structurally conserved region common to the first ligand and the second ligand, wherein the region of the first ligand interacts with a receptor of the first ligand, and the region of the second ligand interacts with a receptor of the second ligand, and composing a chimeric polypeptide sequence comprising the structurally conserved region, the chimeric polypeptide having a sequence comprising sequence fragments of the first ligand and the second ligand, wherein a polypeptide comprising the chimeric polypeptide sequence selectively inhibits a first ligand-receptor complex of the first ligand and a second ligand-receptor complex of the second ligand, and wherein the structurally conserved region comprises a gamma c-subunit.

In some embodiments, the polypeptide does not inhibit a third ligand-receptor complex of a third ligand.

In some other embodiments, the third ligand comprises a polypeptide sequence that is not substantially more different from the first ligand or from the second ligand than the first ligand is from the second ligand.

In still some other embodiments, the first ligand-receptor complex and the second ligand-receptor complex comprise a common receptor component.

In still some other embodiments, the first ligand-receptor complex, the second ligand-receptor complex and the third ligand-receptor complex comprise a common receptor component.

In still some other embodiments, each of the sequence fragments is fewer than 11 residues.

In still some other embodiments, the chimeric polypeptide comprises at least three sequence fragments of the first ligand.

In still some other embodiments, each of the sequence fragments uniquely maps to a single ligand.

In still some other embodiments, at least one of the sequence fragments maps to at least two ligands.

In still some other embodiments, the first ligand is selected from the group consisting of a chemokine, a hormone, a growth factor, and a cytokine.

In still some other embodiments, the structurally conserved region comprises a D helix In still some other embodiments, each of the first ligand, the second ligand, and the third ligand is independently selected from the list consisting of IL-2, IL-4, IL-7, IL-9, IL-15 or IL-21.

In still some other embodiments, the first ligand is a pathogen ligand.

In still some other embodiments, the pathogen is selected from the group consisting of a virus, an *eubacterium*, and an eukaryote.

BRIEF DESCRIPTION OF THE DRAWINGS

FIG. 1A shows an alignment of the D-helix region of human γc-cytokine family members.

FIG. 1B depicts the γc-box and IL-2/IL-15 box motifs which give rise to the consensus sequence around the D-helix region of the γc-cytokines.

FIGS. 8A-8C present conservation at the primary structure level of the D-helices from γc-cytokines. FIG. 8A depicts alignment of amino acid sequences of the six human γc cytokines at helix D. FIG. 8B depicts IL-2/15 box which is an extended homologous region between IL-2 and IL-15 at the C-terminus. FIG. 8C depicts the sequence of BNZ132-1 peptide. Amino acid sequences of the human γc-cytokines have been aligned using the T-coffee algorism. A region with moderate conservation (identical aa or conservative substitutions) was named as the γc-Box. FIG. 8B presents alignment of human IL-2 and IL-15. Between IL-2 and IL-15, we identified another conserved region to the C-terminus of the γc-Box. This region is named the IL-2/15 box. FIG. 8C presents design of the BNZ 132-1 peptide.

FIGS. 9A, 9B, and 9C depict rational evolution of γc-inhibitory peptide sequence leading to BNZ132-1. FIGS. 9D-9H depict 3D rendition of the computer-assisted docking results involving candidate peptides and human γc-molecule. FIGS. 9A, 9B, and 9C present construction logic behind the design of BNZ132-1. The 19 aa (amino acid)-BNZ132-1 peptide was designed based on the following logic.

Figure 2:
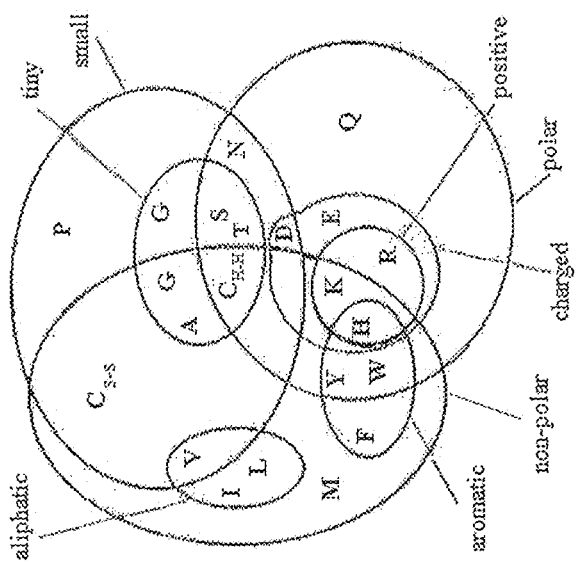
FIG. 2 depicts a diagramed representation of the biochemical properties of amino acids.

Fixed positions from binding chemistry (emphasized with bold texts):

Gln13, Ile16—identical binding residues between human IL-2 and IL-15

Gln6—this position participates in the binding only in IL-2, but not with IL-15. Fixing it with Asn (IL-2 specific residue) may add IL-2-biased characteristic to the peptide. Therefore, Gln was adopted from the IL-15 sequence, but this should have neutral effect on the binding of the peptide to γc.

Fixed positions from shared amino acid usages (emphasized with shading only): Ile1, Glu3, Phe 4, Leu5, Thr18—these residues do not participate directly in the binding between cytokines' D-helices and the γc-molecule. However, these amino acids were conserved between human IL-2 and IL-15.

Fixed positions from favored amino acid usages across mammalian species: Ile9—Although human IL-15 has Val at this position, murine IL-15 and most mammalian IL-2 has I at this position. Ile11—similar to Ile9, except that mouse IL-2 and mammalian IL-15 use Ile at this position. Ser19—Many mammalian IL-15 and rat IL-2 use Ser at this position.

High priority "Wobble" positions from binding chemistry: His10 or Thr10, Met14 or Ser14, Asn17 or Ser17—these amino acids in either cytokine are in contact with the surface of the γc-molecule. We have tested combining two from one cytokine and the last from the other cytokine. In other words, these three positions were designed with a linkage to each other. Three out of IL-2 or three out of IL-15 for these positions might cause structural bias and thus have been eliminated.

Low priority "Wobble" positions: 2, 7, 8, 12, 15 As the positions that have been fixed based on the logic shown above could introduce bias either to IL-2 or IL-15 sequence, these low-priority positions could provide leverage. However, these five positions have weaker impact on the binding chemistry, and thus we did not seek for a perfect counterbalance from these positions. For example, if His10, Met14 have been chosen from IL-15 and Ser17 from IL-2, then we allowed either three from IL-2+ two from IL-15, or two from IL-2+ three from IL-15 at these five positions. The selection logic described above gave rise to total 120(=20×6) amino acids (Table 1) which have been tested by a computer simulation program (Pep-Fold) if the candidate sequence would form thermodynamically stable complex with the γc-molecule in a geometry similar to that used by the binding of γc-cytokines and γc. Finally, 39 candidate peptides were chosen for peptide synthesis, and each of them was biologically tested using CTLL-2 cells if IL-2 and IL-15 activities (induction of proliferation) were equally neutralized by the peptide.

FIGS. 9D-9H presents 3D rendition of the computer-assisted docking results involving candidate peptides and human γc-molecule. Sequential computer docking simulations (Pep-Fold, Patch-Dock, and Fire-Dock) gave rise to thermodynamical evaluation and 3-dimensional geometry of the potential dockings. The representative results were divided into two categories—those that bind to the distant side of γc, opposite from that of γc and some γc-cytokines such as IL-2 or IL-15 (similar structural analyses of receptor-cytokine complex involving IL-7, IL-9, or IL-21 have not been published yet) and those that bind near to the γc/cytokine (in particular, D-helix of the cytokine) interface. We called the peptide candidates that show binding geometry described in the former example as "non-competitive" peptides and the latter as "competitive" binding. Thirty nine peptides including 033 (later designated as BNZ132-1) show competitive binding to the γc. Curiously, if only the D-helix from IL-2 or IL-15 was tested by the similar binding algorism, they did not overlap with the position of the D-helix in the entire cytokine bound to the γc-molecule and hence no "displacement" was observed (D-helix from IL-15, D-helix from IL-2). These results may imply that the location of binding interface of γc may be significantly controlled by the interaction between the cytokine and the private chain. This insight may be a strong influence on our strategy to develop BNZ132-1 as a clinical drug.

FIG. 10A depicts results of a CTLL2 proliferation assay. FIG. 10B depicts results of a PT18 proliferation assay. FIG. 10C depicts results of an apoptosis assay by Annexin V staining. FIG. 10D depicts results of a Human peripheral T-cell proliferation assay. FIG. 10E depicts results of a PT-18 proliferation assay in response to non-γc cytokines. FIGS. 10A-10E presents inhibitory spectrum of BNZ132-1 over γc- and non-γc-cytokines. FIG. 10A presents inhibition of IL-2 and IL-15 by BNZ132-1 where CTLL-2 proliferation assay CTLL-2 has been incubated with 1 nM of human IL-2 or human IL-15 (Peprotech), in the presence of indicated concentrations (μM) of BNZ132-1 peptide. Neutralizing antibodies against each cytokine (R & D systems, 5 μg $ml^{-1}$) were included as controls. After 20 h, the cells were pulsed with WST-1 (Clontech) and OD450 of each well was measured after 6 h. A 19-mer scrambled peptide was used as a negative control at 5 μM. The experiments were conducted in triplicate (applies to all experiments in FIGS. 10A-10E). The result represents one of at least three independent experiments (applies to all experiments in FIGS. 10A-10E). FIG. 10B presents inhibition of IL-9, but not of IL-4 by BNZ132-1. In PT-18 proliferation assay, PT-1813 or PT-18h21Rα cells were withdrawn of mouse IL-3 for 12 h before the experiment. Cells were then incubated with 1 nM of mouse IL-4, mouse IL-9, or mouse IL-21 in the presence or absence of the indicated doses (μM) of BNZ132-1. Neutralizing antibodies to each cytokine (5 μg $ml^{-1}$, except for anti-mouse IL-21 polyclonal antibody which was used at 15 μg $mL_{-1}$) and a scrambled control peptide (5 μM) were included as negative controls. WST-1 assay was conducted as described above. FIG. 10C presents no inhibition of IL-21 by BNZ132-1. In PT-18 h21Rα survival assay, PT-18h21Rα cells are described in the text. They do not respond robustly to human IL-21 in proliferation (FIG. 10B). Both parental and hIL-21Rα positive PT-18 cells were washed and incubated without IL-3 for 12 h before the assay. 1 nM of human IL-21 (Peprotech) was added in the presence or absence of 5 μM BNZ132-1 or control peptide (scrambled) and cells were stained by PE-Annexin V (BD Biosciences) to determine the occurrence of apoptotic cell death by flow cytometry. Only hIL21Rα transfected, but not the parental PT-18 cells showed survival by human IL-21 (*; p=0.001), which was not blocked by BNZ132-1 (; p=0.48). FIG. 10D present no inhibition of IL-7 by BNZ132-1. In human PBMC proliferation assay, ex vivo T cells were prepared from human PBMC as described in the methodology section. IL-2 was withdrawn from the culture 12 h prior to the assay. Cells were incubated with 10 nM human IL-7 (Gemini) for 24 h in the presence or absence of indicated amount (μM) of BNZ132-1. As positive controls, 1 nM of human IL-2 and 1 nM human IL-15 (Peprotech) were used. As negative controls, neutralizing antibodies (5 $\mu g ml^{-1}$) against each cytokine and a control scrambled peptide (5 μM) were included. WST-1 proliferation assay was conducted as described above. FIG. 10**E presents no inhibition of non-γc cytokines by BNZ132-1. In PT-18 proliferation assay, PT-18β (subclone with human IL-2/IL-15Rβ, CD122 transfected) cells were depleted of IL-3 for 12 h prior to the assay. One nanomolar of indicated cytokines (human IL-15, mouse IL-3, mouse GM-CSF, mouse stem cell factor, and human Flt-3 ligand) were added to the fasted PT-18β for 20 h with or without 15 μM BNZ132-1, and then pulsed with 1 μCi of 3H-thymidine (GE-Health) to determine the cellular incorporation. Neutralizing antibodies (5 $\mu g ml^{-1}$, except the one for mSCF which was used at 20 $\mu g ml^{-1}$) to each cytokine and a control peptide (scrambled) were included as controls. The Y-axis represents the cpm (count per minute) values measured by a β-counter.

FIG. 11A depicts the proliferation results from a MTT assay. FIG. 11B depicts results illustrating effective inhibition of the ex vivo proliferation of HAM/TSP T cells by BNZ132-1. FIGS. 11A and 11B present effective inhibition of a combined function of target γc-cytokines by BNZ132-1. FIG. 11A presents combinatorial effect of IL-2 and IL-15 was effectively inhibited by BNZ132-1 in human peripheral T cells. Human Peripheral T cells were prepared as described in the methodology section. Four hundred thousand cells (in 200 μl culture) were incubated with the cytokines and BNZ132-1 at the indicated concentrations for 24 h, and cellular proliferation was determined by the MTT method using the WST-1 reagent (Clontech). The Y-axis represents the OD450 values. The p values; 1 nM cytokine combination—No inhibition vs. anti-IL-2; 0.33, No inhibition vs. anti-IL-15; 0.13, No inhibition vs. anti IL-2+IL-15; 0.003. No inhibition vs. BNZ132-1; 0.021. 0.1 nM cytokine combination—No inhibition vs. anti-IL-2; 0.046, No inhibition vs. anti-IL-15; 0.057, No inhibition vs. anti IL-2+IL-15; 0.001, No inhibition vs. anti IL-2+15; 0.001, No inhibition vs. BNZ132-1; 0.001. The assay was performed in triplicate. FIG. 11B presents translational potential of BNZ132-1 for HAM-TSP—Efficient inhibition of the spontaneous activation of HAM-TSP T cells (from a patient) by BNZ132-1 as good as the combined anti-IL-2 and anti-IL-15 antibodies. Peripheral blood mononuclear cells were purified from the blood of a HAM-TSP patient and set up for a spontaneous proliferation assay as previously described 36. The cellular proliferation was measured by the thymidine incorporation assay. The Y-axis represents the cpm values. Doses are on the X-axis; BNZ132-1, 3 and 0.3 µM. Antibodies against IL-2 or IL-15 (1 and 10 µg ml-1 of each, R & D Systems). The p values; between no treatment and BNZ132-1(0.3): 0.018, between no treatment and BNZ132-1 (3): 0.0018, between BNZ132-1 (3) and Anti IL-2+IL-15 (10): 0.29

Figure 12A:
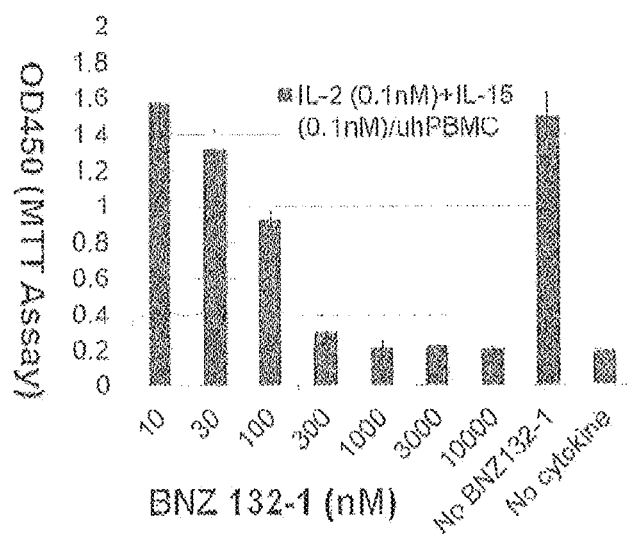
Figure 12B:
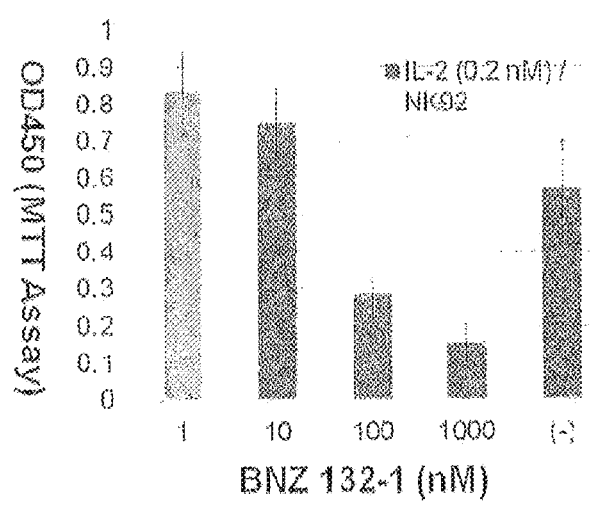
Figure 12C:
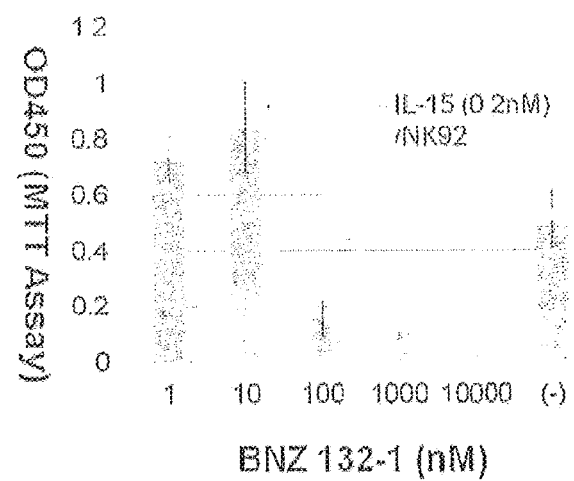

FIGS. 12A, 12B and 12C depict results from proliferation studies using MTT assays. FIG. 12A presents dose-dependent co-inhibition of human IL-2 and IL-15 in human Peripheral T cells by BNZ132-1. Human peripheral blood mononuclear cells were purified by the Ficoll-paque gradient centrifugation (GE-Healthcare) and stimulated by PHA (5 µg ml$^{-1}$, Sigma) for 48 h, then expanded with IL-2 (0.5 nM, Peprotech) for 48 h, and then depleted of non-T cells by the Pan-T cell negative enrichment Ab cocktails (Miltenyi). The purified T cells were then fasted of IL-2 overnight prior to the proliferation assay by the tetrazolium dye method. Four hundred thousand cells (in 200 µl culture) were incubated with the cytokines and BNZ132-1 at the indicated concentrations for 24 h, and 20 µl WST1 reagent (Clontech) was added to each well. After 12 h incubation, OD450 was measured. The assay was performed in triplicate. FIGS. 12B and 12C present dose-dependent inhibition of human IL-2, IL-15 and IL-9 in NK92 cells by BNZ132-1. NK 92 cells were cultured in human IL-2. Cells were washed to withdraw IL-2 for overnight and two hundred thousand cells (in 200 µl volume) were incubated with the indicated concentrations of the cytokine and BNZ132-1 for 24 h before 20 µl WST-1 reagent (Clontech) was added to each well to measure proliferative response. Absorbance at 450 nm was read at 6 h after the addition of the WST-1 dye. The assay was performed in triplicate. The assay was performed in triplicate and the figure represents a typical result out of 5 different HAM-TSP patients.

FIGS. 13A, 13B, and 13C depict results illustrating inhibition of signal transductions pathways downstream of IL-15/IL-15 receptor system in PT-18 and ex vivo human T-cells by BNZ 132-1. FIGS. 13A-13C present comprehensive inhibition by BN132-1 of signaling events caused by target γc-cytokines. FIG. 13A presents near-complete inhibition of IL-15 signaling in PT-18β by BNZ132-1 PT-18β is a subclone33 of the parental PT-1832. Cells have been fasted of IL-3 for 12 h and then stimulated with 1 nM human IL-15 (Peprotech) in the presence or absence of 0.5 µM BNZ132-1 for 15 min before extraction of cellular proteins. Phosphorylation of the relevant molecules were detected using antibodies against each phosphor-proteins (Cell Signaling), followed by the ECL technique (Thermo Scientific). Lanes: 1. no stimulation, 2. IL-15(1 nM), 3. IL-15 (1 nM)+ BNZ132-1 (0.5 µM). FIG. 13B presents signal transduction of IL-4 in PT-18 was not inhibited whereas the IL-9 signal was inhibited by BNZ132-1.

PT-18 cells 32 were fasted of IL-3 for 12 h prior to stimulation. Cells were stimulated with 1 nM mouse IL-4 or mouse IL-9 in the presence or absence of excess dose of BNZ132-1 (5 µM) for 15 min and then cellular proteins were extracted. Phosphorylation of the indicated proteins was detected using phosphor-specific antibodies (Cell signaling), followed by ECL. IL-4 is the only γccytokine that induces the phosphorylation of STAT6. Note that only IL-4, but not IL-9, induced the tyrosine-phosphorylation of STAT6. Conversely, IL-4 showed only marginal phosphorylation of STAT5 whereas IL-9 induced a strong phosphorylation of STAT5. Lanes: 1. no stimulation, 2. IL-4, 3. IL-4+BNZ132-1, 4. IL-9, 5. IL-9+BNZ132-1

FIG. 13C presents IL-2 signal in human PBMC was blocked by BNZ132-1. Human PBMCs were prepared (Ficoll-paque), activated (by PHA) expanded (by IL-2), and purified by magnetic negative selection as described in the methodology section. After 24 h of IL-2 depletion, the PBMCs were stimulated by 1 nM IL-2 in the presence or absence of BNZ132-1 (0.5 or 0.1 µM) for 20 min before the cellular protein extraction. Phosphorylation of individual proteins was visualized by phosphor-specific antibodies (Cell Signaling), followed by ECL. Lanes: 1. no stimulation, 2. IL-2 stimulation, 3. IL-2+BNZ132-1 (high dose), 4. IL-2+BNZ132-1 (low dose). In all blots, anti-Vinculin antibody (Sigma) was used to validate nearly-equal protein loading.

Figure 14C:
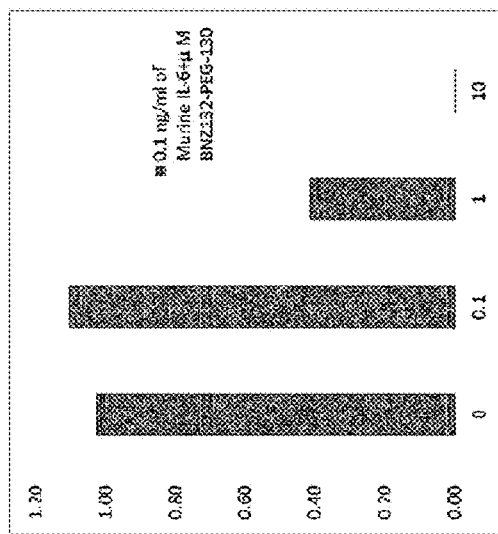
Figure 14B:
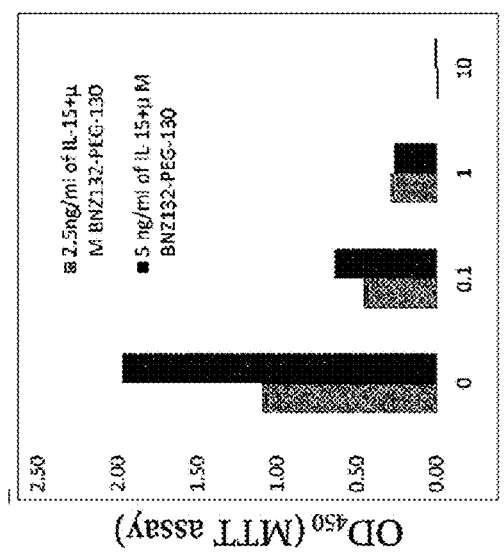
Figure 14A:
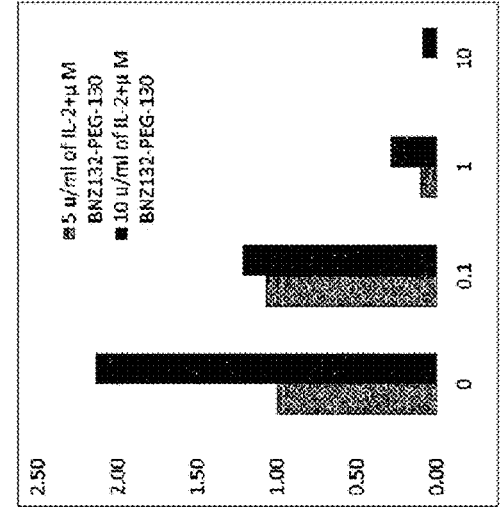

FIGS. 14A, 14B, and 14C depicts results from CTLL2 proliferation assays using MTT assay. FIGS. 14A, 14B, and 14C present proliferation in CTLL2 and T1165 cell lines are inhibited in a dose response manner by a dual functioning peptide. CTLL2 cells are cultured in the presence of 5 u/ml and 10 u/ml of IL-2 (A) and 2.5 ng/ml and 5 ng/ml of IL-15 (B) in the presence of increasing concentration of BNZ132-PEG-130. T1165 cells are cultured with 0.1 ng/ml of IL-6 and increasing concentration of BNZ132-PEG-130.

Figure 15:
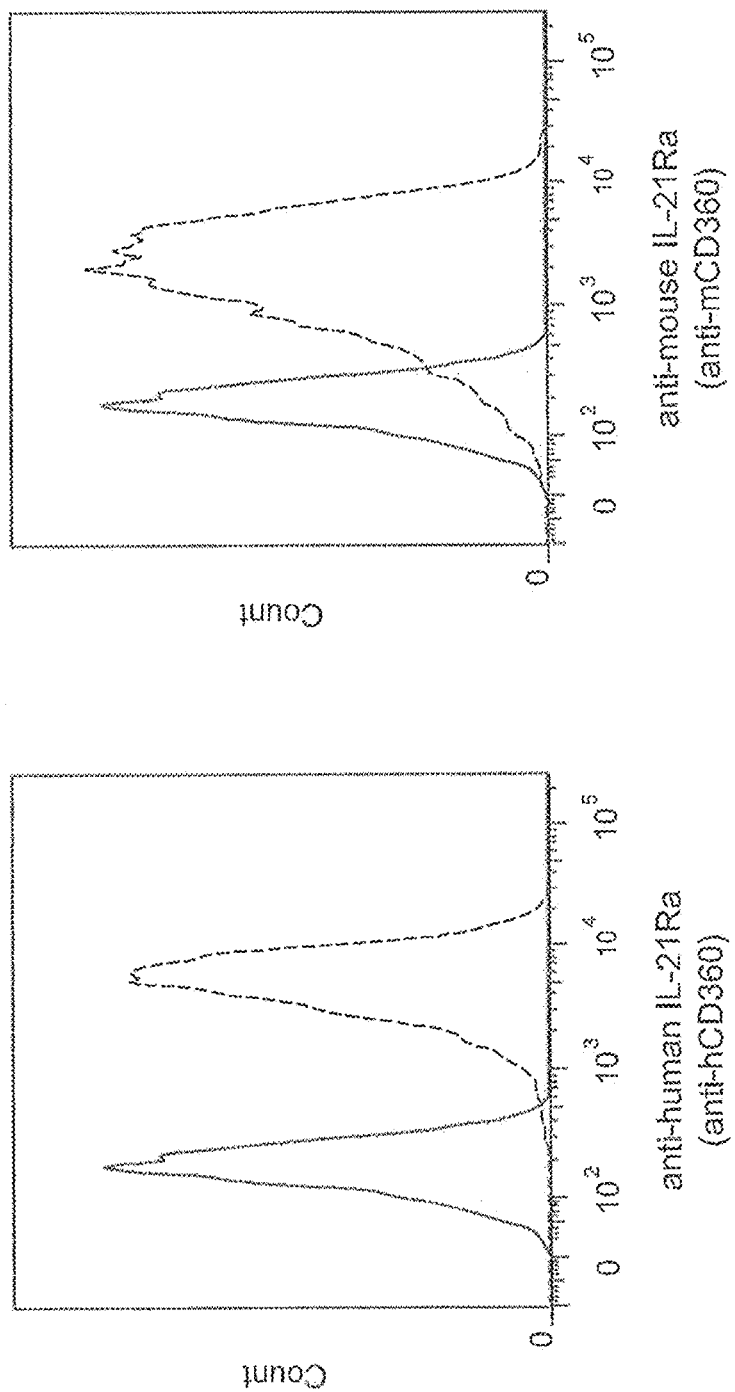

FIG. 15 depicts results illustrating IL-21Rα expression profiles of engineered PT-18 cells. FIG. 15 presents establishment of PT18 subclones that express human IL7Rα or human IL7Rα+ human γc. In an attempt to generate IL-7 responding PT-18 subclones, human IL-7Rα cDNA was amplified by RT-PCR using cDNAs synthesized from human PBMC, subcloned into the pEF-Neo expression vector and was transfected into PT-18 cells by electroporation (see above). After the G418 selection, the surviving cells were stained by an antibody to IL-7Rα (CD127, Biolegend clone A019D5), and sorted by a single cell per well in 96-well culture plates. The expanded clones were verified by the same antibody. As shown in this figure (B, blue line), the hIL-7Rα positive PT-18 clones failed to show proliferative response (or survival response, data not shown) to human recombinant IL-7 (Peprotech), as examined by the tetrazorium dye assay (using WST-1, Clontech). The Y-axis of the figure represents OD450. To test if both human IL-7Rα and human γc are required to render mouse PT-18 cells to respond to human IL-7, the human IL-7Rα-positive PT-18 cells were additionally transfected with human γc-cDNA in the pEF-Neo vector and the cells were sorted multiple times after staining with a monoclonal antibody recognizing human γc (Biolegend, clone TUGH4). The upper right histogram demonstrates the expression levels of endogenous mouse γc on the parental PT18 cell line (red line; isotype control, blue line; PE-antibody against mouse γc, BD Biosciences clone TUGm2). As shown in FIG. 16B (red line), these subclone of PT-18 responded to human IL-7 (Peprotech) as determined by the WST-1 assay.

Figure 16:
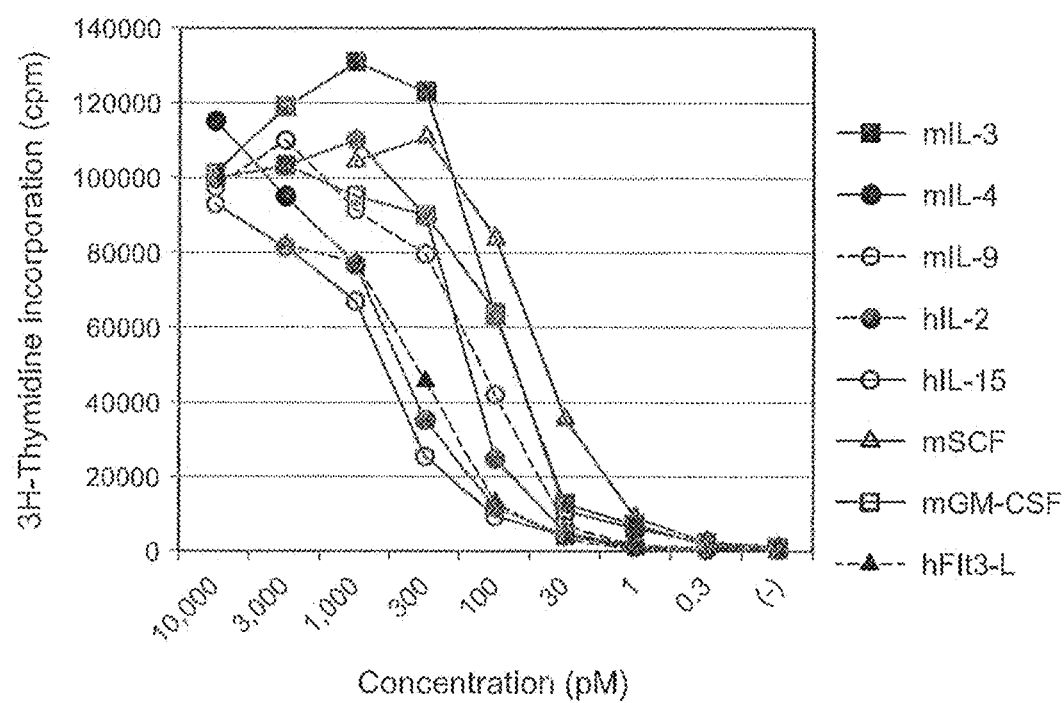

FIG. 16 depicts results illustrating response of PT-18 and its subclones to various cytokines. FIG. 16 presents response of PT-18 and its subclones to various cytokines. PT-18 is a mouse mast cell line 53. Among the γc-cytokines, the parental cell line responds to mouse IL-4 (not human IL-4), mouse IL-9 (not human IL-9). They did not respond to IL-2 and IL-15 due to the lack of IL-2/IL-15Rβ (CD122), not to IL-7 or IL-21 due to the lack of private α chains. We have transfected the human IL-2/IL-15Rβ (CD122) to establish subclones that respond to human IL-2, and human IL-1554. Shown in FIG. 16 is the detailed dose-response of this subclone (PT-18β54) to various γc- and non-γc-cytokines. PT-18 cells are maintained with mouse IL-3 supplement (5% vol/vol, conditioned medium from a NIH-3T3 cells transfected with human IL-3 cDNA in our lab). Before the proliferation assay, cells are washed in PBS, then resuspended in IL-3-free culture media (with 10% (vol/vol) FBS) for 12 h to deplete the growth-promoting/anti-death effect of IL-3. At the completion of this fasting, the viability of the cells is usually >95%, but the cells lose blastoid morphology. Addition of growth-promoting cytokines quickly restores the active growth signal transduction, and causes cell division in 16-24 h. The response was measured by plating PT-18 cells at 5×105 cells ml-1 in 200 µl culture media containing the growth factor in 96-well plates, incubating for 20 h, then adding 1 µCi of 3H-Thymidine for 4 h before harvesting the plate. The incorporation of radioactive thymidine was measured by a β-counter. The assay was set up in triplicate.

Figure 17A:
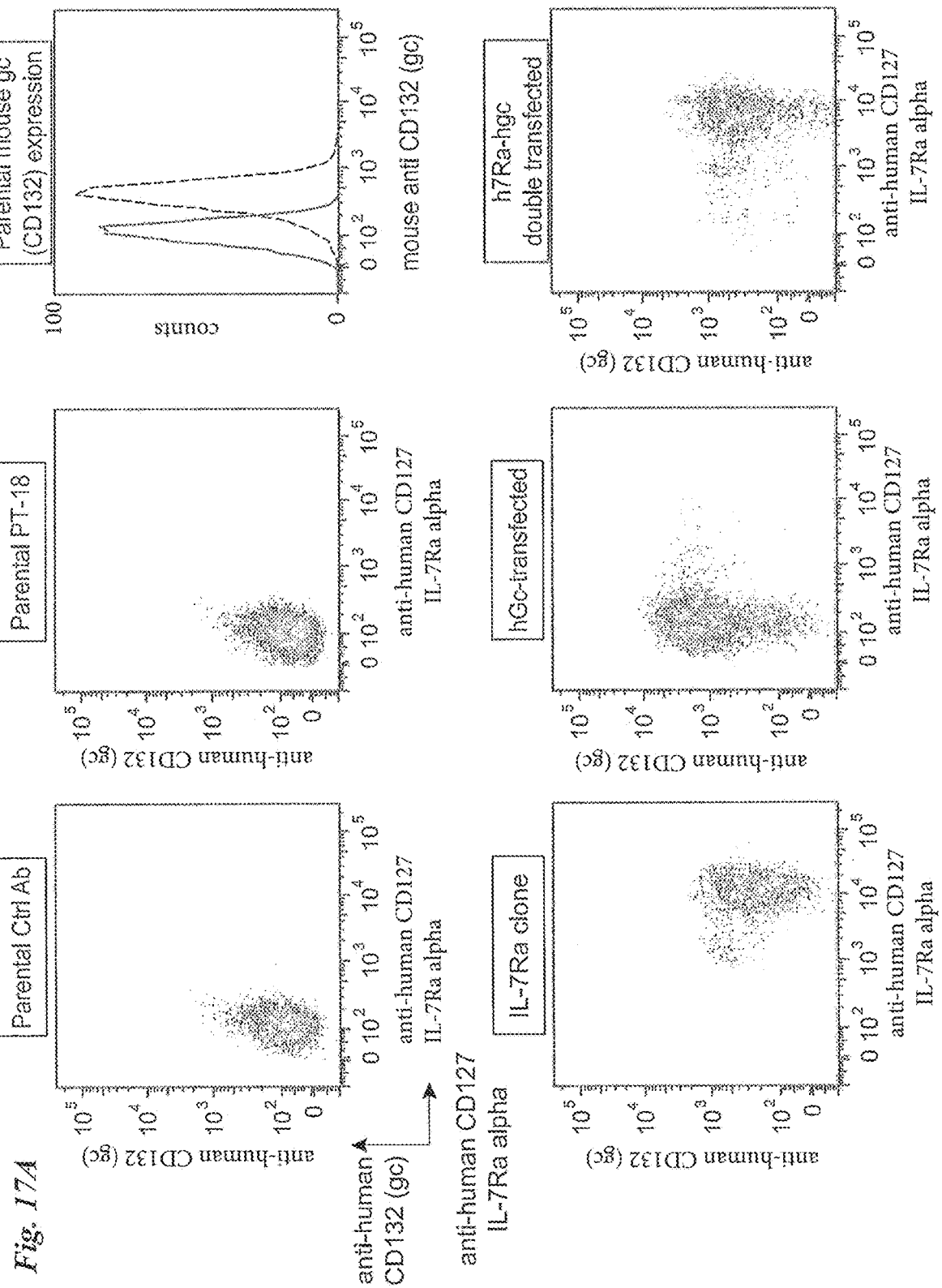
Figure 17B:
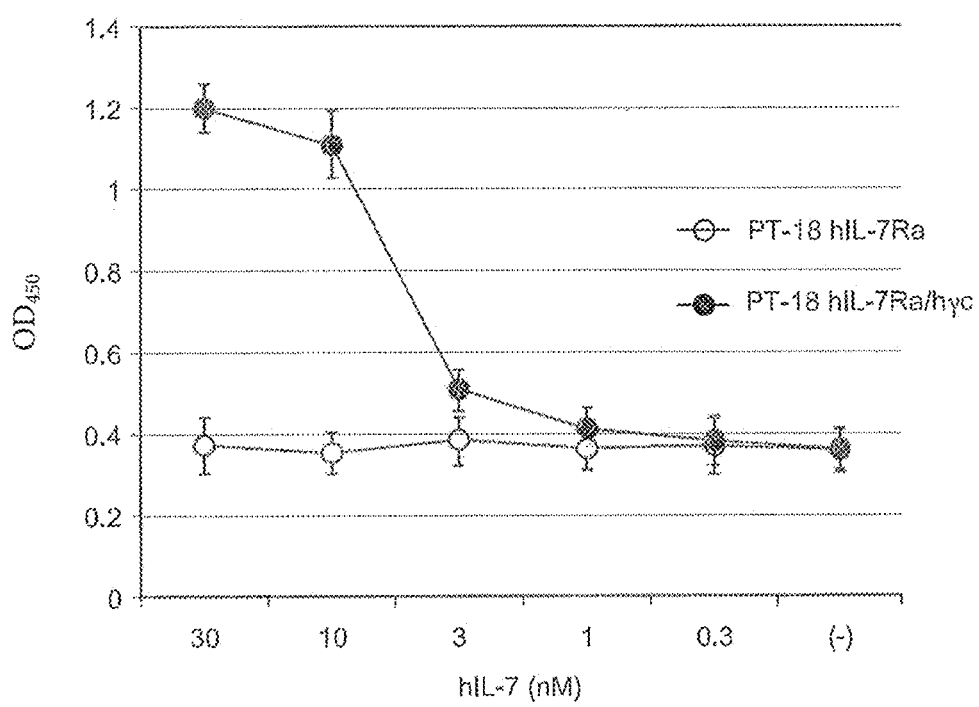

FIGS. 17A and 17B depicts results illustrating establishment of PT18 subclones that express human IL7Rα or human IL7Rα+ human γc. FIG. 17A presents establishment of PT18 subclones that express human IL7Rα or human IL7Rα+ human γc. In an attempt to generate IL-7 responding PT-18 subclones, human IL7Rα cDNA was amplified by RT-PCR using cDNAs synthesized from human PBMC, subcloned into the pEF-Neo expression vector and was transfected into PT-18 cells by electroporation (see above). After the G418 selection, the surviving cells were stained by an antibody to IL-7Rα (CD127, Biolegend clone A019D5), and sorted by a single cell per well in 96-well culture plates. The expanded clones were verified by the same antibody. As shown in this figure (B, blue line), the hIL-7Rα positive PT-18 clones failed to show proliferative response (or survival response, data not shown) to human recombinant IL-7 (Peprotech), as examined by the tetrazorium dye assay (using WST-1, Clontech). The Y-axis of FIG. 17B represents OD450. To test if both human IL-7Rα and human γc are required to render mouse PT-18 cells to respond to human IL-7, the human IL-7Rα-positive PT-18 cells were additionally transfected with human γc-cDNA in the pEF-Neo vector and the cells were sorted multiple times after staining with a monoclonal antibody recognizing human γc (Biolegend, clone TUGH4). The upper right histogram demonstrates the expression levels of endogenous mouse γc on the parental PT18 cell line (red line; isotype control, blue line; PE-antibody against mouse γc, BD Biosciences clone TUGm2). As shown in FIG. 17B (red line), these subclone of PT-18 responded to human IL-7 (Peprotech) as determined by the WST-1 assay.

DETAILED DESCRIPTION OF THE TABLES

The following provides further detailed descriptions of the tables presented herein.

Table 1 presents a list of human diseases that pathologically involve multiple γc-cytokines. The table indicates examples of human diseases that involve multiple γc-cytokines. For simplicity of the logic, involvement of non-γc cytokines is how shown included unless they are shown to be crucial for the pathogenesis (e.g., IL-6 in RA and IL-13 and -5 in Asthma, shown in red).

Table 2 presents homology of IL-2 from various mammalian species at each of the four helices. The amino acid (aa) sequences of IL-2 from various species (Cynomolgus monkey, human, mouse and cow) were aligned using the T-coffee algorism at the aa level. In general, mouse IL-2, among the 3 species, shows minimum homology to the human IL-2 (to the point that there is almost no homology and negligible similarity conserved at the C-helix). In the D-helix, even mouse IL-2 shows approximately 50% homology to the human counterpart, suggesting that this region might have special functional importance to IL-2.

Table 3 presents homology in the D-helix region of six human cytokines belonging to the γc-family. In order to evaluate the relevance of the D-helix in the γc-family, six human γc-cytokines were aligned using the T-coffee algorism. Apparently the homology is not extremely high, but the D-helix, among the four helices, shows the highest homology score. As described above, this is consistent with a previous structural studies that the D-helix of the three γccytokines functions as the primary binding moiety to the γc molecule, It is of note that only IL-2, -4, and 15 have been structurally resolved in the context of hetero-multimeric receptor complex involving the γc-molecule. In order to evaluate the relevance of the D-helix in the γc-family, six human γc-cytokines were aligned using the T-coffee algorism. Apparently the homology is not extremely high, but the D-helix, among the four helices, shows the highest homology score. As described above, this is consistent with a previous structural studies that the D-helix of the three γc-cytokines functions as the primary binding moiety to the γc molecule, It is of note that only IL-2, -4, and 15 have been structurally resolved in the context of hetero-multimeric receptor complex involving the γc-molecule.

Table 4 presents provisional library of compounds that comprehensively inhibit any possible combinations of the 6 γc-cytokines that could occur in human diseases. The expansion of our current concept may have useful clinical ramifications. The γc-family is a mathematical group of 6 members. There exist 63 subsets (6C6+6C5+6C4+6C3+6C2+6C1=63) that consist of differential combinations of all 6 members. Such library would enable to treat any human diseases which pathogenically involve combinations of γc cytokines. For example, BNZ132-1, -2 and -3 (the sequences of BNZ132-2 and -3 are not disclosed in this paper) have distinct target cytokine spectrums. BNZ132-1, as shown in the text, specifically inhibits IL-2, IL-15 and IL-9. BNZ132-2 inhibits IL-15 and IL-21 (data not shown) and can be a candidate for treating Celiac disease (8-14). BNZ132-3, which inhibits IL-4 and IL-9 (data not shown), can be a novel treatment compound for Asthma.

DETAILED DESCRIPTION

Overview

The γc-cytokines are important players in the development of the lymphoid cells that constitute the immune system, particularly T, B, and NK cells. Further, γc-cytokines have been implicated in various human diseases. Thus, factors that inhibit γc-cytokine activity would provide useful tools to elucidate the developmental mechanism of subsets of lymphocytes and to treat immune disorders and γc-cytokine-mediated diseases.

Germ line depletion of the genes encoding the γc-subunit in mice or mutations of γc-subunit in humans are known to cause severe combine immunodeficiency (SCID) by disrupting the normal appearance or function of NK, T, and B cells. The importance of the γc-subunit in the signal transduction of the γc-cytokines, IL-2, -4, -7, -9, 15, -21, is indicated in studies demonstrating the a of response of lymphocytes from these mice and human patients to the γc-cytokines (reviewed in Sugamura et al., 1995 Adv. Immunol. 59:225-277). This indicates that disruption of the interaction between the γc-subunit and a γc-cytokine would efficiently block the intracellular signaling events by the γc-cytokine family members. Therefore antagonist peptides according to the present embodiments are expected to effectively block the pathogenic changes in humans suffering from the diseases mediated by misregulation of the γc-cytokine family members.

As an alternative to antibody-mediated approaches for modulating the activity of individual γc-cytokines, Applicants have devised novel, low molecular weight compounds herein referred to as "Simul-Block", which suppress the activity of multiple γc-cytokines. These low molecular weight compounds, which include both chemicals and peptides, are less immunogenic than antibodies. These properties distinguish Simul-Block as a more efficient strategy for mediating γc-cytokine activity in clinical interventions.

Discovery of the γc-Box

The C-terminus (the D-helix) of the γc-cytokines contains the proposed site for interacting with the common γc-subunit of the multi-unit cytokine receptors. (Bernard et al., 2004 J. Biol. Chem. 279:24313-21.) Comparison of the biochemical properties of the amino acids of all γc-cytokines identified in mice and humans revealed that the chemical nature of the amino acids, for example, hydrophobicity, hydrophilicity, base/acidic nature, are conserved, if not identical, at many positions in the D-helix across the members of the γc-cytokine family. In contrast, the sequence of IL-13, which is related to the γc-cytokine, IL-4, but does not bind to the γc-subunit, does not exhibit significant homology in the D-helix region to the γc-cytokines, suggesting that the sequence homology in the D-helix region is correlated with binding to the γc-subunit. As shown in FIGS. 1A and 1B, alignment of the amino acid sequences of the D-helix region of γc-cytokine family members in humans reveals a motif of moderate sequence homology in these cytokines referred to herein as "the γc-box".

The γc-box comprises 19 amino acids where out of the 19 positions, positions 4, 5, and 13 are fully conserved as Phenylalanine, Leucine, and Asparagine, respectively. Less conservation is observed at positions 6, 7 and 11 of the γc-box where the amino acid is one of two or three related amino acids that share physico-chemical properties: position 6 may be occupied by the polar amino acids Glutamate, Asparagine or Glutamine; non-polar amino acids Serine or Arginine can occupy position 7; and position 11 is occupied by either of the non-polar aliphatic amino acids Leucine or Isoleucine. Positions 9 and 16 may be occupied by the either the non-polar amino acid Isoleucine or the polar amino acid Lysine. See FIG. 1B. Some differences in the amino acid composition of the γc-box are observed at positions 9 and 6 amongst subfamilies of the γc-cytokines. Comparison of the γc-cytokines across species indicates that Isoleucine is present at the 9 and 6 positions in the IL-2/15 subfamily, whereas the other γc-family members (e.g., IL-4, IL-21) possess Lysine in these positions. Not wishing to be bound by a particular theory, Isoleucine and Lysine are biochemically different and thus may impart specific conformational differences between the IL-2/15 subfamily and other γc-cytokines.

Conservation of the γc-box motif between γc-cytokines is supported by findings that an Asparagine (Asn, Q) residue located in the D-helix region is critical for the binding of the γc-cytokines to the γc-subunit. (Bernard et al., 2004 J. Biol. Chem. 279: 24313-21.)

Peptide Inhibitors of γc-Cytokine Activity

The activity of γc-family cytokines may be blocked by disrupting the interaction between the γc-cytokine and the γc-subunit, for example by introducing a competitive inhibitor which can interact with the γc-subunit without stimulating signaling through the multi-subunit cytokine receptors. Not to be bound by a particular theory, the conserved γc-box motif, which participates in binding of the γc-family cytokines to the γc-subunit, presents a core base amino acid sequence which can be utilized to design peptide inhibitors of γc-cytokine signaling.

The core γc-box amino acid sequence comprises: D/E-F-L-E/Q/N-S/R-X-I/K-X-L/I-X-Q (SEQ ID NO: 157) (where X denotes any amino acid). Embodiments described herein relate to custom peptide derivatives of the core γc-box amino acid sequence which can inhibit the activity of one or more γc-cytokines. Custom peptide derivatives include any peptide whose partial amino acid sequence shows approximately 50%, 50-60%, 60-70%, 70-80%, 80%, 90%, 95%, 97%, 98%, 99% or 99.8% identity to the core γc-box amino acid sequence. Custom peptide derivatives further include any peptide wherein a partial amino acid sequence of that peptide derivative comprises amino acids with similar physico-chemical properties to the amino acids of the core γc-box. For example, amino acids with similar physico-chemical properties would include Phenylalanine, Tyrosine, Tryptophan, and Histidine, which are aromatic amino acids. FIG. 2 shows a diagrammed representation of amino acids with similar physico-chemical properties which may be may be substituted for the amino acids comprising the core γc-box. Peptide derivatives of the core γc-box may be 11, 12, 13, 14, 15, 16, 17, 18, 19, 20, 21, 22, 24, 25-30, 30-35, 35-40, 40-45, 45-50, or more than 50 amino acids in length. In some embodiments, the custom peptide derivatives may be conjugated to the N-termini, C-termini and/or to the side residues of existing biological proteins/peptides.

Based on the identification of the conserved γc-box motif in cytokines which bind to the γc-subunit, Applicants have devised a novel, 19-mer custom derivative peptide which is an artificial composite peptide combining the amino acid sequence of the human IL-2 and IL-15 γc-box. The 19-mer peptide, herein referred to as BNZ-γ, consists of the amino acid sequence: I-K-E-F-L-Q-R-F-I-H-I-V-Q-S-I-I-N-T-S (SEQ ID NO: 34), where the amino acids depicted by bold characters are conserved between IL-2 and IL-15 and the underlined amino acids represent positions where the physico-chemical properties of the amino acids are conserved.

Applicants discovered that the 19-mer BNZ-γ, suppresses IL-15 and IL-9 induced cellular proliferation, but not IL-3 or IL-4 induced cellular proliferation. See FIG. 3A and Example 2. Applicants further demonstrated that BNZ-γ inhibits IL-15 mediated phosphorylation of the intracellular cytokine signal transduction molecule, STAT-5. See FIG. 3C and Example 5. These results demonstrate that custom peptide derivatives of the conserved γc-box motif can inhibit the activity of multiple γc-cytokines.

Several embodiments relate to custom derivative peptides of the 19-mer BNZ-γ amino acid sequence, I-K-E-F-L-Q-R-F-I-H-I-V-Q-S-I-I-N-T-S(SEQ ID NO: 34), which can inhibit the activity of one or more γc-cytokines. Custom peptide derivatives of the 19-mer BNZ-γ amino acid sequence include any peptide whose partial amino acid sequence shows approximately 50%, 50-60%, 60-70%, 70-80%, 80%, 90%, 95%, 97%, 98%, 99% or 99.8% identity to amino acid sequence: I-K-E-F-L-Q-R-F-I-H-I-V-Q-S-I-I-N-T-S(SEQ ID NO: 34). Custom peptide derivatives further include any peptide wherein a partial amino acid sequence of that peptide derivative comprises amino acids with similar physico-chemical properties to the amino acids of sequence: I-K-E-F-L-Q-R-F-I-H-I-V-Q-S-I-I-N-T-S(SEQ ID NO: 34). In several embodiments, the amino acid residues of the custom derivative peptides retain similar physico-chemical properties with the amino acid residues of BNZ-γ, but exhibit different biological inhibition specificity to the 6 γc-cytokine family members from that of the original 19-mer peptide. Peptide derivatives of BNZ-γ may be 19, 20, 21, 22, 24, 25-30, 30-35, 35-40, 40-45, 45-50, or more than 50 amino acids in length. In some embodiments, the custom peptide derivatives may be conjugated to the N-termini, C-termini and/or to the side residues of existing biological proteins/peptides.

Several embodiments relate to custom peptide derivatives of the γc-box motifs of IL-15, IL-2, IL-21, IL-4, IL-9, or IL-7, which are depicted in FIG. 1A. Other embodiments relate to custom derivative peptides which are artificial composite peptides combining the amino acid sequence of two or more of the human IL-15, IL-2, IL-21, IL-4, IL-9, and IL-7 γc-box motifs. Several embodiments relate to custom peptide derivatives of the of the γc-box motifs of IL-15, IL-2, IL-21, IL-4, IL-9, or IL-7 having a partial amino acid sequence that shows approximately 50%, 50-60%, 60-70%, 70-80%, 80%, 90%, 95%, 97%, 98%, 99% or 99.8% identity to amino acid sequences of the of the γc-box motifs of IL-15, IL-2, IL-21, IL-4, IL-9, or IL-7. Custom peptide derivatives of the of the γc-box motifs of IL-15, IL-2, IL-21, IL-4, IL-9, or IL-7 further include any peptide wherein a partial amino acid sequence of that peptide derivative comprises amino acids with similar physico-chemical properties to the amino acids of sequence of the γc-box motifs of IL-15, IL-2, IL-21, IL-4, IL-9, or IL-7.

Several embodiments relate to custom peptide derivatives that would inhibit the function of one, all, or selective members of the γc-cytokines. In some embodiments, the custom peptide derivatives selectively target individual γc-cytokine family members. For example, a custom peptide derivative can selectively inhibit the function of IL-2, IL-4, IL-7, IL-9, IL-15, or IL-21. In other embodiments, a custom peptide derivative can inhibit 2 or more γc-cytokine family members. For example, the custom peptide derivatives of the present embodiments can selectively inhibit the function of IL-2 in combination with one or more of IL-4, IL-7, IL-9, IL-15, and IL-21; IL-4 in combination with one or more of IL-7, IL-9, IL-15, and IL-21; IL-7 in combination with one or more of IL-9, IL-15, and IL-21; IL-9 in combination with one or more of IL-2, IL-4, IL-7, IL-15, and IL-21; IL-15 in combination with one or more of IL-2, IL-4, IL-7, IL-9, and IL-21; or IL-21 in combination with one or more of IL-2, IL-4, IL-7, IL-9, and IL-15. In other embodiments, custom peptide derivatives can comprehensively target all γc-cytokine family members. Not wishing to be bound by a particular theory, the custom peptide derivatives can inhibit the function of all or selective members of the γc-cytokines by diminishing the binding of γc-cytokines to the γc-subunit, for example, as a competitive inhibitor. Such custom peptide derivatives may be used in diverse applications, including as a clinical drug.

The terms "oligopeptide," "polypeptide," "peptide," and "protein" can be used interchangeably when referring to the custom peptide derivatives provided in accordance with the present embodiments and can be used to designate a series of amino acid residues of any length. Peptides according to the present embodiments may also contain non-natural amino acids. Linker elements can be joined to the peptides of the present embodiments through peptide bonds or via chemical bonds. The peptides of the present embodiments may be linear or cyclic, and may include (D) as well as (L) amino acids. Peptides of the present embodiments may also contain one or more rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylamino), with or without any of a wide variety of side chain modifications and/or substitutions (e.g., methylation, benzylation, t-butylation, tosylation, alkoxycarbonylamino, and the like). Residues other than common amino acids that may be present include, but are not limited to, penicillamine, tetramethylene cysteine, pentamethylene cysteine, mercaptopropionic acid, pentamethylene-mercaptopropionic acid, 2-mercaptobenzene, 2-mercaptoaniline, 2-mercaptoproline, ornithine, diaminobutyric acid, aminoadipic acid, m-aminomethylbenzoic acid, and diaminopropionic acid.

Peptides of the present embodiments can be produced and obtained by various methods known to those skilled in the art. For example, the peptide may be produced by genetic engineering, based on the nucleotide sequence coding for the peptide of the present embodiments, or chemically synthesized by means of peptide solid-phase synthesis and the like, or produced and obtained in their combination. One skilled in the art can synthesize the custom peptide derivatives based on the present disclosure of the conserved γc-box motif and knowledge of the biochemical properties of amino acids as described in FIG. 2. Some embodiments also relate to polynucleotides comprising nucleotide sequences encoding the peptides of the present invention. "Nucleotide sequence," "polynucleotide," or "nucleic acid" can be used interchangeably, and are understood to mean either double-stranded DNA, a single-stranded DNA or products of transcription of the DNAs (e.g., RNA molecules). Polynucleotides can be administered to cells or subjects and expressed by the cells or subjects, rather than administering the peptides themselves. Several embodiments also relate to genetic constructs comprising a polynucleotide sequence encoding the peptides of the present invention. Genetic constructs can also contain additional regulatory elements such as promoters and enhancers and, optionally, selectable markers.

Methods of Treating γc-Cytokine Mediated Diseases

Several embodiments relate to the use of γc-antagonist peptides in the treatment of γc-cytokine mediated diseases. Use of custom peptide derivative according to the present embodiments allows for flexibility in the design of the therapeutic agent (custom design of the peptide) and enables more comprehensive outcomes, which would not be accomplished by conventional strategies employing anti-cytokine or anti-cytokine receptor antibodies.

Described herein is a novel method of blocking the action of γc-family cytokines. Such manipulations can yield effective methods of clinical interventions in treating diseases related to the dysregulation or dysfunction of γc-cytokines. Examples of disease that may be treated by disrupting the interaction between the γc-cytokine and the γc-subunit include autoimmune diseases such as systemic lupus erythematosis, Sjoegren's syndrome, Wegener's granulomatosis Celiac disease, Hashimoto's or auto-immune thyroiditis; collagen diseases including rheumatoid arthritis, inflammatory bowel disease, diabetes mellitus, autoimmune diseases of the skin such as psoriasis; degenerative neuronal diseases such as multiple sclerosis, uvietis or inflammation of the eye and sympathetic ophthalmia, graft-versus-host disease (GvHD) and myasthenia gravis.

In some embodiments, the γc-antagonist peptides described herein may be used in the treatment of 1-Human T-cell Lymphotropic type I and II (HTLV-I and HTLV-II)-associated diseases including Adult T-cell Leukemia (ATL), HTLV-associated Myelopathy/Tropical Spastic Paraparesis (HAM/TSP), and other non-neoplastic inflammatory diseases associated with HTLV such as uveitis (HU), arthropathy, pneumopathy, dermatitis, exocrinopathy and myositis. In some embodiments, the γc-antagonist peptides described herein may be used in the treatment of other viral diseases such as influenza, AIDS, HBV and Herpes or parasitic diseases.

In several embodiments, the γc-antagonist peptides may be administered before, during, and or after transplantation of various organs as an immunosuppressant agent.

In some embodiments, the γc-antagonist peptides described herein may be used in the treatment of immune-mediated diseases such as asthma and other inflammatory respiratory diseases, such as, but not limited to sinusitis, hay fever, bronchitis, chronic obstructive pulmonary disease (COPD), allergic rhinitis, acute and chronic otitis, lung fibrosis. In some embodiments, γc-antagonist peptides may be administered to treat or prevent allergic reactions due to exposure to allergens, chemical agents or other common causes of acute respiratory disease. In some embodiments, γc-antagonist peptides may be administered to treat or prevent inflammatory responses caused by viruses, bacteria, chemical reagents, and biochemical reagents.

In several embodiments, the γc-antagonist peptides may be administered to treat some types of malignancies such as LGL-leukemia, Intraepithelial lymphoma and leukemia in Refractory Celiac Disease, NK leukemia/lymphoma and NK-T leukemia/lymphoma In some embodiments, custom peptide derivatives according to the embodiments described herein can be used for cosmetic purposes, such as the treatment of acne, hair loss, sunburn and nail maintenance, included to ointment as anti-aging component because of the anti-inflammatory nature of them.

Several embodiments relate to therapeutic antagonist peptides that would inhibit the function of all or selective members of the γc-cytokines. In some embodiments, therapeutic antagonist peptides selectively inhibit individual γc-cytokine family members (custom peptides). In other embodiments, therapeutic antagonist peptides can comprehensively inhibit all γc-cytokine family members (Simul-Block). In some embodiments, therapeutic antagonist peptides selectively inhibit subsets of the γc-cytokines. Not wishing to be bound by a particular theory, the peptide antagonists can inhibit the function of all or selective members of the γc-cytokines by diminishing the binding of γc-cytokines to the γc-subunit, for example, as a competitive inhibitor.

Several members of the γc-cytokine family, IL-2, IL-7, and IL-15, but not IL-4 have been implicated as being involved in graft versus host disease (GvHD) in an experimental mouse model. (Miyagawa et al., 2008 J. Immunol. 181:1109-19.) One embodiment relates to the use of therapeutic antagonist peptides that selectively inhibit IL-2, IL-7, and IL-15 activity for the treatment of GvHD in humans, allowing survival of the grafted tissues or bone marrow cells. Other embodiments relate to the use of therapeutic antagonist peptides that selectively inhibit a combination of IL-2 and IL-7, IL-2, and IL-15, or IL-7 and IL-15 to treat GvHD. Other embodiments relate to the use of a combination of therapeutic antagonist peptides that selectively inhibit IL-2, IL-7, or IL-15.

Some embodiments relate to the use of therapeutic antagonist peptides that selectively inhibit IL-2 function for the treatment of autoimmune disorders where T-regs have been implicated as playing a role. In some embodiments, peptide-mediated inhibition of T-regs can enhance the natural anti-cancer immunity in humans, providing a novel means of anti-cancer therapy.

Several embodiments relate to the use of therapeutic antagonist peptides that selectively inhibit IL-4 to treat asthma.

Some embodiments relate to the use of therapeutic antagonist peptides that selectively inhibit IL-7 either alone or in combination with therapeutic antagonist peptides that selectively inhibit the γc-cytokine family member, IL-15, as a therapeutic agent for LGL leukemia. In some embodiments therapeutic antagonist peptides that selectively inhibit both IL-7 and IL-15 activity can be used to treat LGL leukemia. Several embodiments relate to the use of BNZ-γ to treat LGL leukemia. In some embodiments, specific γc-antagonist peptides that selectively IL-15 alone or specific γc-antagonist peptides that selectively IL-15 and IL-7 are used as a therapeutic agent for CD4/CD8 T lymphocyte-associated leukemia including that caused by the HTLV-I.

Several embodiments relate to the use of γc-antagonist peptides that selectively inhibit the activity of IL-9, either alone or in combination with the other γc-cytokine family members, as a therapeutic agent for human diseases that involve the abnormal development of Th17 cells.

Several embodiments relate to the use of therapeutic antagonist peptides that selectively inhibit IL-15 activity as a therapeutic agent for treating CD. One recent publication suggested that IL-21, in addition to IL-15, may play a role in CD pathogenesis. (See Bodd et al., 2010, Mucosal Immunol. 3:594-601.) This suggests that optimum treatment of CD by conventional anti-cytokine or cytokine-receptor antibodies would benefit from a combination of at least two antibodies recognizing component that belong to the IL-15 and IL-21 systems. In some embodiments, custom derivative antagonist peptides that selectively inhibit both IL-15 and IL-21 activity are used as a therapeutic agent for treating CD.

In addition to having therapeutic applications, γc-antagonist peptides have applications in consumer products as well. Several embodiments relate to the use of γc-antagonist peptides in skin care products such as anti-aging, anti-inflammatory, anti-acne, and other related applications. Some embodiments relate to the use of γc-antagonist peptides in hair products as anti-hair loss ingredient to treat hair loss caused by autoimmune disorders.

Another embodiment relates to the development of chemical compounds (non-peptide, non-protein) that have a spatial structure which resembles the 19-mer amino acid sequence I-K-E-F-L-Q-R-F-I-H-I-V-Q-S-I-I-N-T-S(SEQ ID NO: 34) and can fit into the pocket of the γc-subunit to structurally hinder the access of a γc-cytokine to the γc-subunit for binding. Some embodiments relate to the use of structurally similar chemical compounds as inhibitors of γc-cytokine activity. Such molecular mimicry strategy to further refine the development of synthetic compounds resembling in structure to existing biological peptide/proteins is described in Orzaez et al., 2009 Chem. Med. Chem. 4:146-160. Another embodiment relates to administration of chemical compounds (non-peptide, non-protein) that have a resembling 3D structure as the 19-mer amino acids sequence I-K-E-F-L-Q-R-F-I-H-I-V-Q-S-I-I-N-T-S(SEQ ID NO: 34) to treat γc-cytokine-mediated diseases.

Several embodiments relates to the administration of a peptide of amino acid sequence I-K-E-F-L-Q-R-F-I-H-I-V-Q-S-I-I-N-T-S(SEQ ID NO: 34) to treat γc-cytokine-mediated diseases. Another embodiment relates to the administration of derivative peptides of amino acid sequence I-K-E-F-L-Q-R-F-I-H-I-V-Q-S-I-I-N-T-S(SEQ ID NO: 34), wherein the amino acid sequence of the derivative peptide has similar physico-chemical properties as a peptide of the amino acid sequence I-K-E-F-L-Q-R-F-I-H-I-V-Q-S-I-I-N-T-S(SEQ ID NO: 34), but has distinct biological activity, to treat γc-cytokine-mediated diseases. Another embodiment relates to administration of a peptide of amino acid sequence I-K-E-F-L-Q-R-F-I-H-I-V-Q-S-I-I-N-T-S(SEQ ID NO: 34) conjugated to the N- and C-termini or to the side residues of existing biological proteins/peptides into patients to treat γc-cytokine-mediated diseases.

Several embodiments relate to administration of polyclonal and monoclonal antibodies raised against a peptide comprising of amino acid sequence I-K-E-F-L-Q-R-F-I-H-I-V-Q-S-I-I-N-T-S(SEQ ID NO: 34) into patients as an immunogen to treat γc-cytokine-mediated diseases. Another embodiment relates to administration of polyclonal and monoclonal antibodies that were raised against derivative peptides of amino acid sequence I-K-E-F-L-Q-R-F-I-H-I-V-Q-S-I-I-N-T-S(SEQ ID NO: 34) wherein the amino acid sequence of the derivative peptide has similar physico-chemical properties as a peptide of the amino acid sequence I-K-E-F-L-Q-R-F-I-H-I-V-Q-S-I-I-N-T-S(SEQ ID NO: 34), but has distinct biological activity, into patients as an immunogen to treat γc-cytokine-mediated diseases.

Administration of γc-Antagonist Peptides

The present embodiments also encompass the use of γc-antagonist peptides for the manufacture of a medicament for the treatment of a disease. The present embodiments also encompass a pharmaceutical composition that includes γc-antagonist peptides in combination with a pharmaceutically acceptable carrier. The pharmaceutical composition can include a pharmaceutically acceptable carrier and a non-toxic therapeutically effective amount of γc-antagonist peptides, or other compositions of the present embodiments.

The present embodiments provide methods of using pharmaceutical compositions comprising an effective amount of antagonists for γc-cytokines in a suitable diluent or carrier. A γc-antagonist of the present embodiments can be formulated according to known methods used to prepare pharmaceutically useful compositions. A γc-antagonist can be combined in admixture, either as the sole active material or with other known active materials, with pharmaceutically suitable diluents (e.g., phosphate, acetate, Tris-HCl), preservatives (e.g., thimerosal, benzyl alcohol, parabens), emulsifying compounds, solubilizers, adjuvants, and/or carriers such as bovine serum albumin. Suitable carriers and their formulations are described in Remington's Pharmaceutical Sciences, 16$^{th}$ ed. 1980 Mack Publishing CO. Additionally, such compositions can contain a γc-antagonist complexed with polyethylene glycol (PEG), metal ions, or incorporated into polymeric compounds such as polyacetic acid, polyglycolic acid, hydrogels etc., or incorporated into liposomes, microemulsions, micelles, unilamellar or multilamellar vesicles, erythrocyte ghosts, or spheroblasts. Such compositions will influence the physical state, solubility, stability, rate of in vivo release, and rate of in vivo clearance or a γc-antagonist. A γc-antagonist can be conjugated to antibodies against cell-specific antigens, receptors, ligands, or coupled to ligands for tissue-specific receptors.

Methods of administrating γc-antagonists of the present embodiments may be selected as appropriate, depending on factors, such as the type of diseases, the condition of subjects, and/or the site to be targeted. The γc-antagonists can be administered topically, orally, parenterally, rectally, or by inhalation. The term "parenteral" includes subcutaneous injections, intravenous, intramuscular, intraperitoneal, intracisternal injection, or infusion techniques. These compositions will typically include an effective amount of a γc-antagonist, alone or in combination with an effective amount of any other active material. The amount of the peptide contained in pharmaceutical compositions of the present embodiments, dosage form of the pharmaceutical compositions, frequency of administration, and the like may be selected as appropriate, depending on factors, such as the type of diseases, the condition of subjects, and/or the site to be targeted. Such dosages and desired drug concentrations contained in the compositions may vary affected by many parameters, including the intended use, patient's body weight and age, and the route of administration. Pilot studies will first be conducted using animal studies and the scaling to human administration will be performed according to art-accepted practice.

In one embodiment, host cells that have been genetically modified with a polynucleotide encoding at least one γc-antagonist peptide are administered to a subject to treat a proliferation disorder and/or to reduce the growth of malignant cells. The polynucleotide is expressed by the host cells, thereby producing the peptides within the subject. Preferably, the host cells are allogeneic or autogeneic to the subject.

In a further aspect, γc-antagonist peptides can be used in combination with other therapies, for example, therapies inhibiting cancer cell proliferation and growth. The phrase "combination therapy" embraces the administration of γc-antagonist peptides and an additional therapeutic agent as part of a specific treatment regimen intended to provide a beneficial effect from the co-action of these therapeutic agents. Administration of these therapeutic agents in combination typically is carried out over a defined time period (usually minutes, hours, days or weeks depending upon the combination selected).

A combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by an appropriate route including, but not limited to, oral routes, intravenous routes, intramuscular routes, and direct absorption through mucous membrane tissues. There therapeutic agents can be administered by the same route or by different routes. The sequence in which the therapeutic agents are administered is not narrowly critical.

Combination therapy also can embrace the administration of the therapeutic agents as described above in further combination with other biologically active ingredients (such as, but not limited to, a second and different therapeutic agent) and non-drug therapies (such as, but not limited to, surgery or radiation treatment). Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporarily removed from the administration of the therapeutic agents, perhaps by days or even weeks.

In certain embodiments, γc-antagonist peptides can be administered in combination with at least one anti-proliferative agent selected from the group consisting of chemotherapeutic agent, an antimetabolite, and antitumorgenic agent, and antimitotic agent, and antiviral agent, and antineoplastic agent, an immunotherapeutic agent, and a radiotherapeutic agent.

In certain embodiments, γc-antagonist peptides can be administered in combination with at least one anti-inflammatory agent selected from the group consisting of steroids, corticosteroids, and nonsteroidal anti-inflammatory drugs.

Also provided are kits for performing any of the above methods. Kits may include a γc-antagonist according to the present embodiments. In some embodiments, the kit may include instructions. Instructions may be in written or pictograph form, or may be on recorded media including audio tape, audio CD, video tape, DVD, CD-ROM, or the like. The kits may comprise packaging.

Definitions

As used herein, the term "patient" refers to the recipient of a therapeutic treatment and includes all organisms within the kingdom animalia. In preferred embodiments, the animal is within the family of mammals, such as humans, bovine, ovine, porcine, feline, buffalo, canine, goat, equine, donkey, deer, and primates. The most preferred animal is human.

As used herein, the term "treat" or any variation thereof (e.g., treatment, treating, etc.), refers to any treatment of a patient diagnosed with a biological condition, such as CD4–, CD8–, and LGL-leukemia, an autoimmune disease, systemic lupus erythematosis, Sjoegren's syndrome, Wegener's granulomatosis, Celiac disease, Hashimoto's thyroiditis, a collagen disease, rheumatoid arthritis, inflammatory bowel disease, diabetes mellitus, psoriasis, a degenerative neuronal disease, multiple sclerosis, uvietis, inflammation of the eye, graft-versus-host disease (GvHD), myasthenia gravis, 1-Human T-cell Lymphotropic type I and II (HTLV-I and HTLV-II)-associated diseases, Adult T-cell Leukemia (ATL), HTLV-associated Myelopathy/Tropical Spastic Paraparesis (HAM/TSP), uveitis (HU), arthropathy, pneumopathy, dermatitis, exocrinopathy, myositis, influenza, AIDS, HBV, Herpes, asthma, sinusitis, hay fever, bronchitis, chronic obstructive pulmonary disease (COPD), allergic rhinitis, acute and chronic otitis, lung fibrosis, NK leukemia/lymphoma and NK-T leukemia/lymphoma. The term treat, as used herein, includes: (i) preventing or delaying the presentation of symptoms associated with the biological condition of interest in an at-risk patient who has yet to display symptoms associated with the biological condition; (ii) ameliorating the symptoms associated with the biological condition of interest in a patient diagnosed with the biological condition; (iii) preventing, delaying, or ameliorating the presentation of symptoms associated with complications, conditions, or diseases associated with the biological condition of interest in either an at-risk patient or a patient diagnosed with the biological condition; (iv) slowing, delaying or halting the progression of the biological condition; and/or (v) preventing, delaying, slowing, halting or ameliorating the cellular events of inflammation.

The term "symptom(s)" as used herein, refers to common signs or indications that a patient is suffering from a specific condition or disease.

The term "effective amount," as used herein, refers to the amount necessary to elicit the desired biological response. In accordance with the present embodiments, an effective amount of a γc-antagonist is the amount necessary to provide an observable effect in at least one biological factor for use in treating a biological condition.

"Recombinant DNA technology" or "recombinant" refers to the use of techniques and processes for producing specific polypeptides from microbial (e.g., bacterial, yeast), invertebrate (insect), mammalian cells or organisms (e.g., transgenic animals or plants) that have been transformed or transfected with cloned or synthetic DNA sequences to enable biosynthesis of heterologous peptides. Native glycosylation pattern will only be achieved with mammalian cell expression system. Prokaryotic expression systems lack the ability to add glycosylation to the synthesized proteins. Yeast and insect cells provide a unique glycosylation pattern that may be different from the native pattern.

A "Nucleotide sequence" refers to a polynucleotide in the form of a separate fragment or as a component of a larger DNA construct that has been derived from DNA or RNA isolated at least once in substantially pure form, free of contaminating endogenous materials and in a quantity or concentration enabling identification, manipulation, and recovery of its component nucleotide sequences by standard molecular biology methods (as outlined in Current Protocols in Molecular Biology).

"Recombinant expression vector" refers to a plasmid comprising a transcriptional unit containing an assembly of (1) a genetic element or elements that have a regulatory role in gene expression including promoters and enhances, (2) a structure or coding sequence that encodes the polypeptide according to the present embodiments, and (3) appropriate transcription and translation initiation sequence and, if desired, termination sequences. Structural elements intended for use in yeast and mammalian system preferably include a signal sequence enabling extracellular secretion of translated polypeptides by yeast or mammalian host cells.

"Recombinant microbial expression system" refers to a substantially homogenous monoculture of suitable hot microorganisms, for example, bacteria such as *E. coli*, or yeast such as *S. cerevisiae*, that have stably integrated a recombinant transcriptional unit into chromosomal DNA or carry the recombinant transcriptional unit as a component of a residual plasmid. Generally, host cells constituting a recombinant microbial expression system are the progeny of a single ancestral transformed cell. Recombinant microbial expression systems will express heterologous polypeptides upon induction of the regulatory elements linked to a structural nucleotide sequence to be expressed.

The following Examples are presented for the purposes of illustration and should not be construed as limitations.

EXAMPLES

Example 1

Method for Assessing the Inhibitory Activity of γc-Antagonist Peptide

The capacity of any custom derivative peptide prepared according to the present embodiments for inhibiting the action of one γc-cytokine family member is determined using mammalian cellular assays to measure their proliferative response to the γc-cytokine family member.

For each of the six γc-cytokines, indicator cell lines: CTLL-2, a murine CD8 T cells line available from American Type Culture Collection, and PT-18, a murine mast cell line and its subclone PT-183, is transfected with human IL-2Rβ gene to make the cells responsive to IL-2 and IL-15 (Tagaya et al., 1996, EMBO J. 15:4928-39), and is used to quantitatively determine the γc-cytokine's growth-promoting activity (See Current protocols in Immunology from Wiley and Sons for a methodological reference). The indicator cells demonstrate semi-linear dose-dependent response when measured by a colorimetric WST-1 assay over a range of concentrations (See Clontech PT3946-1 and associated user manual, incorporated herein by reference, for a detailed description of the reagents and methods). Once the appropriate doses of the cytokine that yield the 50% and 95% maximum response from the indicator cell line is determined, various concentrations (ranging from 1 pM to 10 μM) of the purified or synthesized custom derivative peptide is added to each well containing the cytokine and indicator cells. The reduction in light absorbance at 450 nm is used as an indicator of inhibition of cytokine-stimulated cellular proliferation. Typically, the cells are stimulated by the cytokines such that the absorbance of the well containing indicator cell line and the cytokine is between 2.0 and 3.0, which is reduced to a range of 0.1 to 0.5 by the addition of inhibitory peptides.

Example 2

BNZ-γ Peptide Specifically Inhibits the Growth-Promoting Activities of IL-9 and IL-15

Figure 3A:
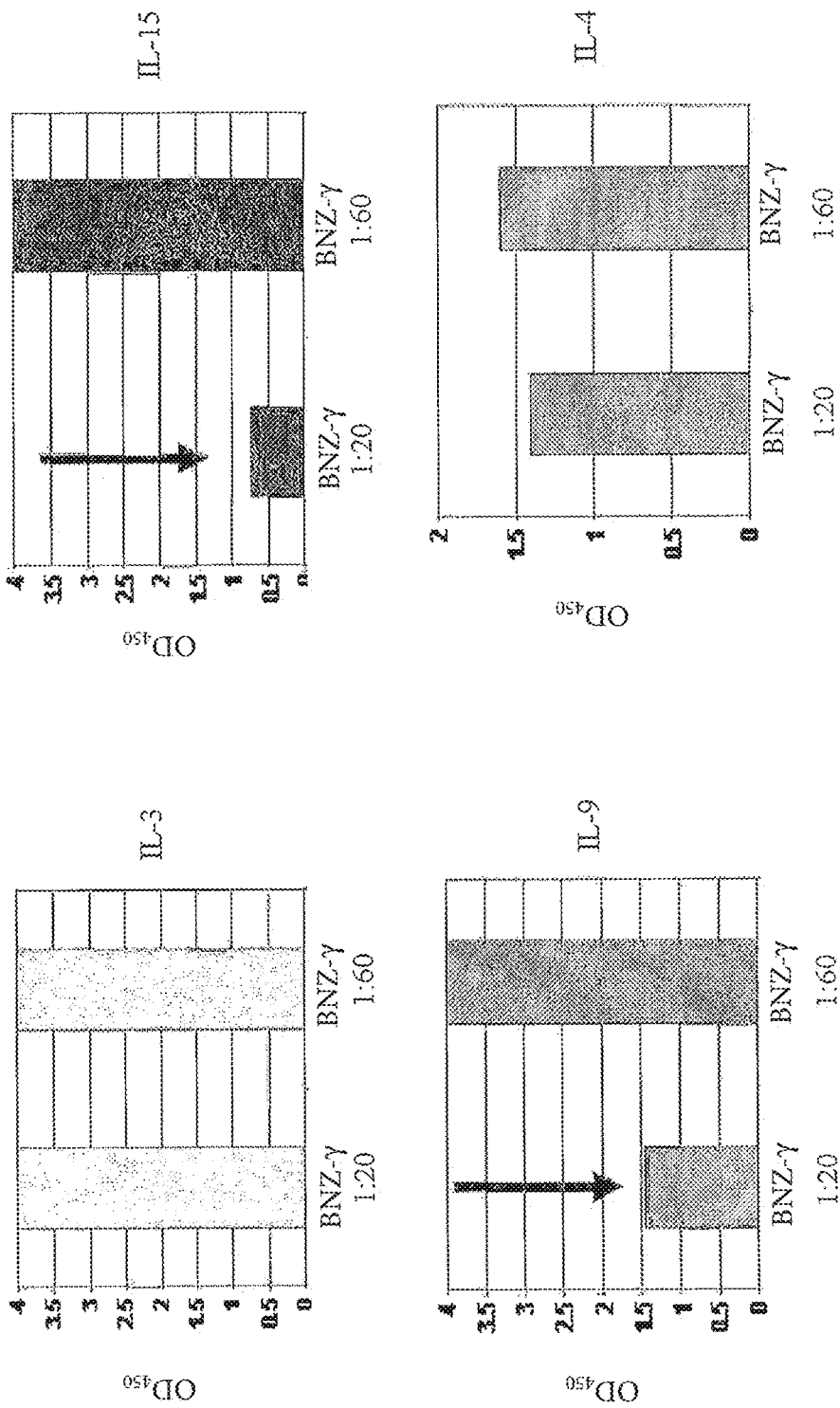
FIG. 3A shows inhibition of IL-2, IL-15, and IL-9 activity by BNZ-γ in a PT-18 proliferation assay.

Using PT-18 (cells as described above, the ability of the BNZ-γ peptide to specifically inhibit the growth-promoting activity of select γc-cytokines was determined (FIG. 3A). IL-3, a non-γc-cytokine that supports the growth of PT-181 cells, was used as a negative control. Briefly, PT-18β cells were incubated either with two different dilutions of BNZ-γ peptide produced by HEK293T cells (1:20 or 1:50 dilution of the original supernatant of HEK293T cells transfected with a BNZ-γ expression construct) or without BNZ-γ peptide in the presence of IL-3, IL-9, IL-15, or IL-4 (1 nM of each cytokine in the culture). The growth-responses of the cells were determined 2 days after the introduction of BNZ-γ peptide and the cytokine using the WST-1 assay. The growth-promoting activity of IL-3 (a non γc-cytokine) was not inhibited by BNZ-γ. In contrast, the activity of IL-15 and IL-9 were significantly (p<0.01 Student's T test) reduced by the BNZ-γ peptide. Cellular proliferation stimulated by IL-4, another γc-cytokine, was not affected by the by the addition of BNZ-γ peptide. Results for IL-3, IL-9, IL-15, and IL-4 are shown at FIG. 3A.

Figure 3B:
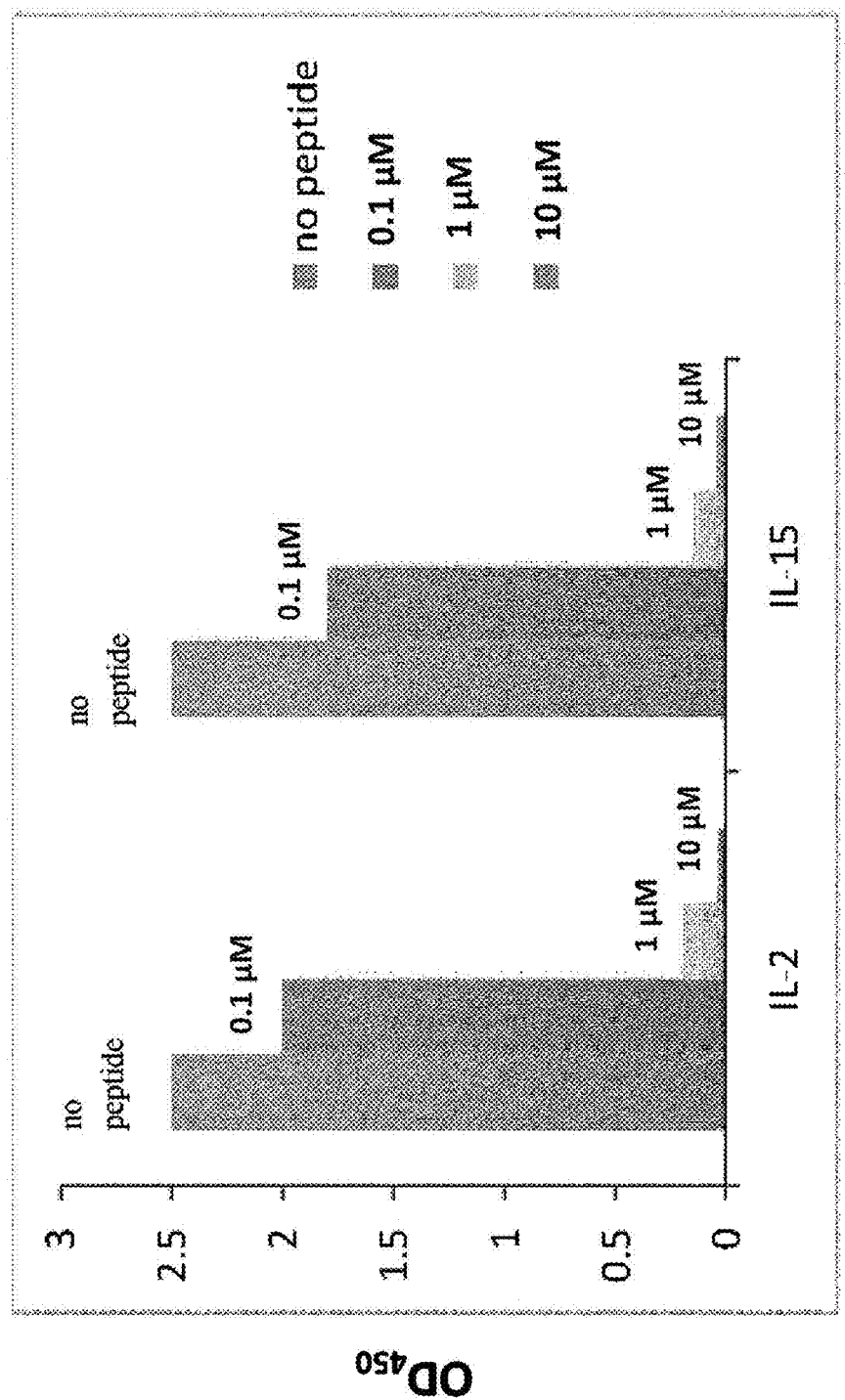
FIG. 3B shows a proliferation assay of CTTL2 cells grown in the presence of IL-2 or IL-15 and 0, 0.1, 1 or 10 uM BNZ-γ.
Figure 3C:
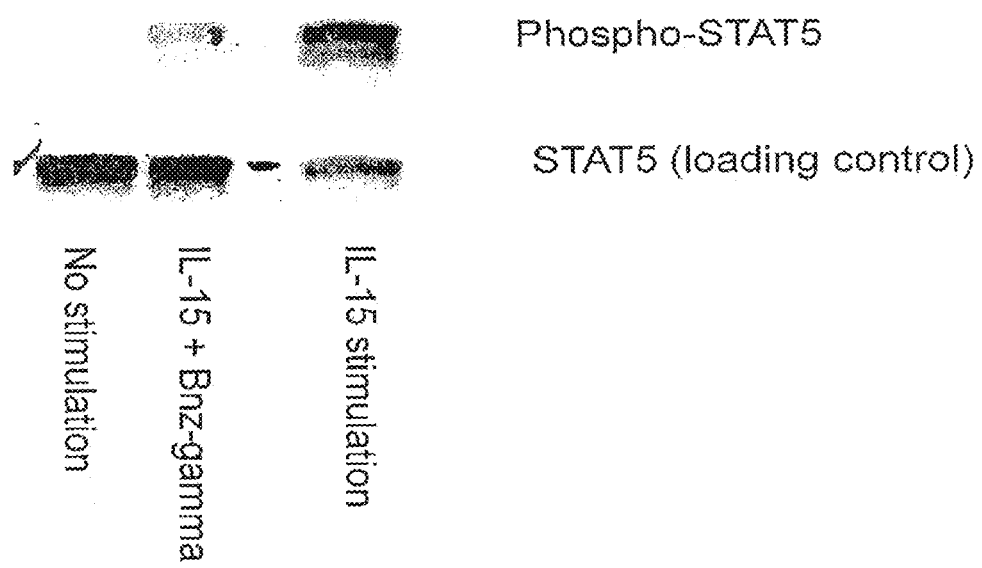
FIG. 3C shows inhibition of IL-15-mediated tyrosine-phosphorylation of STAT5 by BNZ-γ.

In a similar assay, the murine cell line CTTL2 was used. In this assay the cells were cultured with 0.5 nM of recombinant IL-2 in RPMI 10% fetal Calf Serum. To set up the proliferation assay, cells were washed from the cytokines 3 times. Cells were seeded at 1×10(5) cells per well of a 96-well plate with final concentration of 50 pM of IL-2 or IL-15. Various concentration of BNZ-γ peptide (0.1, 1, and 10 ug/ml) was added to each well. Cells were cultured for 20 hours and in the last 4 hours, $^3$H-thymidine was added to the plates. Cells were harvested using a plate reader. The data is shown in FIG. 3B.

Example 3

Method for Measuring Inhibition γc-Cytokine Activity by Assaying 3H-Thymidine Incorporation of as a Marker of Cellular Proliferation Inhibition of γc-cytokine-induced proliferation of an indicator cell population by antagonist custom derivative peptides is measured by the 3H-thymidine incorporation assay. Briefly, radiolabeled thymidine (1 microCi) is given to 20-50,000 cells undergoing proliferation in the presence of cytokines. The cell-incorporated radioactivity is measured by trapping cell-bound radioactivity to a glass-fiber filter using a conventional harvester machines (Example, Filtermate Universal Harvester from Perkin-Elmer), after which the radioactivity is measured using a b-counter (Example 1450, Trilux microplate scintillation counter).

Example 4

Method for Measuring Inhibition γc-Cytokine Activity by Assaying Incorporation of a Cell-Tracker Dye as a Marker of Cellular Proliferation Indicator cells are incubated in the presence of a selected γc-cytokine or in the presence of a selected γc-cytokine and a selected custom derivative peptide. The cell population is then labeled in vitro using a cell-tracker dye, for example, CMFDA, C2925 from Invitrogen, and the decay of cellular green fluorescence at each cellular division is monitored using a flow-cytometer (for example, Beckton-Dickinson FACScalibur). Typically, in response to γc-cytokine stimulation 7~10 different peaks corresponding to the number of divisions that the cells have undergone will appear on the green fluorescence channel. Incubation of the cells with the selected γc-cytokine and antagonist custom derivative peptide reduces the number of peaks to only 1 to 3, depending on the degree of the inhibition.

Example 5

Inhibition of Intracellular Signaling by BNZ-γ and its Derivative Antagonists

In addition to stimulating cellular proliferation, binding of the γc-cytokines to their receptors causes a diverse array of intracellular events. (Rochman et al. 2009 Nat. Rev. Immunol. 9:480-90, Pesu et al. 2005 Immunol. Rev. 203:127-142.) Immediately after the cytokine binds to its receptor, a tyrosine kinase called Jak3 (Janus-kinase 3) is recruited to the receptor at the plasma membrane. This kinase phosphorylates the tyrosine residues of multiple proteins including the γc-subunit, STAT5 (Signal Transducer and Activator of Transcription 5) and subunits of the PI3 (Phosphatidylinositol 3) kinase. Among these, the phosphorylation of STAT5 has been implicated in many studies as being linked to the proliferation of cells initiated by the γc-cytokine. (Reviewed in Hennighausen and Robinson, 2008 Genes Dev. 22:711-21.) In accordance with these published data, whether or not the BNZ-γ peptide inhibits the tyrosine phosphorylation of STAT5 molecule in PT-18β cells stimulated by IL-15 was examined (results shown in FIG. 3C).

PT-18β cells were stimulated by IL-15 in the presence or absence of BNZ-γ peptide. Cytoplasmic proteins were extracted from the cells according to a conventional method as described in Tagaya et al. 1996 EMBO J. 15:4928-39. The extracted cytoplasmic proteins were resolved using a standard SDS-PAGE (Sodium Dodecyl-Sulfate PolyAcrylamide Gel Electrophoresis) and the phorphorylation status was confirmed by an anti-phospho-STAT5 antibody (Cell Signaling Technology, Catalog #9354, Danvers Mass.) using immunoblotting (see FIG. 3C, top panel). To confirm that each lane represented a similar total protein load, the membrane was then stripped, and re-probed with an anti-STAT5 antibody (Cell Signaling Technology, Catalog #9358) (see FIG. 3C, bottom panel).

These results demonstrated that tyrosine phosphorylation of STAT5, a marker of signal transduction, was induced by IL-15 in PT-18β cells, and tyrosine phosphorylation of STAT5 was markedly reduced by the BNZ-γ peptide.

Example 6

Rational Design for BNZ-γ Derivative Antagonistic Peptides

Derivative peptides are prepared based from the core sequence D/E-F-L-E/Q/N-S/R-X-I/K-X-L/I-X-Q (SEQ ID NO: 158) (where X denotes any amino acid) by substituting the defined amino acids of the core sequence with amino acids having identical physico-chemical properties as designated in FIG. 2.

Example 7

Method of Identifying the Inhibitory Specificity of Antagonistic Custom Derivative Peptides The γc-cytokine inhibitory specificity of antagonistic custom derivative peptides is determined by assaying the ability of a custom derivative peptide to inhibit the proliferative response of a cytokine-responsive cell line to each of the 6 γc-cytokines. For example, a mouse cell line, CTLL-2, is used to determine if a candidate peptide inhibits the function of IL-2 and IL-15. PT-18(β) cells are used to determine if a candidate peptide inhibits the function of IL-4 and IL-9. PT-18 (7α) cells are used to determine if a candidate peptide inhibits the function of IL-7, and PT-18(21α) cells are used to determine if a candidate peptide inhibits the function of IL-21. PT-18(β) denotes a subclone of PT-18 cells that exogenously express human IL-2Rβ by gene transfection (See Tagaya et al. 1996), PT-18(7α) denotes a subclone that expresses human IL-7Rα by gene transfection and PT-18 (21Rα) cells express human IL-21Rα.

Another alternative is to use other cell lines that respond to an array of cytokines. An example of this cell line in a human NK cell line NK92 that is commercially available by ATCC (catalog # CRL-2407). This cell line is an IL-2 dependent cell line that responds to other cytokines including IL-9, IL-7, IL-15, IL-12, IL-18, IL-21 (Gong et al. 1994 Leukemia 8: 652-658, Kingemann et al., 1996, Biol Blood Marrow Transplant 2:68; 75, Hodge D L et al., 2002 J. Immunol. 168:9090-8)

Example 8

Preparation of γc-Antagonist Peptides

Custom derivative γc-antagonist peptides are synthesized chemically by manual and automated processes.

Manual synthesis: Classical liquid-phase synthesis is employed, which involves coupling the carboxyl group or C-terminus of one amino acid to the amino group or N-terminus of another. Alternatively, solid-phase peptide synthesis (SPPS) is utilized.

Automated synthesis: Many commercial companies provide automated peptide synthesis for a cost. These companies use various commercial peptide synthesizers, including synthesizers provided by Applied Biosystems (ABI). Custom derivative γc-antagonist peptides are synthesized by automated peptide synthesizers.

Example 9

Biological Production of Custom Derivative γc-Antagonist Peptides Using Recombinant Technology A custom derivative γc-antagonist peptides is synthesized biologically as a pro-peptide that consists of an appropriate tagging peptide, a signal peptide, or a peptide derived from a known human protein that enhances or stabilizes the structure of the BNZ-γ peptide and improves its biological activity. If desired, an appropriate enzyme-cleavage sequence proceeding to the N-terminus of the peptide shall be designed to remove the tag or any part of the peptide from the final protein.

A nucleotide sequence encoding the custom derivative peptide with a stop codon at the 3' end is inserted into a commercial vector with a tag portion derived from thioredoxin of *E. coli* and a special peptide sequence that is recognized and digested by an appropriate proteolytic enzyme (for example, enterokinase) intervening between the tag portion and the nucleotide sequence encoding the custom derivative peptide and stop codon. One example of a suitable vector is the pThioHis plasmid available from Invitrogen, CA. Other expression vectors may be used.

Example 10

Conjugation of the BNZ-γ and Derivative to Carrier Proteins for Immunization Purposes and Generation of Anti-BNZ-γ Antibody BNZ-γ and other custom derivative peptides are used to immunize animals to obtain polyclonal and monoclonal antibodies. Peptides are conjugated to the N- or the C-terminus of appropriate carrier proteins (for example, bovine serum albumin, Keyhold Limpet Hemocyanin (KLH), etc.) by conventional methods using Glutaraldehyde or m-Maleimidobenzoyl-N-Hydroxysuccinimide Ester. The conjugated peptides in conjunction with an appropriate adjuvant are then used to immunize animals such as rabbits, rodents, or donkeys. The resultant antibodies are examined for specificity using conventional methods. If the resultant antibodies react with the immunogenic peptide, they are then tested for the ability to inhibit individual γc-cytokine activity according to the cellular proliferation assays described in Examples 1-3. Due to the composite nature of the derivative peptides it is possible to generate a single antibody that recognizes two different cytokines simultaneously, because of the composite nature of these peptides.

Example 11

Method for Large Scale Production of Custom Derivative γc-Antagonist Peptides

Recombinant proteins are produced in large scale by the use of cell-free system as described elsewhere. (See Takai et al., 2010 Curr. Pharm. Biotechnol. 11(3):272-8.) Briefly, cDNAs encoding the γc-antagonist peptide and a tag are subcloned into an appropriate vector (See Takai et al., 2010 Curr. Pharm. Biotechnol. 11(3):272-8), which is subjected to in vitro transcription, followed immediately by an in vitro translation to produce the tagged peptide. The pro-polypeptide is then purified using an immobilized antibody recognizing the tagged epitope, treated by the proteolytic enzyme and the eluate (which mostly contains the custom derivative peptide of interest) is tested for purity using conventional 18% Tricine-SDS-PAGE (Invitrogen) and conventional comassie staining. Should the desired purity of the peptide not be met (>98%), the mixture is subjected to conventional HPLC (high-performance liquid chromatography) for further purification.

Example 12

Use of Custom Derivative γc-Antagonist Peptides to Block Cytokine Function in HAM/TSP HTLV-1-associated myelopathy (HAM)/tropical spastic paraparesis (TSP) is a chronic progressive myelopathy seen in some people infected with Human T-Lymphotropic Virus Type I (HTLV-I). Infiltration of lymphocytes in the spinal cord is associated with the immune response to HTLV-I and results in the release of certain cytokines. Some of these cytokines may also damage nerves.

Patients with HAM/TSP show an elevated state of the immune system that is similar to that observed in autoimmune diseases (Oh et al. 2008 Neurol Clin. 26:781-785). This elevated state is demonstrated by the ability of HAM/TSP patient's T-cells to undergo spontaneous proliferation in an ex vivo culture for about a week in the absence of exogenously added cytokines. The spontaneous proliferation of T-cells in HAM/TSP patients is attributed, at least partly, to autocrine/paracrine loops of IL-2, IL-9, and IL-15. It has been shown that adding blocking antibody against the IL-2 or IL-15 receptors can inhibit spontaneous T-cell proliferation in a HAM/TSP ex vivo culture system. These observations, along with other data derived from ex vivo studies, have provided the rationale for taking two monoclonal antibodies (an anti-IL-2 receptor alpha or anti-Tac and an anti-IL-15 receptor beta chain) into the clinic for treatment of HAM/TSP (Azimi et al. 2001 Proc. Natl. Acad. Sci. 98:14559-64., Azimi et al., 1999 J. Immunol 163:4064-72). Anti-cytokine receptor antagonists according to the embodiments described herein, would not only be valuable as a therapeutic immuno-modulatory agent for treatment of HAM/TSP, but modulation of immune response in HAM/TSP by anti-cytokine receptor antagonists according to the present embodiments acts proof-of-concept for the use of the anti-cytokine receptor antagonists according to the present embodiments in the treatment of other auto-immune diseases.

To demonstrate the efficacy of custom derivative γc-antagonist peptides according to the embodiments described herein, we tested the ability of BNZ-γ peptide to block immune response to HTLV-I in a spontaneous T-cell proliferation assay using a HAM/TSP ex vivo culture system. Proliferation assays were performed on HAM/TSP patient blood samples with and without the addition of BNZ-γ. These assays evaluated the ability of BNZ-γ to block the function of cytokines, such as IL-2 and IL-15, present in the ex vivo HAM/TSP patient blood culture and prevent spontaneous T-cell proliferation in these samples.

Figure 4A:
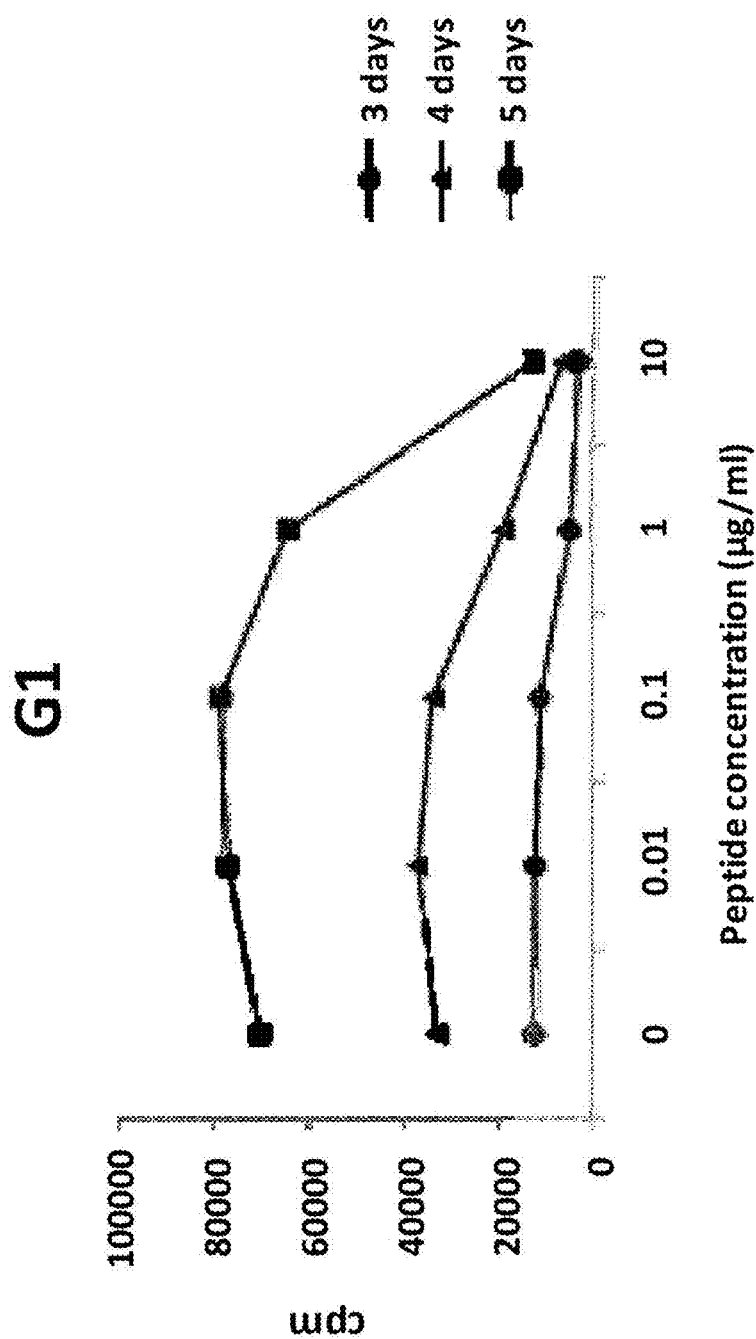
FIG. 4A shows an ex vivo T-cell proliferation assay using HAM/TSP peripheral blood. T-cell proliferation is inhibited by addition of BNZ-γ.
Figure 4B:
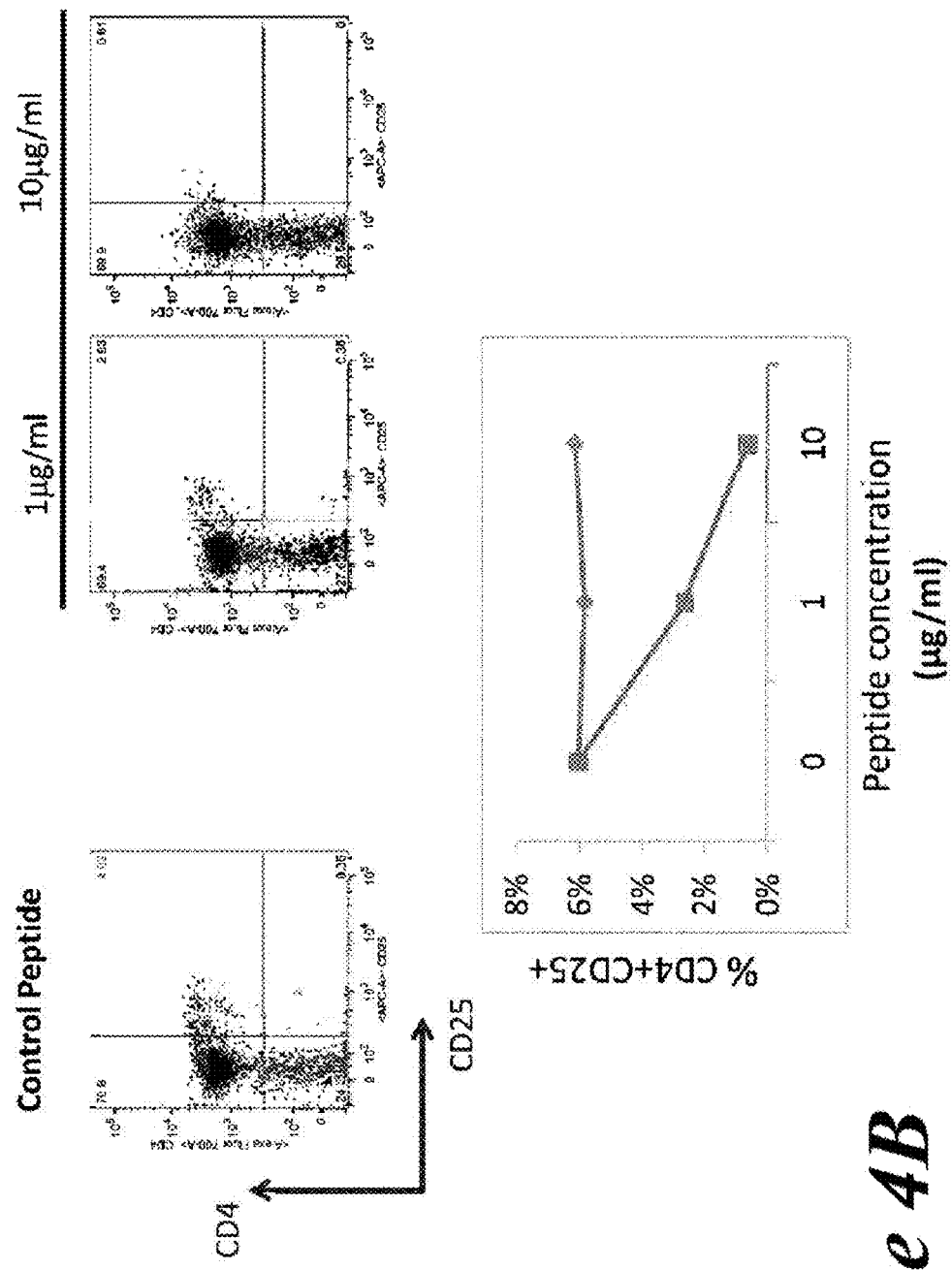
FIG. 4B shows the population of CD4+CD25+ cells in an ex vivo T-cell proliferation assay using HAM/TSP peripheral blood is diminished after adding BNZ-γ to the culture.
Figure 4C:
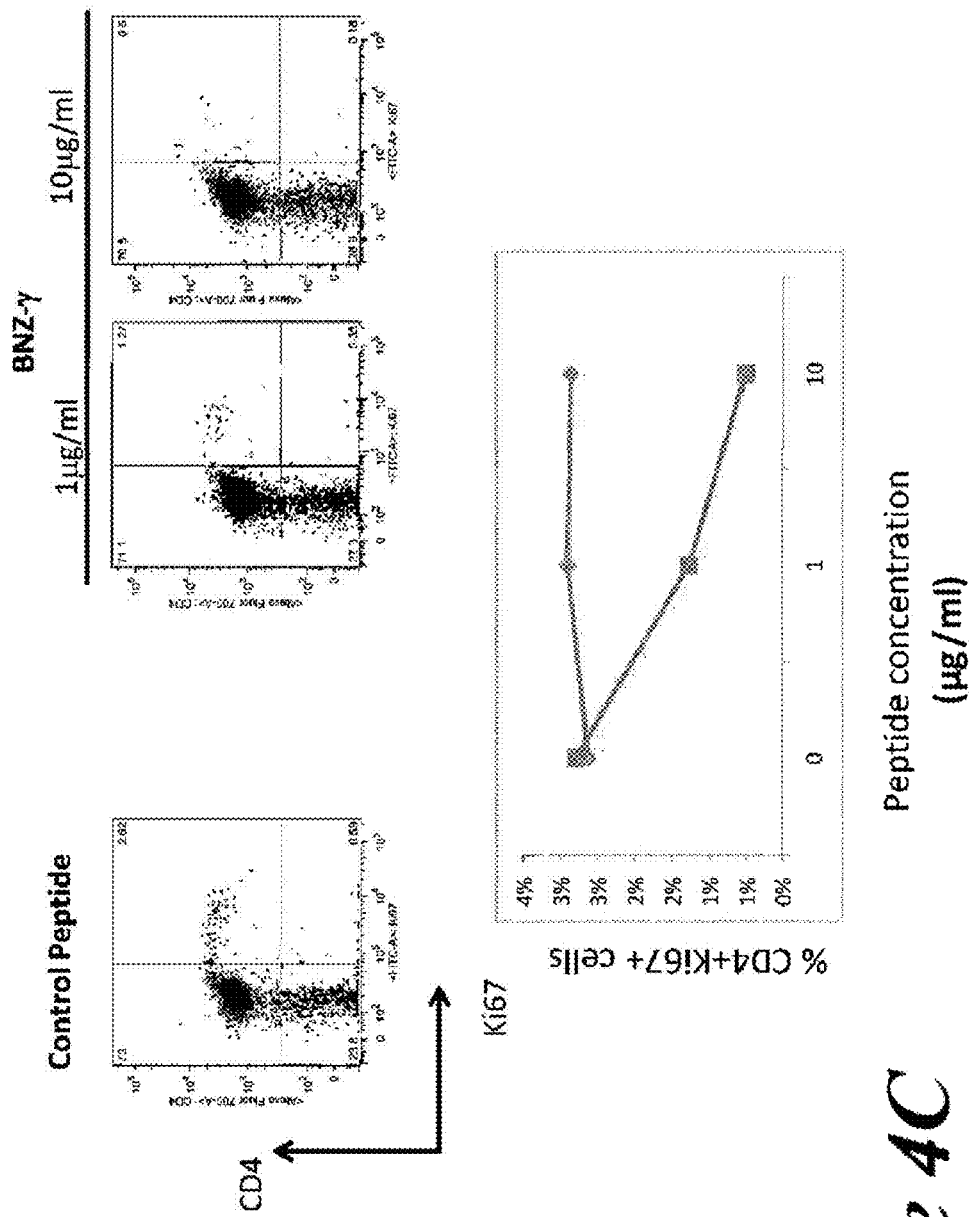
FIG. 4C shows the population of CD4+Ki67 cells in an ex vivo T-cell proliferation assay using HAM/TSP peripheral blood is reduced after adding BNZ-γ to the culture.
Figure 4D:
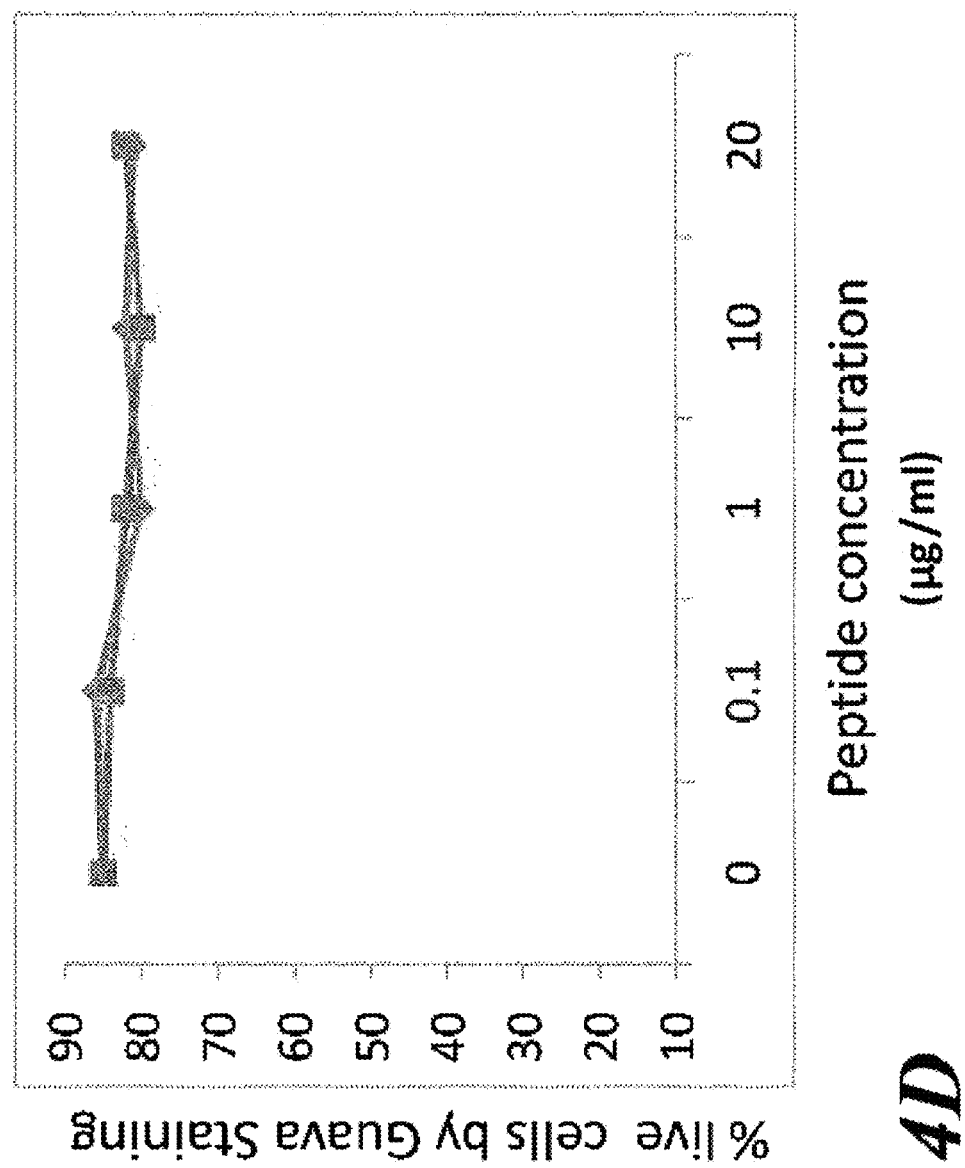
FIG. 4D shows the percent of live cells by Guava staining in an ex vivo T-cell proliferation assay using HAM/TSP peripheral blood is not impacted after adding BNZ-γ to the culture.
Figure 5:
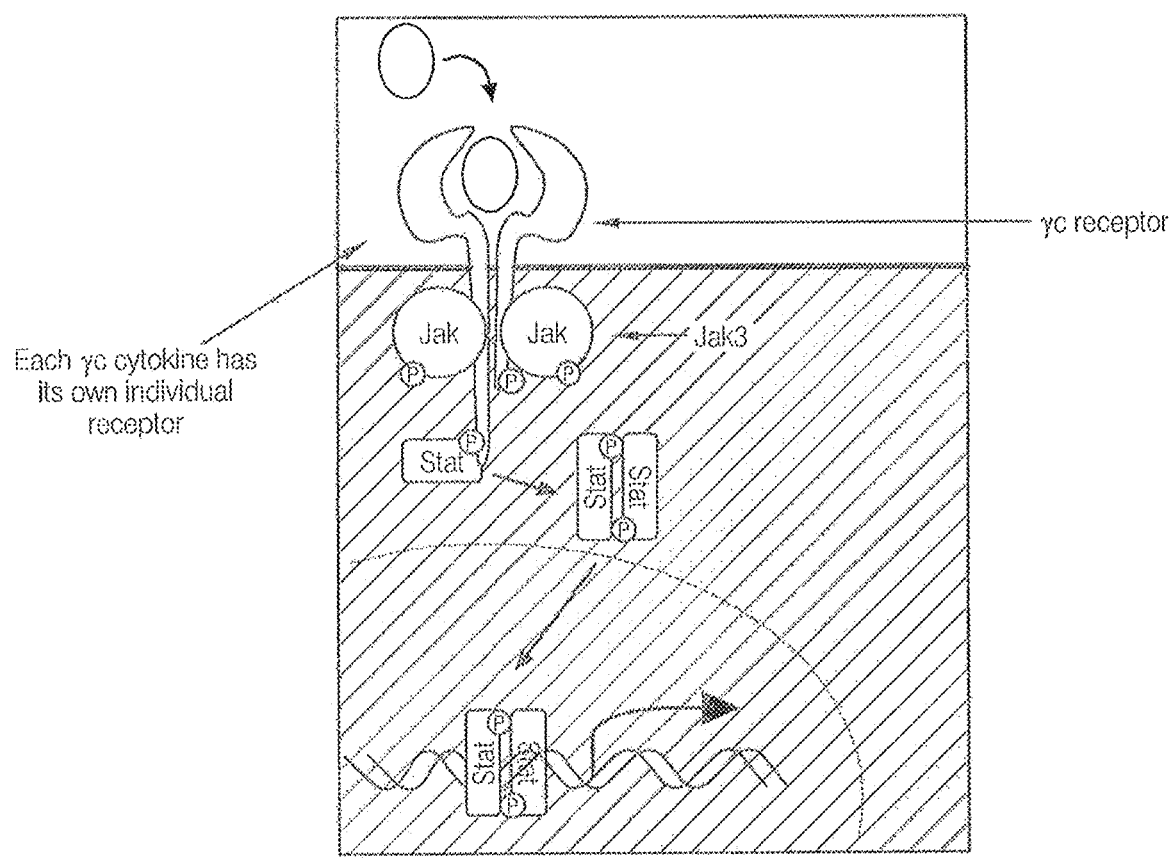
FIG. 5 depicts a gamma(γ)c cytokine ligand bound by its receptor structure to form a ligand-receptor complex, indicating common and cytokine-specific components. The figure presents the schematic representation of the common-gamma family of cytokines.

In an ex vivo spontaneous T-cell proliferation assay, PBMC from HAM/TSP patient was cultured at 1×10(6) cells per well of a 96 well plate in RPMI-10% FCS. Increasing concentrations of BNZ-γ peptide were added to each well. As a control, an irrelevant peptide was used in similar fashion. The cells were incubated in a 37° C. CO2 incubator for 3, 4, and 6 days. The amount of 1 uCi of $^3$H-thymidine was added to the cells. After an additional 6 hour incubation, cells were harvested their proliferation rate was measured. The data for a representative HAM/TSP patient is shown in FIGS. 4A-4D. As indicated in FIG. 4A, BNZ-γ peptide inhibits the spontaneous proliferation of T-cells in HAM/TSP culture at a concentration of about 1 ug/ml.

Other immunological markers were additionally measured in this assay. The percentage of the viral specific CD8 cells was measured during the ex vivo culture using viral protein tetramers. The population of CD4+CD25+ cells, a marker of T-cell activation, as well as Ki67 staining, a marker of T-cell proliferation, was monitored in a flow cytometry assay.

Other forms of the conjugated BNZ-γ peptide derivative can be used in a similar future assay. They include albumin, BSA, PEG that can be conjugated to the peptide after chemical synthesis. Other biological forms of the BNZ-γ peptide conjugate may include regions of known protein entities (including but not limited to Fc region of human IgG) that are fused to the BNZ-γ peptide derivative.

Example 13

Method of Treating Adult T-Cell Leukemia (ATL) in a Human Patient by Administration of Custom Derivative γc-Antagonist Peptide A human patient suffering from Adult T-cell Leukemia is identified. An effective dose, as determined by the physician, of custom derivative γc-antagonist peptide, for example, BNZ-γ is administered to the patient for a period of time determined by the physician. Treatment is determined to be effective if patient enters remission.

Example 14

Method of Treating HAM/TSP in a Human Patient by Administration of Custom Derivative γc-Antagonist Peptide A human patient suffering from HAM/TSP is identified. An effective dose, as determined by the physician, of custom derivative γc-antagonist peptide, for example, BNZ-γ is administered to the patient for a period of time determined by the physician. Treatment is determined to be effective if patient's symptoms improve or if the progression of the disease has been stopped or slowed down.

Ligand-receptor mediated signaling is a major form of signal transduction across cell membranes. Ligand-receptor mediated signaling has been implicated in a number of biological processes, from cellular growth, differentiation and apoptosis, to host pathogen-interactions and disease recognition. Similarly, defects in ligand-receptor signaling have been implicated in a huge number of diseases, leading to substantial interest in targeting ligand-receptor interactions for therapeutic intervention.

Ligand-receptor signaling involves the binding of a ligand to its receptor to form a ligand-receptor complex, which initiates signal transduction across a membrane or, in the case of pathogens, for example, pathogen differentiation or entry into the cell. Disruption of ligand-receptor complex formation, thus, is a potential avenue for disrupting aberrant signaling, or preventing pathogen entry into the cell.

Certain embodiments relate to methods of engineering, designing, and developing peptide antagonists that selectively inhibit more than one cytokine, growth factor, or any ligand that utilizes a receptor to exert its biological activity, for example by inhibiting the formation of a ligand-receptor complex necessary for signaling. These methods and compositions also apply to bacteria, viruses, or their by-products that use hosts' cell surface receptors to enter into the cell or manifest their pathological conditions. The present embodiments also relate to the therapeutics uses of such peptides for the treatment of certain human diseases. Description of the invention, target diseases, therapeutic applications, as well as administration, production and commercialization of the peptides are disclosed.

A major challenge to such a course of action is presented by the fact that ligands, their receptors, or both, often play multiple overlapping roles in signal transduction. As a result, without being bound by theory, it is believed that targeting of a single ligand or receptor is often insufficient to block an aberrant signaling pathway because separate ligands or receptors or both may redundantly or concurrently convey a similar signal. Alternately, blocking of an entire family of structurally related ligand-receptor may interfere not only with an aberrant signaling pathway but with one or more additional signaling pathways, some of which may be essential for cell or organismal survival or health.

As an illustrative example, one may look to the cytokine family of ligands. Cytokines are mediators of the immune response. They are synthesized by a variety of lymphoid and non-lymphoid cells, secreted as soluble proteins, and bind to their unique receptor complexes that are expressed by target cells. Upon the interaction of the cytokine with its receptor, a series of events will occur at the cellular level that carries the signal from the cell surface to the nucleus. The result is cellular activation, proliferation, differentiation or other biological responses that are induced by each cytokine specifically.

The cytokine and cytokine receptor binding is the key event in transferring the signal from the cell surface to the nucleus. This binding is mediated by the interaction of specific amino acid residues that are supported by the three dimensional (3-D) structure of the cytokine. Many cytokines form homo- or hetero-dimmers that provide stable structures to allow the cytokine-receptor interactions. Any element or substance that interrupts the binding of the cytokine and its receptor can act as an antagonist of the cytokine.

The gamma c cytokines utilize JAK (Janus Kinase) and STAT (Signal Transducer and Activator of Transcription) signaling molecules. Upon cytokine-induced activation, JAK recruits and phosphorylates STAT which subsequently translocates into the nucleus where it regulates the expression of numerous genes. It has been well documented that defects in the regulation of some cytokines are associated with immune mediated diseases, which has been the rationale for developing cytokine-directed therapies.

The gamma c cytokines include IL-2, IL-4, IL-7, IL-9, IL-15, and IL-21. Each gamma c cytokine has a unique receptor complex that includes the shared gamma c receptor and each cytokine's private receptor (FIGS. 1A and 1B). The gamma c cytokines have distinct and overlapping functions. IL-2 is a T cell growth factor, augments NK cell cytolytic activity, and promotes immunoglobulin production by B cells. In addition, it contributes to the development of regulatory T (Treg) cells and therefore, peripheral T cell tolerance. IL-2 is involved in T helper 1 (Th1) differentiation, a subset of $CD4^+$ cells that is pivotal for defense against intracellular pathogens, viruses, and inflammatory responses. IL-4 is required for the development and function of Th2 cells, which are generally associated with the humoral immunity. IL-4 also plays a role in allergy and immunoglobulin class switching. IL-7 has a central role in the development of T cells in both humans and mice. In addition, IL-7 is well known for its potent role as a lymphocyte survival factor. IL-9 is produced by a subset of activated CD4+ T cells and induces the activation of epithelial cells, B cells, eosinophils and mast cells. IL-15 is essential for the development of NK cells and homeostasis of CD8+ T cells. IL-21 is involved in generating Th17 response, a response that is central in host defense against virus and bacteria as well as in the development of autoimmune diseases. IL-21 has broad actions that include promoting the terminal differentiation of B cells to plasma cells, cooperating with IL-7 or IL-15 to drive the expansion of CD8+ T cell populations and acting as a pro-apoptotic factor for NK cells and activated B cells.

It has been shown that IL-2, IL-9 and IL-15 are contributing factors in the pathogenesis of diseases such as HAM/TSP, Rheumatoid arthritis, uveitis, organ transplant as well as other autoimmune diseases. Similarly, it has been shown that Th2 pathway is involved in inflammatory reactions in asthma. An antagonistic peptide that can selectively inhibit IL-4 and IL-21 will be of therapeutic value in treating this disease. Similarly, it has been well-documented that IL-15 and IL-21 are central in inflammatory bowel disease (IBD), providing a case for selective inhibition of these two cytokines.

Because of their importance in various immune-mediated diseases, cytokine or cytokine receptor therapy has been used for clinical purposes. Indeed there are many antibodies that target cytokines or cytokine receptors. The limitation to single antibody therapy is the fact that in the majority of the immune-mediated diseases there is more than one cytokine that is the culprit to the disease pathogenesis. Therefore there is a need to develop strategies that inhibit more than one cytokine.

There have been at least two approaches for developing anti-cytokine therapeutics. One approach uses monoclonal antibodies (mAB) that target the cytokines or their receptors. An example of a mAB used in ligand-receptor based therapy is the anti-IL-2 receptor mAB that inhibits T-cells activation. Another approach involved targeting signal transduction molecules that are key to cytokine pathways. This is usually done by identifying small molecules that impact signaling pathways that are common among two or more cytokines. An example of this class of molecules consists of small molecule inhibitors of JAK3, a downstream signaling component for gamma-c cytokines.

Although each approach is scientifically rational, neither is without limitation. A common issue with mAB therapy is that inhibiting one cytokine pathway with a single mAB is not effective at blocking all of the aberrant signaling. This is due to a high degree of functional redundancy in cytokine families. For example, in case of the gamma-c cytokines (FIG. 1A), there are 6 cytokines that have unique and yet overlapping biological functions. This means that inhibiting, for example, IL-2 alone may not be sufficient to block the activation of T-lymphocytes since IL-15 and IL-7 have similar effects on these cells.

According to present theories of cytokine signaling, a fully effective inhibition may require blocking of at least 3 cytokine pathways simultaneously using three different mABs. Although scientifically rational, cocktail mAB therapy is often expensive and may be difficult to implement because of the challenges of obtaining regulatory approval for multiple active components in a single treatment regime.

An alternative approach is the use of small molecules that target signaling pathways such as JAK3. This approach has the advantage of inhibiting multiple pathways. However, implementing this strategy is also not without challenges.

For example, there is concern that inhibition of JAK3 or JAK3 signaling pathway generally will block the biological activity of all the six gamma-c cytokines. As these cytokines mediate the cellular and humoral response, there is a concern that intervention on this level may have a broader impact than desired. That is, their complete blockade may result in undesired side effects. In support of these concerns, it is observed that mice and humans having certain alleles of gamma-c receptors or JAK3 are completely immune-compromised—that is, those mice lack T–, B– and NK cells and those humans lack T– and NK– cells. This, one may observe, is a major deleterious side effect in many instances.

In addition, it has been reported that JAK3 inhibitors may not be specific to JAK3 and instead may block other JAKs such as JAK1 and JAK2. JAK cross-family suppression may impair pathways other than those mediated by the gamma-c cytokines, such as IL-6 and interferon mediated signaling pathways, which may further exacerbate the signaling side effects by blocking these molecules. In support of this hypothesis, it has been observed that a great degree of toxicity as well as anemia, neutropenia, and multiple infections is associated with some small molecule JAK3 inhibitors.

These concerns are likely general to pharmaceutical interventions targeting ligand-receptor signaling. That is, most ligands, most receptors, and many downstream effectors of ligand-receptor signaling are members of multi-component families whose members may perform partially overlapping, totally overlapping or distinct signaling functions. As a result, there is unlikely to be a clear correspondence between the targeting of a single ligand-receptor interaction and the remedial perturbation of signaling such that an aberrant signaling pathway is corrected or the associated negative phenotype is resolved through the perturbation of a single ligand-receptor interaction.

Disclosed herein include methods and compositions for the selective, targeted inhibition of more than one ligand-receptor interaction. The methods and compositions disclosed herein have the advantage of inhibiting more than one ligand-receptor interaction and therefore may be more effective than single mAB therapy at addressing a signaling-associated condition. The methods and compositions disclosed herein also have the advantage of exquisite specificity in the ligand-receptor interactions which they target, resulting in a minimization of secondary signaling side effects or, ultimately, toxicity.

Through practice of the methods disclosed herein, multiple ligand-receptor interactions within a single ligand-receptor family may be targeted, for example using a single molecule such as a polypeptide that specifically and selectively blocks ligand-receptor interacting regions on multiple ligands and receptors. The goal is to inhibit the cytokines that are disease drivers and not the ones that are not relevant to the disease.

This method comprises identifying amino acid regions in a closely related ligand-receptor family that share a common receptor. These amino acid regions are involved in ligand-receptor binding or in receptor assembly of each ligand if the ligand's receptor complex is comprised of multiple receptor subunits. See, for example, FIG. 5. Identifying the amino acid sequences may be conducted using tools such as amino acid sequence data bases and protein software programs that can predict the structure and binding of the cytokine to the receptor, and crystal structure studies of the ligand and its receptor. Using methods described here, a specific example is provided for designing BNZ132-1, one can design peptides that can specifically block the binding interface of some of the ligands to the shared receptors. As the result, the inhibitory peptide can selectively inhibit the function of some ligands but not all of them. Ligand or receptor targets include but are not limited to cytokines and cytokines and cytokine receptors, chemokines and chemokine receptors, viral receptors such as CCR5, CXCR4, Claudin-1, HAVCR-1, CD81 tetraspanin, carboxypeptidase D, HBVCR-1, TIM-1, or their ligands such as HIV proteins gp120 or gp41, or a West Nile ligand, a hepatitis virus ligand or receptor, pathogen receptors such as Basigin (CD147), Semaphorin-7A (CD108), chondroitin sulfate A (CSA), DC-SIGN, Complement receptor type 3 (CR3) or other ligands or receptors.

The methods disclosed herein may be practiced using one or more of the following steps. Individual steps may be excluded or practiced in an order other than that presented below.

One may select at least two ligand-receptor interactions which are to be disrupted, or ligands which are to be blocked, or receptors which are to be blocked. Selection may be based upon experimental evidence suggesting a common role in a signaling pathway to be disrupted. Evidence may be newly generated or gleaned from the scientific literature or may be based upon one or more additional independent criteria.

Polypeptide sequences of each ligand or receptor to be targeted are determined. Polypeptide sequences may be determined using any number of approaches and the methods herein are not limited by how the polypeptide sequences are determined. Polypeptides may be sequenced directly using polypeptide sequencing chemistries known to one of skill in the art; or polypeptide sequences may be inferred from the polynucleic acid sequences which encode them, sequenced using nucleic acid sequencing chemistries known to one of skill in the art; or the polypeptide or polynucleotide sequences may be previously generated and made available, for example at a database such as the national center for biotechnology information (ncbi.nlm.nih.gov) or an international or other U.S. equivalent, for example embl.org, eupathdb.org/eupathdb/, jgi.doe.gov/, or other source.

Antagonist peptide sequences may be designed by studying and analyzing the crystal structure of the receptor(s) and ligand which will determine the key amino acids in binding of the ligand and the receptor, or alternatively by using protein design software known to the skilled to the art that include but not limited to the followings:

1) Chimera Software cgl.ucsf.edu/chimera/

2) Pep Fold for peptide folding studies bioserv.rpbs.univ-paris diderot.fr/services/PEP-FOLD/3)Protein Folding Studies swissmodel.expasy.org/

4) Patchdock for protein and peptide docking studies bioinfo3d.cs.tau.ac.il/PatchDock/

5) Fire Dock for protein and Peptide docking studies bioinfo3d.cs.tau.ac.il/FireDock/

Using these software, the skilled person in the art can predict the binding sites of the ligand to the receptor. Furthermore, the same software can be used to determine the structure of the peptide and its binding sites with the receptor.

A region within at least one ligand or receptor to be targeted for specific inhibition is identified. A region may be identified on the basis of direct involvement with a ligand-receptor interaction (a region of a ligand that contacts a receptor or a region of a receptor that contacts a ligand). A region may also be identified on the basis of a supplementary interaction that is necessary for signaling, such as an interaction among receptor components that is necessary to assemble a functional receptor, or an interaction between a receptor such as a ligand-bound receptor and a downstream signaling component.

Other bases for region selection are contemplated. In some embodiments regions are selected based in part or wholly upon accessibility of the region to an aqueous environment such as the exterior of a cell or the interior of a cell. In some embodiments regions are selected based in part or wholly on the presence of sequence similarity among ligand or receptor family members, such as sequence similarity which suggests a common secondary structure, sequence similarity which allows for some sequence which is specific to one, more than one, or each individual ligand or receptor to be identified, or sequence similarity which suggests a common secondary structure and which allows for some sequence which is specific to one, more than one, or each individual ligand or receptor to be identified. In some embodiments regions are selected based on the amino acid sequences of the common receptor that is required for the assembly of the entire receptor complex. For example, gamma-c receptor needs to interact with the alpha-receptor subunit of IL-7, IL-21 or IL-4, or the beta subunit of IL-2, to form a fully functional receptor. The antagonist peptide may block the region that is required to bring all the receptor subunits together.

Information regarding region selection may be determined experimentally, inferred from in silico analyses of sequence alignments, or obtained from the scientific literature or other source.

In some embodiments regions are selected such that the region spans sequence unique to each individual ligand or receptor to be disrupted. In some embodiments a region is selected wherein one, two, more than two, or all of the ligands or receptors to be disrupted share a common sequence or sequence fragment that is distinct from the sequence within the selected region of one, more than one, or all of the non-targeted ligands or receptors. In some embodiments a region is selected wherein one, two, more than two, or all of the ligands or receptors to be disrupted share a sequence fragment that is also found in one, more than one, or all of the non-targeted ligands or receptors.

Once conserved regions are identified, such as regions involved in ligand-receptor interactions, for example, sequence fragments corresponding to each ligand or receptor are identified and assembled into a single inhibitor polypeptide. The polypeptide assembled is a composite sequence of sequence fragments of the binding sites of each ligand, and comprises sequence fragment selected from the ligands or receptors to be inhibited. In some embodiments the sequence fragments are selected such that the overall secondary structure of the assembled polypeptide does not differ substantially from that of at least one individual ligand or receptor the activity of which is to be inhibited. In some embodiments, the sequence fragments are selected such that the overall secondary structure of the assembled polypeptide does not differ substantially from that of any of the individual ligands or receptors the activity of which is to be inhibited.

An individual sequence fragment may comprise 10, 9, 8, 7, 6, 5, 4, 3, 2, or even 1 polypeptide residue of a single target ligand or receptor. An interfering polypeptide sequence may comprise 6, 5, 4, 3, 2, or 1 sequence fragment of a single target ligand or receptor. An assembled polypeptide composite sequence may comprise a total of 20, 19, 18, 17, 16, 15, 14, 13, 12, 11, 10, 9, 8, 7, 6, 5, 4, 3, 2, or 1 residue total from a single target ligand or receptor. Of the residues from a single target ligand or receptor, of 20, 19, 18, 17, 16, 15, 14, 13, 12, 11, 10, 9, 8, 7, 6, 5, 4, 3, 2, or 1 residue total may be unique to that single target ligand or receptor.

In some embodiments an individual sequence fragment consists exclusively of a sequence of residues that is unique to a single target ligand or receptor at its position within a family of target ligand or receptor sequences. In some embodiments an individual sequence fragment comprises at least one residue which is shared in common at its position within a family of target ligand or receptor sequences. In some embodiments an individual sequence fragment comprises sequence which is common to at least two polypeptide targets. In some embodiments individual sequence fragments may overlap with one another, or comprise subsets of one another.

In some embodiments the total number of residues of the inhibitor polypeptide is equal to the total number of residues of the identified conserved region of one of the ligands or receptors. In some embodiments the total number of residues of the inhibitor polypeptide differs by 1, 2, 3, 4, 5, 6, 7, 8, 9, 10 or more than 10 residues from the total number of residues of the identified conserved region of one of the ligands or receptors. In some embodiments the total number of residues of the inhibitor polypeptide differs by less than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75% or a greater percent from the total number of residues of the identified conserved region of one of the ligands or receptors.

In some embodiments the position of an individual sequence fragment is conserved with regard to its position in the polypeptide from which it is drawn and its position in the inhibitor polypeptide into which it is incorporated. That is, an individual sequence fragment that spans residues 'x' to 'y' of a conserved target region of a target polypeptide may similarly span residues 'x' to 'y' of the inhibitor polypeptide of which it is a part. For example, an individual sequence fragment that spans residues 5-8 of the conserved target region of a target polypeptide may also span residues 5-8 of the inhibitor polypeptide to which it is incorporated.

In some embodiments an individual sequence fragment that spans residues 'x' to 'y' of a conserved target region of a target polypeptide may span residues 'x+1' to 'y+1', 'x+2' to 'y+2', 'x+3' to 'y+3', 'x+4' to 'y+4', 'x−1' to 'y−1', 'x−2' to 'y−2', 'x−3' to 'y−3', 'x−4' to 'y−4', or a region less correspondent to its position in a conserved target region of a target polypeptide in the inhibitor polypeptide. In some embodiments the relative position of an individual sequence fragment with respect to the conserved target region of a target polypeptide from which it is selected may be preserves relative to other individual sequence fragments from the conserved target region of a target polypeptide from which it is selected or from the conserved target region of a target polypeptide other than that from which it is selected.

In some embodiments an inhibitor polypeptide is assembled from a plurality of individual sequence fragments such that the positions of the individual sequence fragments within the inhibitor polypeptide corresponds to the position of each individual sequence fragment within the conserved regions of the polypeptides from which it is drawn.

Figure 6:
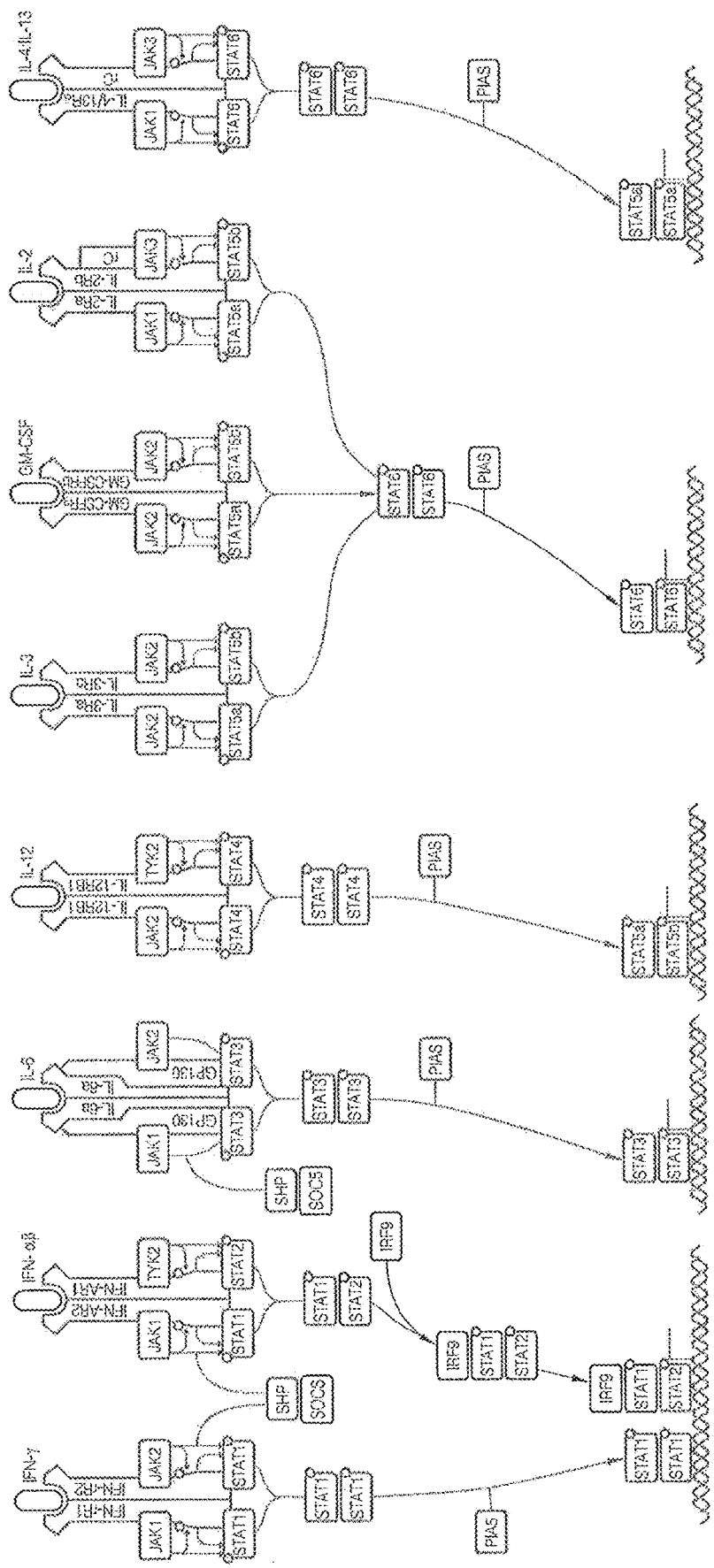
FIG. 6 depicts various cytokine families where there is a shared receptor and signaling pathway. The figure presents the schematic representation of various cytokine and cytokine receptors.

The 'assembly' of a plurality of individual sequence fragments into an inhibitor polypeptide may be literal or conceptual. One may, for example, cleave a number of polypeptide conserved regions, isolate actual individual sequence fragments, and bind the desired fragments into a single inhibitor polypeptide. As a more likely alternative, one may synthesize or assemble a nucleic acid encoding an inhibitor polypeptide having an amino acid residue sequence which comprises individual sequence fragments, such as individual sequence fragments positioned as indicated above, and use the nucleic acid directly or indirectly to specify the incorporation of amino acids into a polypeptide, for example through ribosomal translation. As yet another alternative, an inhibitor may be synthesized de novo using chemical means of polypeptide formation using the conceptually determined sequence as a guide to synthesis.

An inhibitor polypeptide may be tested in an assay to demonstrate its activity. For example, a suitable cell line may be isolated having as a characteristic a requirement for a given ligand-receptor interaction to be present and active to drive growth. CTLL-2 cells, for example, require IL-2 for growth and proliferation in vitro, and their proliferation in the presence of an inhibitor polypeptide comprising IL-2 individual sequence fragments may be an output through which to measure inhibitor activity. If a dose-dependent inhibition by the peptide is observed, then it means that the peptide has antagonistic activity against this cytokine.

Additional tests of inhibitor polypeptide efficacy are also contemplated. Downstream constituents of a signaling pathway involving a ligand-receptor interaction, such as an immediate downstream kinase substrate may be used in a test of inhibitor polypeptide efficacy. A constituent further removed from the ligand-receptor interaction, such as a gene, the expression of which is regulated specifically by the ligand-receptor interaction, may also be representative of inhibitor polypeptide efficacy and therefore useful in a test for inhibitor of polypeptide efficacy. If, for example, a dose-dependent inhibition by the peptide is observed, then it means that the peptide has antagonistic activity against this ligand or receptor.

An inhibitor polypeptide may be optimized using a number of methods, many of which are known to one of skill in the art. Optimization may comprise site-directed mutagenesis, alanine scanning (sequential substitution of individual residues with alanine), proline scanning or saturation mutagenesis, whereby individual residues or combinations of residues are altered and the resulting polypeptide is compared to the original inhibitor polypeptide with respect to one or more characteristics. The original amino acids may be replaced by other natural or unnatural amino acids to enhance the stability or affinity of the peptide. The original amino acids may also be replaced with D-amino acids, for example to prevent proteolytic cleavage. Furthermore, the peptide amino acid sequence may be modified to turn it into a cyclic amino acid while preserving its biological function. Optimization using 'post-translational' modifications to a polypeptide, such as glycosylation, phosphorylation, addition of a fatty acid group, cyclization or other polypeptide modification known to one of skill in the art is also contemplated.

Inhibitor polypeptides may optionally be optimized to improve their binding affinity to a target receptor or receptors, or ligand or ligands; or to improve their stability; or to decrease non-target binding; or to improve their solubility; or to facilitate administration to a subject, for example.

Once a lead inhibitor peptide is identified and optionally optimized then it may be further modified to facilitate its use as a medicament, for example by conjugation to a moiety such as PEG (polyethylene glycol), a carbohydrate moiety, albumin or an antibody fragment or other protein or non-protein structures.

As a further detailed discussion of the compositions and methods disclosed herein, one may take as an example the implementation of the selected members of the cytokine ligand-receptor family, both to identify general aspects of the method and to identify family-specific elements.

Cytokines are a diverse group of soluble factors that mediate various cell functions, such as, growth, functional differentiation, and promotion or prevention of programmed cell death (apoptotic cell death). Cytokines, unlike hormones, are not produced by specialized glandular tissues, but can be produced by a wide variety of cell types, such as epithelial, stromal or immune cells. More than 100 cytokines have been identified so far and are considered to have developed by means of gene duplications from a pool of primordial genes (Bazan, J. F. 1990, Immunol. Today 11:350-354, which is incorporated by reference herein).

In support of this view, it is common for a group of cytokines to act as ligands for multi-subunit receptor complexes which share one or more components.

The most well-documented shared cytokine subunit in T cells is the common gamma subunit (gamma c-subunit). The gamma c-subunit is shared by 6 known cytokines (Interleukin-2 (IL-2), Interleukin-4 (IL-4), Interleukin-7 (IL-7), Interleukin-9 (IL-9), Interleukin-15 (IL-15), and Interleukin-21 (IL-21), collectively called the "gamma c-cytokines" or "gamma c-family cytokines") and plays an indispensable role in transducing cell activation signals for all these cytokines. Additionally, for each of the gamma c-cytokines, there are one or two cytokine-specific receptor subunits that when complexed with the gamma c-subunit, give rise to a fully functional receptor. (Rochman et al., 2009, Nat Rev Immunol. 9: 480-90, which is incorporated by reference herein).

The gamma c-family cytokines are a group of mammalian cytokines that are mainly produced by epithelial, stromal and immune cells and control the normal and pathological activation of a diverse array of lymphocytes. These cytokines are involved in early development of T cells in the thymus as well as their homeostasis in the periphery. For example, in the absence of the gamma c-subunit, T, B and NK cells do not develop in mice. (Sugamura et al., 1996, Annu. Rev. Immunol. 14:179-205, which is incorporated by reference herein).

To identify cytokine-receptor binding sites, one may focus on a family of cytokines. A common feature in cytokines families is a great degree of redundancy within the cytokine family members. This is due to the fact that the cytokines in a family share a common receptor (such as the gamma-c receptor in FIGS. 1A and 1B). Each cytokine has its own specific receptor constituent such as IL-2R-alpha that gets recruited and forms a unique cytokine receptor complex. The unique receptor complex renders specific functions for each cytokine. However each cytokine in the family is using a common receptor and common signaling molecule (such as the gamma-c receptor and JAK3 signaling molecule), thus they show overlapping functions.

FIG. 6 illustrates only some of the cytokine families each having a shared receptor and signaling pathway. The IL-17 family is also emerging as a cytokine family with a shared receptor IL-17RA.

In identifying a target region for inhibition, one may start from a cytokine family and studying what is known in the literature about their structure—activity—relationship (SAR). Information regarding SAR may be determined experimentally, inferred from in silico analyses of sequence alignments, or obtained from the scientific literature. Usually there is one cytokine in a given family for which sufficient information is available to identify a target region. Once a target region is identified in a member of a given family, one can deduce similar SAR for the rest of the cytokine family and predict the key amino acids that interact with the receptor.

It is well established that many cytokines (including many interleukins, growth hormones, prolactin, granulocyte-macrophage colony-stimulating factors (G-CSF and GM-SCF, EPO), as well as interferons belong to a super family called helical cytokines. Despite the fact that they do not have typical similarities in amino acid sequence, the common denominator among the helical cytokines is that they comprise bundled alpha-helices. The structure and motifs of these helices within each family is conserved, which allows one to predict the binding sites between each cytokine and the common receptor. Although IL-1 and some interleukins do not show this helical-bundle structure, it is quite common among many cytokines for which structural information is available.

In the following section, some non-limiting and illustrative examples of how such antagonist peptides are designed to selectively inhibit only a subset of cytokines that share a common receptor but not all of them are provided. Similar strategies can be used to design other antagonist peptides to inhibit different set of ligands within a given family.

What is disclosed herein comprises a method that targets the shared receptor subunits that is utilized by several cytokines and selectively inhibits multiple members within that family. For the purpose of illustration, an illustrating and non-limiting examples disclosed herewith focused on the γc family of cytokines as a model for evaluating the emerging concept of "selective inhibition of multiple cytokines." The same technology however can be utilized for other cytokine families, such as IL-6 and IL-17 family, where several cytokines share a common receptor.

Many cytokines may assume a distinct four-helical bundle structure. "Pleiotropy" and "Redundancy", two characteristics of cytokines, are partly due to the sharing of receptor and signaling components among multiple cytokines, which is the basis for family clustering of cytokines. Examples include the IL-6 family which uses the gp130 molecule, the γc-family (IL-2, -4, -7, -9, -15, and -21) using γc, and the IL-3 family which uses the common 3 molecule. The γc-cytokines control normal immune responses as exemplified by defects in immune functions of knockout mice or humans lacking individual γc-cytokines, receptor or signaling components. Moreover, each γc-cytokine is connected with various immune and inflammatory diseases in humans. IL-2 has been implicated in inflammatory bowel diseases (IBD). IL-4 has been implicated in Asthma. IL-7 has been implied in multiple sclerosis, ulcerative colitis, and sarcoidosis. IL-9 and has been implicated in Allergic inflammation and in Asthma. Over-expression of IL-15 in mice and in humans is associated with T/NK leukemia. IL15 has been also implicated in Celiac disease. IL-21 is a recent addition and involved in the differentiation of B and follicular helper T cells, which has been implicated in IBD, Celiac disease, psoriasis, atopic dermatitis, systemic lupus erythmatosus (SLE), multiple sclerosis (MS) and type I diabetes.

Recent reports demonstrate cases of human diseases that involve more than one cytokines, in particular those from a family. See Table 1 below.

TABLE 1

List of human diseases in which γc-cytokines are disease drivers

| Disease | Cytokines | References |
| --- | --- | --- |
| HAM-TSP | IL-2, IL-15, (IL-9?) | 1-7 |
| Celiac Disease/IBD (inflammatory bowel disease) | (IL-2), IL-15, IL-21 | 8-14 |
| Uveitis | IL-2, IL-21 | 15-17 |
| Asthma/COPD (chronic obstructive pulmonary disease) | IL-4, IL-9, IL-5, IL-13 | 18-30 |
| MS (multiple sclerosis) | IL-2, IL-9, IL-15, IL-21 | 31-38 |
| RA (Rheumatoid Arthritis) | IL-7, IL-15, IL21, IL-6 | 39-48 |

Treatment of these cases is challenging to the current single anti-cytokine strategy utilizing monoclonal antibodies (one specific target) or chemical inhibitors that block cytokine signaling such as JAK3 inhibitor (many targets with less specificity). Therefore, the methods disclose herein provide an embodiment in which more than one cytokine can be inhibited in a selective manner.

Targeting the Interface of the Common Receptor and Multiple Cytokine Interactions.

This particular, non-limiting example provided herein focused on the γc family of cytokines (IL-2, IL-4, IL-7, IL-9, IL-15, and IL-21) and intended to design a peptide that inhibits primarily IL-2 and IL-15 while the rest of the cytokines in this family would be unaffected. First, the available structural information on these molecules was collected. Residues of IL-2 or IL-15 that are involved in the cytokine-receptor interaction have been identified and the D-helix (last of the four α-helices) in each cytokine primarily interacts with γc. Consistently, the primary structures of γc-cytokines show highest degree of conservation in the D-helix across mammalian Tables 2 and 3.

TABLE 2

| IL-2 homology matrix | | | | | | | |
| --- | --- | --- | --- | --- | --- | --- | --- |
| Primate | 68.1/100 | | | Primate | 29.1/100 | | |
| Mouse | 27.8/67 | 27.8/67 | | Mouse | (—)/16.7 | (—)/21.3 | |
| Bovine | 24.8/80 | 24.8/80 | 21.4/78 | Bovine | 18.9/75 | 19.7/62 | (—)/14.3 |
| Primate | 71/100 | | | Primate | 67.7/100 | | |
| Mouse | 32/77 | 32/77 | | Mouse | 50.3/78 | 50.3/78 | |
| Bovine | 46.9/95 | 46.9/84 | 16.8/60 | Bovine | 52/88 | 52/88 | 37.7/71 |

TABLE 3

Human Cytokine homology matrix

| | | | | | | | | | | | |
|---|---|---|---|---|---|---|---|---|---|---|---|
| IL-4  | 10   |      |      |      |      | IL-4  | 12.5 |      |      |      |    |
| IL-7  | 15   | **   |      |      |      | IL-7  | 9.1  | 12.5 |      |      |    |
| IL-9  | 14.3 | 15.4 | 14.3 |      |      | IL-9  | 18.8 | 20.8 | **   |      |    |
| IL-15 | 10   | 15.8 | 5.3  | 15.6 |      | IL-15 | 27.7 | 4.2  | 16.7 | 13.3 |    |
| IL-21 | 18.2 | 9.1  | 13.6 | 13.6 | 13.6 | IL-21 | 33.3 | 12   | 8.3  | 33.3 | 15.4 |
| IL-4  | 13.6 |      |      |      |      | IL-4  | 27.3 |      |      |      |    |
| IL-7  | 17.4 | 45   |      |      |      | IL-7  | 20   | 20.6 |      |      |    |
| IL-9  | 13.6 | 17.7 | 15   |      |      | IL-9  | 15   | 22.7 | 23.5 |      |    |
| IL-15 | 20   | 5    | 9.5  | 15   |      | IL-15 | 22.2 | 11.1 | 20.6 | 20   |    |
| IL-21 | 18.2 | 22.2 | 10   | 11.8 | 20.8 | IL-21 | 28.6 | 18.2 | 11.8 | 23.8 | 28 |

The alignment of D-helices from human γc-cytokines (T-coffee algorism) demonstrated a mildly conserved motif within this region, which is named as the γc-box (FIG. 8A). Also an additional short motif (the IL-2/15-box, FIG. 8B) between IL-2 and IL-15 (IL-21 also included, albeit weakly) was noticed and this is consistent with the notion that IL-2 and IL-15 share IL-2/IL-15Rβ besides γc and form a sub-family in the γc-family.

Although the 3D-structures of the D-helices from IL-2 and IL-15 are almost identical and superimposable, fine chemical differences exist in their binding to γc. It was hypothesized that by leveraging differences in the primary structures, one would be able to design an inhibitor peptide that equally inhibits IL-2 and IL-15.

The alignment of D-helices from human γc-cytokines (T-coffee algorism) demonstrated a mildly conserved motif within this region, which is named as the γc-box (FIG. 8A). Also an additional short motif (the IL-2/15-box, FIG. 8B) between IL-2 and IL-15 (IL-21 also included, albeit weakly) was noticed and this is consistent with the notion that IL-2 and IL-15 share IL-2/IL-15Rβ besides γc and form a sub-family in the γc-family.

Although the 3D-structures of the D-helices from IL-2 and IL-15 are almost identical and superimposable, fine chemical differences exist in their binding to γc. It was hypothesized that by leveraging differences in the primary structures, one would be able to design an inhibitor peptide that equally inhibits IL-2 and IL-15.

Based on these information, the peptides that could target the binding interface(s) of γc with IL-2 and IL-15 with the following characteristics were designed: 1; such peptide(s) would form a helical structure, similar to the native D-helices of IL-2 and IL-15, 2; it would contain key aa responsible for the binding of each cytokine to γc, 3; the composite sequence should be derived nearly equally from IL-2 and IL-15, respectively (minimum bias to either cytokine). Of the 120 peptides (FIGS. 9A, 9B, and 9C) that were designed and screened by a computer docking simulation (FIGS. 9D-9H) showed proper docking. They were synthesized and tested for inhibition on IL-2 and IL-15.

In FIG. 8A, alignment of amino acid sequences of six γc cytokines at helix D is provided. The γc box, which is a mildly conserved motif between all γc cytokines, is marked. FIG. 8B shows that IL-2/15 Box is an extended homologous region between IL-2 and IL-15 at the C-terminus. In both figures, the marker (e.g. "*", "", "*", "•", and "••") represents the chemical properties of the amino acids (i.e. the same marker means shared chemical property). In FIG. 8C, the BNZ132-1 peptide derived from IL-2 and IL-15 amino acid sequences is provided and the BNZ132-1 peptide comprises key amino acids from both cytokines that interact with the γc subunit. The sequences of other peptides are demonstrated in FIG. 9A.

FIG. 9A shows rational evolution of γc-inhibitory peptide sequence leading to BNZ132-1. A previous literature (A. M. Ring et al., "Mechanistic and structural insight into the functional dichotomy between IL-2 and IL-15", 2012, Nature Immunology 13, PP.: 1187-1195, which is incorporated by reference herewith) provided a 3D structure of IL-2 and IL-15 in complex with the receptor subunits (a, b and γc). In particular, a detailed information has been suggested as to which amino acid (aa)s of each cytokine are intimately involved in the interaction of the cytokine with the γc-sub-unit. Based on this information, an embodiment of the peptide design methods disclosed herein may have proceeded based on the following criteria;

1—the peptide would assume the a-helical structure, similar to those of IL-2 and IL-15;

2—the peptide would contain equal numbers of amino acids from IL-2 and IL-15 which have been implicated in the interaction with the γc subunit; and 3—the total number of aa derived from IL-2 and IL-15 would be almost equal in the peptide.

Each peptide was synthesized and tested in CTLL2 assay. BNZ132-1 was confirmed that it inhibited IL-2 and IL-15 with an equal efficacy. BNZ132-1 (FIG. 6A) was finally chosen as it showed equal potency in inhibiting IL-2 and IL-15.

Inhibition of IL-2 and IL-15 by BNZ132-1

Next, it was reconfirmed that BNZ132-1 efficiently inhibits IL-2 and IL-15 using murine CTLL-2 cells (a standard cell line to test human IL-2 and IL-15), as shown in FIGS. 10A-10E. This is the first example of a single peptide equally blocking two cytokines from a family.

Figure 10A:
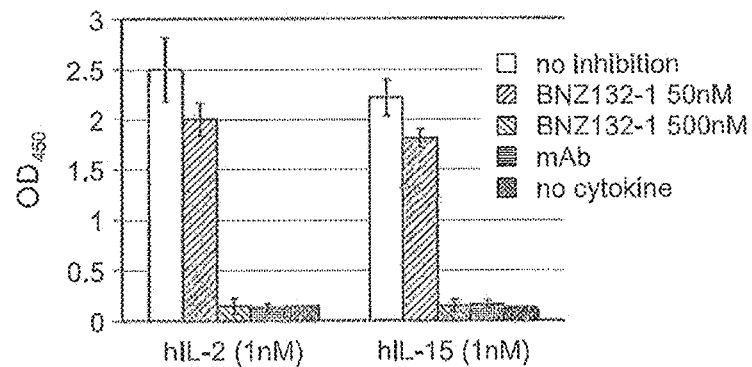

FIG. 10A shows the results of CTLL2 proliferation assay (BNZ132-1 vs. IL-2 and IL-15). Cells were washed and incubated with IL-2 (I nM), IL-15 (I nM) in the presence or absence of BNZ132-1 (50 and 500 nM) or mAB against the cytokine (5 mg/ml) for 24 hrs. Cells were then pulsed with the WST-1 reagent to measure the proliferative response for the next 6 hr ($OD_{450}$).

Figure 10B:
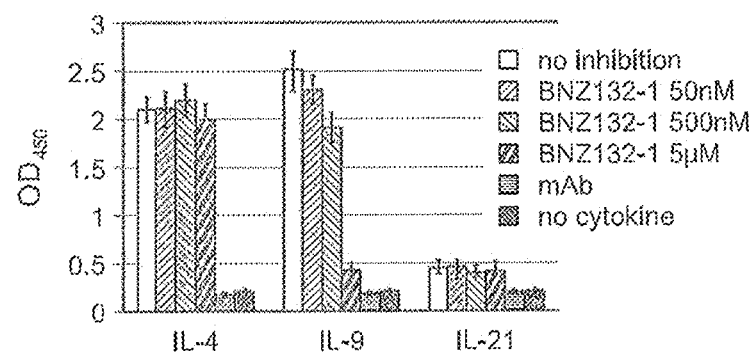

FIG. 10B shows the results of PT18 proliferation assay (BNZ1321-1 vs. IL-4, -9, and -21). Cells were washed and incubated with IL-4 (5 nM), IL-9 (I nM), IL-21 (5 nM) in the presence or absence of BNZ132-1 (50 nM~5 mM) or mAB against each cytokine (5 mg/ml) for 24 hours. vCells were pulsed with WST-1 reagent for the following 6 hr to measure $OD_{450}$.

Figure 10C:
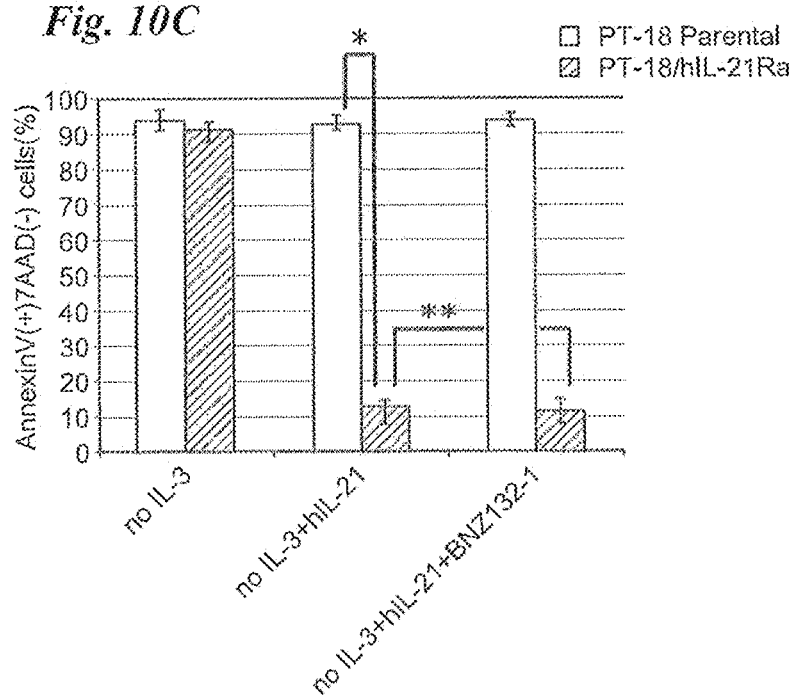

FIG. 10C shows the results of. Apoptosis assay by Annexin V staining (BNZ 132-1 vs. IL-21). A PT-18 sub-clone that expresses human IL-21Rα was established (FIGS.

11A and 11B). The clone did not show robust proliferative response to IL-21. However, IL-21 protected the cells from undergoing apoptosis after IL-3 withdrawal (*, p<0.001). BNZ132-1 did not counteract the effect of IL-21 in preventing the apoptotic death of PT-18 caused by the withdrawal of IL-3 (** p>0.05).

Figure 10D:
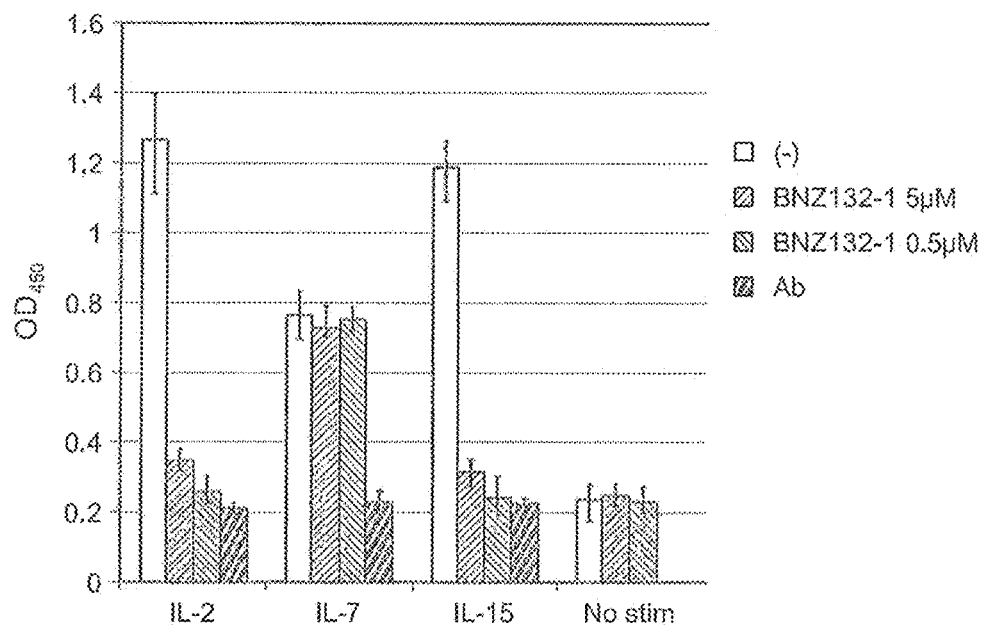

FIG. 10D shows the results of Human peripheral T-cell proliferation assay (BNZ132-1 vs. IL-7). Peripheral T-cells were obtained from a healthy donor. The cells were stimulated by PHA (0.5 ug/ml) for 48 hr, then expanded by 0.5 nM IL-2 for 4 days (CD3>95%). Cells were washed of IL-2, then re-stimulated by 1 nM IL-2, 5 nM IL-7, or 1 nM IL-15 in the presence of BNZ132-1 or specific neutralizing mAb against the cytokine. After 36 hr, WST-1 reagent was pulsed to measure proliferation for the following 12 hr.

Figure 10E:
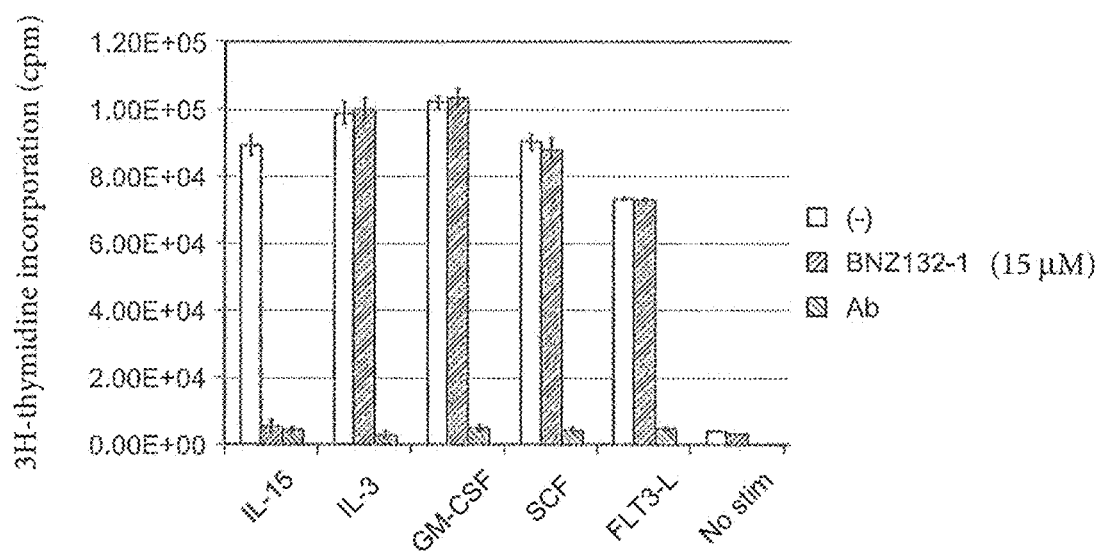

FIG. 10E shows the results of PT-18 proliferation assay in response to non-gc cytokines. PT-18 cells naturally respond to an array of non-γc cytokines including IL-3, GM-CSF, SCF, and Flt3-L. BNZ132-1 did not inhibit any of the cytokines even when used at an excess (15 mM) dose. A neutralizing mAB against each cytokine completely inhibited the proliferation (controls).

Figure 11A:
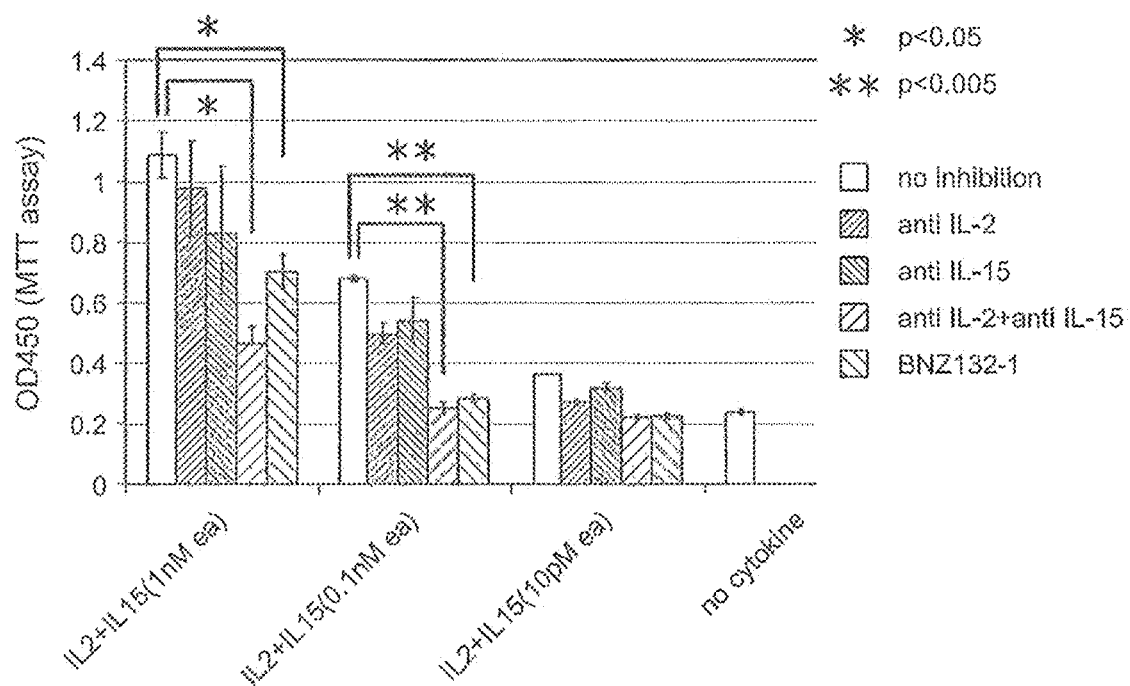
Figure 11B:
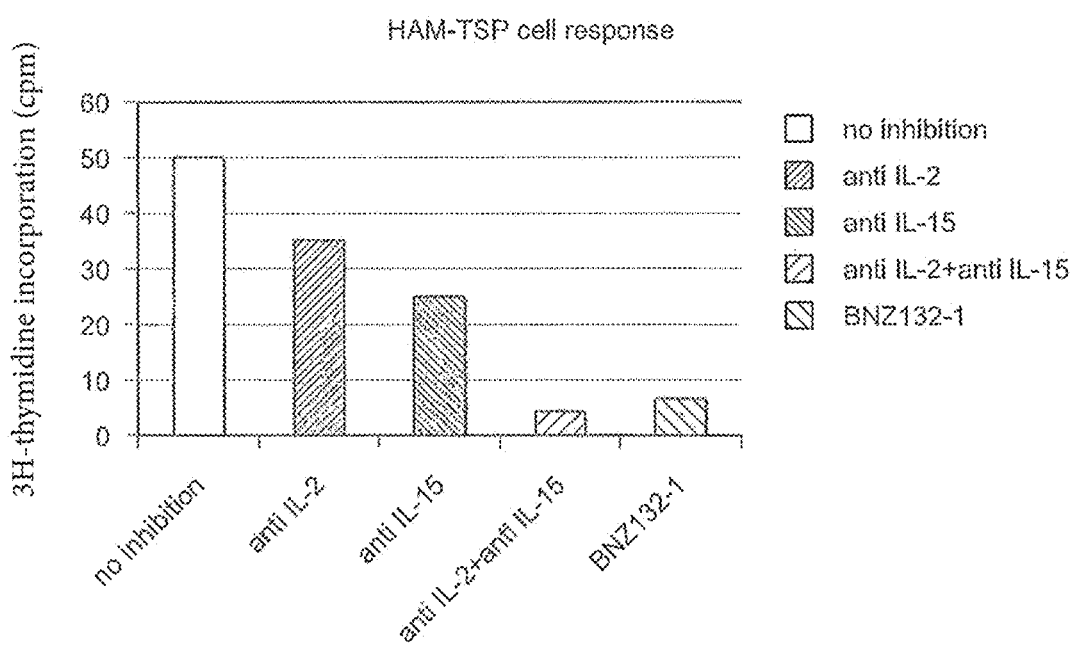

In the experiment illustrated in FIGS. 11A and 11B, in an attempt to generate IL-21 responding PT-18 cells, the cDNAs encoding human and mouse IL-21Rα amplified by RT-PCR from primary cultured cells (human blood PBMC and mouse splenocytes) were cloned into the pEF-Neo expression vector. After 10 days of culture with selection drug G418 (0.5 mg/ml), the surviving cells were stained by the respective antibody (human; Biolegend, Clone 17A2, mouse; eBioscience, clone eBio4A9), sorted into 96-well plate by a single-cell. The resultant clones were subsequently reanalyzed for the expression of the IL-21Rα and used for biological assay.

Inhibitory Effect of BNZ132-1 on Another γc-Cytokine IL-9, but not on IL-4.

In addition, an experiment was conducted to test if BNZ132-1 inhibits other γc-cytokines using murine PT-18 cells that show versatile response to various cytokines. FIG. 10B shows that, BNZ132-1 did not inhibit IL-4 in PT-18 (p=0.32). IL-9 was partially inhibited (p=0.001) albeit not as robustly as IL-2 or IL-15. This partial inhibition appears to be consistent with a recent demonstration that IL-9Rα and IL-2/IL-15Rβ are more closely related than other pairs of private chains from this family.

BNZ132-1 Did not Substantially Inhibit IL-7 or IL-21.

Next, an experiment was conducted to test if the two remaining γc-cytokines, namely IL-7 and -21, were inhibited by BNZ132-1. A PT-18 subclone that responds to human IL-21 by transfecting human IL-21Rα was established and used in this experiment (FIG. 15). Though hIL-21Rα+PT-18 cells did not robustly proliferate to IL-21 (FIG. 10B), IL21 prevented their apoptotic death following the withdrawal of IL-3 from the culture (FIG. 10C, *; p=0.001), which was not inhibited by BNZ132-1 (**; p=0.59). Then similar experiments with IL-7 were conducted. In this experiment, ex vivo human primary T cells were used to determine if BNZ132-1 inhibits IL-7. As shown in FIG. 10D, human T cells demonstrated moderate response to 10 nM IL-7 (vs. No cytokine; p=0.002) which was not significantly inhibited by BNZ132-1 (p=0.30). Collectively, the inhibitory capacity of BNZ132-1 seems restricted to IL-2, -15, and -9, but excludes IL-4, -7 or -21.

Inhibition by BNZ132-1 Appears Limited to γc-Cytokines.

An experiment was conducted to test if BNZ132-1 inhibits non-γc cytokine. Again PT-18 which natively responds to an array of non-γc cytokines including mouse stem cell factor (SCF), mouse IL-3, mouse GM-CSF, and human FLT3-ligand was used (FIG. 16). As shown in FIG. 10E, BNZ132-1, even at an excess dose at 15 μM, showed no inhibition on these cytokines.

Biochemical Aspects of the Cytokine Inhibitory Function of BNZ132-1.

Next, the biochemical aspects of the BNZ132-1 inhibition of target cytokines were investigated. As the Cheng-Prusoff equation dictates, IC50 is closely associated with the binding affinity of the antagonist to the cellular receptor.

FIG. 11A shows that BNZ132-1 efficiently blocked the combinatorial effect of IL-2 and IL-15. PBMCs from a healthy donor were stimulated with PHA (0.5 mg/ml) for 48 hr, followed by IL-2 expansion (0.5 nM) for 48 hrs. After 12 hr of resting (no cytokine culture), cells were depleted of non-T cells by a MACS negative sorting, and IL-2 and IL-15 (combined at 1 nM, 0.1 nM, and 10 μM, respectively) were added to the culture. BNZ132-1 at 300 nM significantly inhibited the combined effects of IL-2 and IL-15 on ex vivo human T cells. The effect of BNZ132-1 was comparable to the effect of combined anti-IL-2 and anti-IL-15 mABs. Of note is the only partial inhibition of the proliferation by anti-IL-2 or anti-IL-15 antibody alone.

FIG. 11B illustrates effective inhibition of the ex vivo proliferation of HAM/TSP T cells by BNZ132-1. Peripheral lymphocytes from a HAM/TSP patient spontaneously proliferated in an ex vivo culture for 5 days in the absence of exogenously added cytokines. It has been reported previously (Tendler C L et al, Cytokine induction in HTLV-associated myelopathy and adult T-cell leukemia: alternate molecular mechanism underlying retroviral pathogenesis 1991 J Cell Biochem, Azimi N. et al, Involvement of IL-15 in the pathogenesis of HTLV in HAM/TSP, J. Immunol. 1999), which are incorporated by reference herewith) that this is, in part, is due to endogenous production of IL-2 and IL-15. Addition of anti-IL-2 or anti-IL-15 mAB (5 mg/ml each) only partially inhibited the spontaneous proliferation in this culture. A cocktail of anti-IL-2 and anti-IL-15 mABs (5 mg/ml each) inhibited the proliferation almost completely. Similarly, addition of BNZ132-1 (1 uM) to the ex vivo culture showed as effective inhibition as combined anti-IL-2 and anti-IL-15 mABs.

During the course of experimentation, it was observed that BNZ132-1 inhibits IL-2, -15 and -9 at 50-150 nM in a human NK92 cell line and with ex vivo human T cells, which gives approximately 10-60 nM of binding affinity of BNZ132-1 to target cells. Some of the data are provided in, e.g. FIGS. 12A-12C.

FIG. 12A shows estimation of $IC_{50}$ concentration of BNZ132-1 to IL-2/IL-15-induced proliferation of ex vivo human T-lymphocytes. Mixed cytokine assay was established as described before (FIG. 7). A serial dilution of BNZ132-1 was added to the culture to inhibit the combined (IL-2+IL-15, 0.1 nM each)) effects on the cells. The $IC_{50}$ value (150 nM) was deduced form this assay.

FIGS. 12B and 12C show the results of NK92 cell proliferation assay. NK92 cells responded to IL-2 and IL-15. BNZ132-1 inhibited the IL-2 (FIG. 12B) and IL-15 (FIG. 12C). Induced proliferation in a dose-dependent manner on NK92 cells. Similar results with other cell lines from non-human species (data not shown) were observed.

Efficient Inhibition by BNZ132-1 of the Combined Cytokines Sharing Redundant Functions.

As shown in the above, BNZ132-1 inhibits not only one or all γc-cytokine, but three of them (IL-2, 9 and -15). An additional experiment was conducted to test if BNZ132-1 can effectively block the combined effect of two γc-cytokines (i.e., IL-2 and IL-15). It is noteworthy that even a 50:50 mixture of IL-2 and IL-15 cannot be inhibited by 50% by either anti-IL-2 or anti-IL-15 antibody if each cytokine was added near or over the saturating dose (0.1 or 1 µM each, FIG. 11A left), suggesting that a single antibody treatment may demonstrate only marginal inhibition in an in vivo situation in which more than two functionally redundant cytokines are cooperating. BNZ132-1 (300 nM) per se significantly ($p<0.05$) blocked the T-cell proliferation as efficiently as the combined antibodies at all doses of 10 uM each.

BNZ132-1 Specifically Inhibits Signaling Events Downstream of Target γc-Cytokines Cellular proliferation often represents a combination of several independent signaling pathways, and inhibiting one signaling branch could stop the proliferation. Thus, it may need to verify that multiple signaling branches triggered by a target cytokine have been comprehensively inhibited by BNZ132-1. FIGS. 13A-13C show comprehensive inhibition of the signal transduction pathways downstream of IL-15/IL-15 receptor system in PT-18 cells by BNZ 132-1. PT-18☐ cells have been withdrawn of IL-15 for overnight to induce into proliferative quiescence (no-stimulation). To restimulate the cells, 1 nM of IL-15 was added in the presence or absence of BNZ132-1 (0.5 mM). After 30 min, cell lysates were collected and phosphorylation of key mediators of major signaling branches were determined by western blotting.

As noted, FIGS. 13A-13C show the inhibition by BNZ132-1 of the tyrosine-phosphorylation of key molecules representing major branches of the γc-cytokine signaling, namely the STAT5, PI3 kinase-Akt, and MAP-kinase branches, suggesting BNZ132-1 comprehensively inhibited human IL-15 (A; in PT-18β), mouse IL-9 (B; in PT-18) and human IL-2 (C; in human Peripheral T cells). Lane 4 of FIG. 13C (low dose BNZ132-1) shows that suboptimal dose of BNZ132-1 may cause differential inhibitions on individual pathways, in that Akt and p38 are more sensitive than Jak3 and STAT5. The signal transduction was relatively linear from the γc/Jak3 complex to STAT5, but was somewhat dampened in the other two branches. Cellular proliferation paralleled the pattern of Jak3 and STAT5 shown in FIGS. 10A-10E. The IL-4 experiment demonstrates that BNZ132-1 does not interfere with signaling events of a non-target cytokine, strongly suggesting that the action of this peptide only occurs extracellularly.

Designing Peptides that Target Other Cytokines within the γc Family

Using similar strategy, we have designed a library of antagonist peptides that inhibit different subset of the γc family of cytokines. For example, an antagonist peptide A will inhibit IL-15, IL-21 and IL-9 but not IL-2, IL-4, and IL-7. Or antagonist peptide B will inhibit IL-4 and IL-21 but not IL-2, IL-9, IL-7, or IL-15. A mathematical expansion of BNZ-peptides into a comprehensive library is shown in Table 4.

TABLE 4

A mathematical expansion of BNZ-peptides into a comprehensive library

| ID | Number of the γc-member cytokines | IL-2 | IL-4 | IL-7 | IL-9 | IL-15 | IL-21 | Existing targeting compounds | Target Diseases |
|---|---|---|---|---|---|---|---|---|---|
| 1 | 6 | X | X | X | X | X | X | Tofacitinib (CP590, 660), | |
| 2 | 5 | | X | X | X | X | X | | |
| 3 | 5 | X | | X | X | X | X | | |
| 4 | 5 | X | X | | X | X | X | | |
| 5 | 5 | X | X | X | | X | X | | |
| 6 | 5 | X | X | X | X | | X | | |
| 7 | 5 | X | X | X | X | X | | | |
| 8 | 4 | | | X | X | X | X | | |
| 9 | 4 | | X | | X | X | X | | |
| 10 | 4 | | X | X | | X | X | | |
| 11 | 4 | | X | X | X | | X | | |
| 12 | 4 | | X | X | X | X | | | |
| 13 | 4 | X | | | X | X | X | | MS? |
| 14 | 4 | X | | X | | X | X | | |
| 15 | 4 | X | | X | X | | X | | |
| 16 | 4 | X | | X | X | X | | | |
| 17 | 4 | X | X | | | X | X | | |
| 18 | 4 | X | X | | X | | X | | |
| 19 | 4 | X | X | | X | X | | | |
| 20 | 4 | X | X | X | | | X | | |
| 21 | 4 | X | X | X | | X | | | |
| 22 | 4 | X | X | X | X | | | | |
| 23 | 3 | | | | X | X | X | | |
| 24 | 3 | | | X | | X | X | | RA? |
| 25 | 3 | | | X | X | | X | | |
| 26 | 3 | | | X | X | X | | | |
| 27 | 3 | | X | | | X | X | | |
| 28 | 3 | | X | | X | | X | | |
| 29 | 3 | | X | | X | X | | | |
| 30 | 3 | | X | X | | | X | | |
| 31 | 3 | | X | X | | X | | | |
| 32 | 3 | | X | X | X | | | | |
| 33 | 3 | X | | | | X | X | | |
| 34 | 3 | X | | | X | | X | | |
| 35 | 3 | X | | | X | X | | | |
| 36 | 3 | X | | | | X | X | | |
| 37 | 3 | X | | | X | | X | | |
| 38 | 3 | X | | | X | X | | BMZ132-2 | HAM-TSP |

TABLE 4-continued

A mathematical expansion of BNZ-peptides into a comprehensive library

| ID | Number of the γc-member cytokines | IL-2 | IL-4 | IL-7 | IL-9 | IL-15 | IL-21 | Existing targeting compounds | Target Diseases |
|---|---|---|---|---|---|---|---|---|---|
| 39 | 3 | X | X |   | X |   |   |   |   |
| 40 | 3 | X | X |   |   | X |   |   |   |
| 41 | 3 | X | X |   |   |   | X |   |   |
| 42 | 3 | X | X | X |   |   |   |   |   |
| 43 | 2 | X | X |   |   |   |   |   |   |
| 44 | 2 | X |   | X |   |   |   |   |   |
| 45 | 2 | X |   |   | X |   |   |   |   |
| 46 | 2 | X |   |   |   | X |   | Anti-IL-2/IL-15Rβ Ab (TMβ1) |   |
| 47 | 2 | X |   |   |   |   | X |   | Uveites? |
| 48 | 2 |   | X | X |   |   |   |   |   |
| 49 | 2 |   | X |   | X |   |   | BMZ132-2 | Asthma |
| 50 | 2 |   | X |   |   | X |   |   |   |
| 51 | 2 |   | X |   |   |   | X |   |   |
| 52 | 2 |   |   | X | X |   |   |   |   |
| 53 | 2 |   |   | X |   | X |   |   |   |
| 54 | 2 |   |   | X |   |   | X |   |   |
| 55 | 2 |   |   |   | X | X |   |   |   |
| 56 | 2 |   |   |   | X |   | X |   |   |
| 57 | 2 |   |   |   |   | X | X | BMZ132-2 | Celiac Disease |
| 58 | 1 | X |   |   |   |   |   | anti-IL2 Ab, anti-CD25 Ab |   |
| 59 | 1 |   | X |   |   |   |   | anti-IL-4 Ab, modified IL-4, anti-IL-4Ra antiobody |   |
| 60 | 1 |   |   | X |   |   |   | anti-IL-7, anti-IL-7Ra antibody |   |
| 61 | 1 |   |   |   | X |   |   | anti-IL-9 |   |
| 62 | 1 |   |   |   |   | X |   | anti-IL-15, anti-IL-15Ra antibody, soluble IL-15Ra | LGL |
| 63 | 1 |   |   |   |   |   | X | anti-IL-21, anti-IL-21Ra antibody |   |

Establishment of Cytokine-Responsive PT-18 Subclones

In FIG. 17A, with an attempt to generate IL-7-responding PT-18 subclones, human IL-7Ra cDNA was subcloned into the pEF-Neo expression vector and transfected into PT-18 cells by electroporation. After selection with G418, the survived cells were stained by anti-IL-7Ra (anti-CD127) antibody (Biolegend, clone A019D5), and sorted by a single cell into 96-well culture plate. The expanded clones were again stained by the same antibody. To generate another subclones that expresses human gc (CD132) in addition to the human IL-7Ra, the human IL-7Ra+PT-18 clone was additionally transfected with human gc-cDNA in the pEF-Neo vector and the cells were sorted multiple times after staining with anti-human IL-7Ra (Biolegend, clone TUGH4). The upper right histogram demonstrates the expression levels of endogenous mouse CD132 (γc) on the parental PT-18 cell line (red line; isotype control, blue line; PE-anti mouse CD132, BD Biosciences, clone TUGm2). The PT-18 with human IL-7Ra/human gc was established after the completion of the body of the study. Although their response to human IL-7 has been confirmed. Similar methods can be used to establish PT-18 subclones that are responsive to other cytokines.

The term "comprising" as used herein is synonymous with "including," "containing," or "characterized by," and is inclusive or open-ended and does not exclude additional, unrecited elements or method steps.

Not as an attempt to limit the application of the doctrine of equivalents to the scope of any claims in any application claiming priority to the present application, each numerical parameter should be construed in light of the number of significant digits and ordinary rounding approaches.

The term "about" as used herein with respect to a numerical quantity should be interpreted as meaning plus or minus 10% of that quantity.

Amino acids and amino acid residues are referred to using their one-letter or three letter code abbreviations, and are written with an implied N-terminal amino on their left and C-terminal carboxy group on their right unless otherwise indicated or implied by the accompanying text or otherwise herein.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

As another example illustrative of both specific details and general aspects of the compositions and methods disclosed herein, one may review an inhibitor polypeptide generated to target specific members of the IL-6 cytokine family.

The IL-6 family includes seven cytokines (IL-6, IL-11, ciliary neurotrophic factor (CNTF), leukemia inhibitory factor (LIF), oncostatin M (OSM), cardiotrophin-1 (CT-1), OSM, cardiotrophin like cytokine (CLC), and IL-27. These cytokines share the gp130 receptor which is the signaling component of their receptor complexes. All cytokine in this family signal through complexes comprising the gp130 receptor subunit, but each have a specific receptor component as well. A common downstream component of IL-6 family signaling is the STAT3 transcription factor.

Similar to the gamma c cytokines, each cytokine in the IL-6 family has a specific receptor that forms a unique high affinity receptor complex in combination with gp130. Upon binding of the cytokine to its receptor complex, a cascade of computer modeling in other family members. Then one may analyze the amino acid sequence of each cytokine based on the anticipated binding sites between the D-helix region and the gp130 receptor. The spatial alignment of the helices structures reveals key amino acids that are involved in each cytokines binding to its common receptor. In some embodiments those amino acids are likely to be involved in receptor-binding interaction.

D-helix sequences of IL-6 family members and of inhibitory polypeptide BNZ130-1 are shown in Table 5.

TABLE 5

Alignment of the D-helix amino acid sequence of IL-6 family

| Residue | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| IL-6 (SEQ ID NO: 122) | M | T | T | H | L | I | L | R | S | F | K | E | F | L | Q | S | S | I | R | A | I | R | Q | M |
| IL-27 (SEQ ID NO: 123) |  | L | L | H | S | L | E | V | L | S | R | A | V | R | E | L | L | L | L | L | S | K | A |  |
| BNZ130-1 (SEQ ID NO: 124) |  | L | T | H | L | I | E | R | S | S | R | A | V | L | Q | S | L | L |  | R | A | S | R | Q |
| IL-11 (SEQ ID NO: 125) | A | G | G | L | H | L | T | L | D | W | A | V | R | G | - | L | L | L | L | K | T | R | L |  |
| CNTF (SEQ ID NO: 126) | V | L | Q | E | L | S | Q | W | T | V | R | S | I | H | D | L | R | F | I | S | S | H | Q |  |
| CT-1 (SEQ ID NO: 127) |  | V | F | P | A | K | V | L | G | L | R | V | C | G | L | Y | R | E | W | L | S | R | T |  |
| OSM (SEQ ID NO: 128) |  | A | L | R | K | G | V | R | R | T | R | P | S | R | K | G | K | R | L | M | T | R | G |  |
| LIF (SEQ ID NO: 129) |  | F | Q | K | K | L | G | C | Q | L | L | G | K | Y | K | Q | I | I | A | V | L | A | Q |  | intracellular events will take place that initiates intracellular signaling via the JAK/STAT pathway. In addition to the activation of the canonical JAK/STAT pathway, the phosphatase SHP-2 is recruited to tyrosine phosphorylated gp130, becomes phosphorylated by JAK1 and thereupon mediates the activation of the Ras-Raf-MAPK signaling pathway. IL-6 signaling has been implicated in the inflammatory response, in particular in rheumatoid arthritis.

In the IL-6 family, there is no apparent amino acid sequence homology evident in an alignment, meaning that alignment of amino acid sequences of this family does not immediately identify regions from which one may draw sequence fragments to assemble an inhibitory polypeptide. However, modeling after the well-studied 3D structure of IL-6, one can predict the relevant domains in other family members. Modeling may be performed using a number of computational techniques known to one of skill in the art, such as secondary structure prediction software or threading software available to one of skill in the art and capable of predicting secondary and higher order structure either de novo or in comparison to a protein of known structure, such as IL-6. Again, one may rely on scientific literature and structure databases to obtain sequence, secondary structure and higher order structure information as necessary to support this analysis.

It has been demonstrated that both the B-helix and the D-helix contain receptor binding domains in IL-6. One may identify the predicted B-helix and D-helix structure using The polypeptide BNZ130-1 is designed through methods disclosed herein so that IL-6 and IL-27 are selectively inhibited while IL-11, CNTF, CT-1, OSM and LIF are not. The polypeptide BNZ130-1 comprises six individual sequence fragments corresponding to residues 2, 4, 7, 10-13, 17-18 and 21 of IL-27. The polypeptide BNZ130-1 also comprises five sequence fragments corresponding to residues 3-6, 8-9, 14-16, 19-20, and 22-23 of IL-6. Consistent with the greater degree of sequence divergence among the IL-6 family members as discussed above, only one sequence fragment, the single-residue fragment of IL-27 at residue 4, does not map uniquely to a single target region.

Referring to BNZ130-1, one may again observe both specific details and general characteristics of the method disclosed herein. Target polypeptides are represented in approximately equal amounts, (13 residues of IL-6 as compared to 10 residues of IL-27). Sequence fragments are of four or fewer residues, and are approximately evenly distributed between the target regions of IL-6 and IL-27. No more than two consecutive residues match a non-target IL-6 family member, and no off-target family member matches BNZ130-1 at more than four residues, no more than two of which are consecutive.

As another example illustrative of both specific details and general aspects of the compositions and methods disclosed herein, one may review an inhibitor polypeptide generated through the methods disclosed herein to target specific members of the IL-17 cytokine family.

Through the detailed examination of the general attributes of the above disclosure, one may understand parameters and guidelines for the implementation of the methods and compositions disclosed herein.

Also contemplated herein are inhibitory polypeptides that specifically target ligand-receptor signaling across families, for example specifically targeting one, two, three, four, five, six, or more than six members of a first family and also specifically targeting one, two, three, four, five, six, or more than six members of a second family.

Cross-family inhibitory polypeptides may be designed by, for example, joining two or more single-family inhibitory polypeptides as disclosed herein with a linker molecule such that the two or more single-family inhibitory polypeptides are tethered to one another.

A cross-family inhibitory polypeptide may comprise more than one single family inhibitory polypeptide. Single family polypeptide inhibitors as constituents of a cross-family inhibitory polypeptide may be designed as disclosed above. Additionally, a single-family inhibitor polypeptide may be synthesized to target a single ligand-receptor signaling complex rather than multiple members of a family, such that each 'fragment sequence' of the inhibitor polypeptide is drawn from a target region of a single protein, or such that an inhibitory polypeptide comprises part or all of a single target region, such that if not incorporated into a cross-family inhibitory polypeptide, the inhibitory polypeptide specifically inhibits a single ligand-receptor signaling complex or a single ligand or a single receptor.

Single family polypeptide inhibitors as constituents of a single cross-family inhibitory polypeptide may be joined to one another by a linking molecule, such as a linking molecule covalently bound to at least two single family polypeptide inhibitors. Examples of linking molecules include lipids, such as a poly (—$CH_2$—) hydrocarbon chains, unsaturated variants thereof, hydroxylated variants thereof, amidated or otherwise N-containing variants thereof, non-carbon linkers; carbohydrate linkers; phosphodiester linkers, or other molecule capable of covalently binding to two or more polypeptides.

Non-covalent linkers are also contemplated, such as hydrophobic lipid globules to which at least one single family polypeptide inhibitor may be tethered, for example through a hydrophobic region of the inhibitor polypeptide or a hydrophobic extension of the polypeptide, such as a series of residues rich in Leucine, Isoleucine, Valine, or perhaps also Alanine, Phenylalanine, or even Tyrosine, Methionine, Glycine or other hydrophobic residue. Inhibitor polypeptides may also be tethered using charge-based chemistry, for example such that positively charged moiety of a single family polypeptide inhibitor is bound to a negative change of a linker moiety.

Single family polypeptide inhibitors as constituents of a single cross-family inhibitory polypeptide may be joined to one another by a continuous polypeptide tether such that in some embodiments the single cross-family inhibitory polypeptide comprises a single continuous polypeptide, such as a polypeptide having a first region which corresponds to a first single family polypeptide inhibitor, having a second region which corresponds to a second single family polypeptide inhibitor, and optionally having a third region corresponding to a linker polypeptide sequence. In some embodiments the first region which corresponds to a first single family polypeptide inhibitor and the second region which corresponds to a second single family polypeptide inhibitor are directly linked without intervening polypeptide sequence.

Much like single family polypeptide inhibitors, cross-family inhibitory polypeptides may be synthesized using techniques known to one of skill in the art. Single polypeptide molecules may, for example, be encoded by a single polynucleic acid molecule and translated, for example translated on a ribosome, to produce the desired polypeptide molecule. Non-translation based polypeptide synthesis is also contemplated. Cross-family inhibitory polypeptides comprising non-polypeptide components may be synthesized using standard biochemical techniques familiar to one of skill in the art or may be synthesized by a chemical synthesis service provider.

As an example illustrative of both specific details and general aspects of the compositions and methods disclosed herein, one may review a cross-family inhibitory polypeptide generated to target both specific members of the gamma-c cytokine family and specific members of the IL-6 cytokine family. In particular, one may review a specific inhibitor of gamma-c cytokines IL-2, IL-15 and IL-9, and IL-6 family cytokines IL-6 and IL-27.

As an example of a cross-family inhibitory polypeptide, we linked the peptide BNZ132-1 demonstrated in Table 1 to BNZ130-1 demonstrated in Table 2 via a bi-functional PEG24 molecule (Mal-PEG24).

The molecule is IKEFLQSFIHIVQSIINT (SEQ ID NO: 130)—MAL-PEG24—SLTHLIERSSRAVLQSLLRASRQ (SEQ ID NO: 131). The dual peptide antagonist was called BNZ132-PEG-130

FIGS. 14A-14C demonstrate the effect of BNZ132-PEG-130 in inhibiting the IL-2 and IL-15 induced proliferation of CTLL2 cells as well as the IL-6 induced proliferation of T1156 cells. BNZ132-1 was conjugated to BNZ130 via a PEG24 linker. The name of the bi-antagonist peptide is BNZ132-PEG-130. FIGS. 10A and 10B show the results BNZ132-PEG-130 in IL-2 (A) and IL-15 (B) CTLL2 proliferation assay. Cells were washed and incubated with IL-2 (5 and 10 units/ml), IL-15 (2.5 and 5 ng/ml) in the presence or absence of BNZ132-PEG-130 (0.1-10 uM). Cells were then pulsed with the WST-1 reagent to measure the proliferative response for the next 6 hr ($OD_{450}$). FIG. 14C shows the effect of BNZ1321-PEG-130 in IL-6 proliferation in T1165 cells. Cells are washed and incubated with IL-6 (0.1 ng/ml) of IL-6 presence or absence of BNZ132-PEG-130 (0.1-10 mM) for 24 hours. Cells were pulsed with WST-1 reagent for the following 6 hr to measure $OD_{450}$.

As demonstrated above and disclosed generally, two single family polypeptide inhibitors may be covalently tethered by an intervening linker sequence to form a cross family polypeptide inhibitor having the specificity of each of its single family polypeptide inhibitors.

As demonstrated above and disclosed generally, a target region of a single specific target molecule may be covalently tethered by an intervening linker sequence to a single-family inhibitory polypeptide to form a cross family polypeptide inhibitor having the specificity of the single-family inhibitory polypeptide and also inhibiting the polypeptide corresponding to the included target region.

In certain embodiments, inhibitory peptides disclosed herein can be modified, e.g. via PEGylation. Accordingly, in some embodiments, BNZ132-1 can be conjugated to a linear PEG molecule with MW of 40 KD at the N-terminus via a linker of (Gly-Ser-Gly-Gly, SEQ ID NO: 132). The final molecule can be H-Cys(acetylamino-propyl-mPEG40k)-Gly-Ser-Gly-Gly-Ile-Lys-Glu-Phe-Lue-Gln-Arg-Phe-Ile-His-Ile-Val-Gln-Ser-Ile-Ile-Asn-Thr-Ser-NH2 (SEQ ID NO: 133).

The present invention has been described in some detail for purposes of clarity and understanding, one skilled in the art will appreciate that various changes in form and detail can be made without departing from the true scope of the invention.

ADDITIONAL EXAMPLES

Example 15 Identification of Ligand Targets

A cytokine or signaling pathway is implicated in a disease in the scientific literature. A set of ligands in a structurally determined ligand family each of which is independently implicated in the signaling pathway is identified based on publicly available information in the scientific literature. Other ligands in the same structural ligand family but not implicated in the common signaling pathway are also identified based on publicly available information in the scientific literature. The ligands implicated in the signaling pathway are selected for specific inhibition.

This example shows that specific ligands within a structural family of ligands may be selected for specific inhibition based on publicly available information in the literature.

Example 16 Identification of a Target Region—Modest Sequence Similarity

Polypeptide sequence for each member of the family of ligands of Example 15 is obtained from the national center for biotechnology information (ncbi). The family is researched in the publicly available literature and information on the structure of a member of the family is obtained, including information related to a ligand's interaction with a receptor.

Sequences for the polypeptides are aligned using COBALT, a protein alignment algorithm publicly available at ncbi. Other software publicly available (such as software by Stanford University) is also suitable. The family members demonstrate an overall pairwise sequence identity of 20% and a pairwise sequence similarity of 50%, and about the same length, indicating that the sequence alignment is likely indicative homologous regions of each family member. The region of each family member corresponding to the region which interacts with the receptor in one known family member is identified as a Target Region.

This example shows how a target region is identified among ligands in a ligand family based on sequence information, alignment tools and the scientific literature.

Example 17 Identification of a Target Region—Low Sequence Similarity

Polypeptide sequence for each member of a family of ligands identified as in Example 15 is obtained from the national center for biotechnology information (ncbi). The family is researched in the publicly available literature and information on the structure of a member of the family is obtained, including information related to a ligand's interaction with a receptor.

Sequences for the polypeptides are aligned using COBALT, a protein alignment algorithm publicly available at NCBI. The family members demonstrate an overall pairwise sequence identity of near 0% and a pairwise sequence similarity of near 0%, and substantial length variation, indicating that the sequence alignment is likely not indicative homologous regions of each family member. Family members are subjected to 3D structure prediction such as that described in Wang et al., (2013) Bioinformatics. 2013 Jul. 1; 29(13):i257-65, which is incorporated by reference herein. The region of each family member corresponding to the region which interacts with the receptor in one known family member is identified as a Target Region.

This example shows how a target region is identified among ligands in a ligand family based on sequence information, alignment tools and the scientific literature.

Example 18 Identification of Sequence Fragments for Inhibitory Polypeptide

The Target Region of Example 16 is identified for each ligand to be inhibited. Sequence fragments that map to the ligands to be inhibited but not to the other ligands in the family are selected. Sequence fragments that uniquely map to a single ligand to be inhibited are selected. Sequence fragments that span 1-2 residues universally conserved in the family are not excluded provided that they satisfy the above criteria.

This example demonstrates how sequence fragments are identified among sequences of relatively high sequence identity.

Example 19 Identification of Sequence Fragments for Inhibitory Polypeptide

The Target Region of Example 17 is identified for each ligand to be inhibited. Sequence fragments that map to the ligands to be inhibited but not to the other ligands in the family are selected. Sequence fragments that uniquely map to a single ligand to be inhibited are selected. Sequence fragments that comprise more than 1 residue of a ligand that is not to be inhibited are not included.

This example demonstrates how sequence fragments are identified among sequences of relatively low sequence identity.

Example 20 Inhibitory Polypeptide Assembly

The sequence fragments of Example 18 are assembled into a single inhibitory polypeptide sequence based on an algorithm described in section above (design of BNZ132-1) to block the interface of the specific cytokines to the receptor, to form a the three dimensional structure that is modeled after the original cytokines, and to have equal potencies for both cytokines. This example demonstrates how sequence fragments are assembled into an inhibitory polypeptide.

Example 21 Inhibitory Polypeptide Activity Confirmation

A cell line is identified requiring constitutive activity of the signaling pathway of Example 15 for its cell proliferation. The cell line is cultured in the absence of all reagents necessary for growth, and in the presence of each ligand which is implicated in the signaling pathway to be targeted. Cells are incubated with individual ligands and with pairwise combinations of ligands, triplet combinations of ligands and higher order combinations of ligands up to the point that all ligands implicated in the signaling pathway to be targeted are included. Different cell lines are used to test the inhibitory effect of the peptide against different ligand.

Each combination of ligands and cells is cultured in the presence and in the absence of the inhibitory polypeptide at a range of physiological concentrations within an order of magnitude of the molar concentration of the total number of ligands to be inhibited or the total number of receptors whose interactions with the ligands is to be blocked.

It is observed that in the absence of the inhibitory polypeptide, the cell line proliferates in the presence of one or more of the ligands but does not proliferate in the absence of any of the ligands. It is observed that in the absence of all ligands the cell line fails to proliferate but does not die.

It is observed that in the presence of the inhibitory polypeptide the cell line does not proliferate, independent of the presence of one or more of the ligands. It is also observed that the cell line does not immediately die despite failing to proliferate. The effect of the inhibitory peptide is dose-dependent.

This example demonstrates that the inhibitory polypeptide blocks the signaling which is redundantly effected by any of the ligands to which it is directed. This example also demonstrates that the inhibitory polypeptide does not have any 'off-target' effects that may lead to lethality.

Example 22 Inhibitory Polypeptide Specificity Confirmation

A cell line is identified requiring constitutive activity of a signaling pathway in which a non-targeted ligand of the family of Example 15 for its cell proliferation. The cell line is cultured in the absence of all ligands necessary for growth, and in the presence of each non-targeted ligand of the family of Example 15.

Each combination of ligands and cells is cultured in the presence and in the absence of the inhibitory polypeptide at a range of physiological concentrations within an order of magnitude of the molar concentration of the total number of ligands to be inhibited or the total number of receptors whose interactions with the ligands is to be blocked, and at higher inhibitory polypeptide concentrations.

It is observed that in the absence of the inhibitory polypeptide, the cell line proliferates in the presence of one or more of the ligands but does not proliferate in the absence of any of the ligands. It is observed that in the absence of all ligands the cell line fails to proliferate but does not die.

It is observed that in the presence of the inhibitory polypeptide the cell line proliferates in the presence of one or more of the ligands but does not proliferate in the absence of any of the ligands. It is observed that in the absence of all ligands the cell line fails to proliferate but does not die.

This example demonstrates that the inhibitory polypeptide has no effect on the signaling activity of non-targeted ligands in the family of the targeted ligands.

Example 23 Cross-Family Inhibitory Polypeptide Activity Confirmation

The inhibitory polypeptide of Examples 21 and 22 is covalently linked to a second inhibitory polypeptide targeting a second ligand family's members implicated in a second pathway. A cell line requiring constitutive activity of the second pathway for proliferation, but that signaling related to the first signaling pathway is not necessary for proliferation, is obtained. Experiments analogous to those of Examples 21 are performed on the second cell line.

The cell line is cultured in the absence of all ligands necessary for growth, and in the presence of each ligand which is implicated in the second signaling pathway to be targeted. Cells are incubated with individual ligands and with pairwise combinations of ligands, triplet combinations of ligands and higher order combinations of ligands up to the point that all ligands implicated in the second signaling pathway to be targeted are included.

Each combination of ligands and cells is cultured in the presence and in the absence of the second inhibitory polypeptide covalently linked to the inhibitory polypeptide of Examples 21 and 22 at a range of physiological concentrations within an order of magnitude of the molar concentration of the total number of ligands to be inhibited or the total number of receptors whose interactions with the ligands is to be blocked.

It is observed that in the absence of the second inhibitory polypeptide covalently linked to the inhibitory polypeptide of Examples 21 and 22, the cell line proliferates in the presence of one or more of the ligands but does not proliferate in the absence of any of the ligands. It is observed that in the absence of all ligands the cell line fails to proliferate but does not die.

It is observed that in the presence of the second inhibitory polypeptide covalently linked to the inhibitory polypeptide of Examples 21 and 22 the cell line does not proliferate, independent of the presence of one or more of the ligands. It is also observed that the cell line does not die despite failing to proliferate.

This example demonstrates that the second inhibitory polypeptide covalently linked to the inhibitory polypeptide of Examples 21 and 22 blocks the second signaling pathway which is redundantly effected by any of the ligands to which it is directed. This example also demonstrates that the second inhibitory polypeptide does not have any 'off-target' effects that may lead to lethality.

Example 24 Cross-Family Inhibitory Polypeptide Specificity Confirmation

A cell line is identified having a defect such that constitutive activity of a signaling pathway in which non-targeted ligand of the family of Example 23 is required for its cell proliferation, and in which the signaling pathway of Example 15 is also not required for its proliferation. The cell line is cultured in the absence of all ligands necessary for growth, and in the presence of each non-targeted ligand of the family of Example 23.

Each combination of ligands and cells is cultured in the presence and in the absence of the second inhibitory polypeptide covalently linked to the inhibitory polypeptide of Examples 21 and 22 at a range of physiological concentrations within an order of magnitude of the molar concentration of the total number of ligands to be inhibited or the total number of receptors whose interactions with the ligands is to be blocked, and at higher inhibitory polypeptide concentrations.

It is observed that in the absence of the second inhibitory polypeptide covalently linked to the inhibitory polypeptide of Examples 21 and 22, the cell line proliferates in the presence of one or more of the ligands but does not proliferate in the absence of any of the ligands. It is observed that in the absence of all ligands the cell line fails to proliferate but does not die.

It is observed that in the presence of the second inhibitory polypeptide covalently linked to the inhibitory polypeptide of Examples 21 and 22 the cell line proliferates in the presence of one or more of the ligands but does not proliferate in the absence of any of the ligands. It is observed that in the absence of all ligands the cell line fails to proliferate but does not die.

This example demonstrates that the second inhibitory polypeptide covalently linked to the inhibitory polypeptide of Examples 21 and 22 has no effect on the signaling activity of non-targeted ligands in the family of the targeted ligands of Example 23.

Example 25 Peptide Activity Confirmation

The BNZ130-1 polypeptide as presented in Table 2, above, is tested for its activity in inhibiting IL-6 activity. T1165 cells that are dependent on human or mouse IL-6 for their growth in vitro are selected. The cell line is cultured in the absence of IL-6, In the presence of IL-6, in the presence of BNZ130-1, and in the presence of IL-6 and BNZ130-1.

A dose-dependent antagonistic activity of BNZ130-1 on T1165 proliferation in the presence of IL-6 is observed, indicative of IL-6 inhibition by BNZ130-1. BNZ130-1 does not affect T1165 survival as indicated by a similar cell survival rate of T1165 cells in the absence of IL-6 as compared to survival in the presence of BNZ130-1 independent of whether IL-6 is present.

Example 26 Peptide Optimization

A polynucleic acid encoding a 'parent' inhibitory polypeptide as identified above is subjected to an alanine screen whereby each codon is in turn mutated to a codon encoding alanine, namely GCG, GCC, GCT, or GCA. Each newly generated nucleic acid is used to direct synthesis of the encoded polypeptide, and the polypeptide is used in activity and specificity assays as described in the above-mentioned examples. Also, the peptide length is shortened to identify the minimum number of amino acids that can exhibit the best antagonistic activity. This is done by deletion mutagenesis from the N- and C-terminus of the peptide.

It is observed that a first child polypeptide performs better than the parent polypeptide in an assay of activity, such as by showing a similar level of inhibition as a lower concentration. It is observed that a second child polypeptide performs better than the parent polypeptide in an assay of specificity, such as by showing a reduced cell toxicity effect at any given concentration of administration.

A recombinant polypeptide is generated that comprises the mutations of the first child polypeptide and the second child polypeptide. The recombinant polypeptide performs like the first child polypeptide in activity assays and performs like the second child polypeptide in specificity assays. The recombinant polypeptide is selected for further development.

Example 27 Disease to Target—Celiac Disease (CD)

It has been shown in the literature that IL-15 and IL-21 are involved in the pathogenesis of refractory CD. An agonist peptide inhibitor is designed to simultaneously inhibit both cytokines IL-15 and IL-21. Since both of these cytokines share the common-gamma receptor, a single peptide is designed that inhibits both cytokines and does not inhibit the other gamma-c cytokines.

Common motifs that are likely to be involved in receptor cytokine binding are identified through sequence comparison. A peptide that is a composite of IL-15 and IL-21 at the common motifs is designed and synthesized. The polypeptide is tested in in vitro biological assays using cytokine-dependent cell lines. Performance is optimized using methods described above. The polypeptide is converted into a drug-like molecule using conjugation or cyclization of the peptide, and the drug-like molecule is tested for biological activity in cell culture and animal models.

Example 28 Disease to Target—Inflammatory Bowel Disease (IBD)

It has been shown in the literature that several cytokines from different families are involved in IBD. They include IL-17, IL-6 and IL-21.

An agonist peptide inhibitor is designed to simultaneously inhibit IL-17, IL-6 and IL-21. Since these cytokines belong to distinct cytokine families, separate antagonist peptides are designed described above to target each cytokine. Each antagonist peptide is optimized. Each antagonist peptide is linked to at least one of the other peptides via a linker (covalently bound amino acid linker or non-amino acid moiety such as PEG). The polypeptide is converted into a drug-like molecule using conjugation or cyclization of the peptide, and the drug-like molecule is tested for biological activity in cell culture and animal models. Alternately, the antagonist polypeptides are assembled in a nanosome structure or liposome for delivery.

Figure 7:
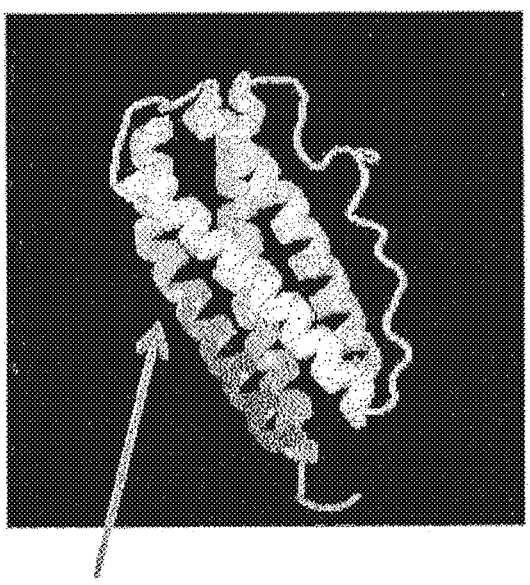
FIG. 7 depicts a D-helix within a structurally conserved cytokine-element. The figure presents the structure of a typical four-alpha helical cytokine.

A representative 'D-helix' alpha helical structure common to the cytokine family is depicted in FIG. 7. Four alpha-helices are involved in the structure. The 'D-helix' is indicated with an arrow. The D-helix is of central importance to ligand-receptor interactions, and is believed to contact the receptor.

The gamma c cytokine D-helix comprises 19 amino acids where out of the 19 positions, positions 4 and 5 are fully conserved as Phenylalanine, and Leucine, respectively across all members. Less conservation is observed at positions 6, 7 and 11 where the amino acid is one of two or three related amino acids that share physico-chemical properties: position 6 may be occupied by the polar amino acids Glutamate, Asparagine or Glutamine; non-polar amino acids Serine or Arginine can occupy position 7; and position 11 is occupied by either of the non-polar aliphatic amino acids Leucine or Isoleucine. Positions 9 and 16 may be occupied by the either the non-polar amino acid Isoleucine or the polar amino acid Lysine. Position 13 is either Glutamine or Arginine.

Some differences in the amino acid composition of the gamma c-box are observed at positions 9 and 6 amongst subfamilies of the gamma c-cytokines. Comparison of the gamma c-cytokines across species indicates that Isoleucine is frequently found at the 9 and 6 positions among members of the IL-2/15 subfamily, whereas the other gamma c-family members (e.g., IL-4, IL-21) possess Lysine in these positions. Not wishing to be bound by a particular theory, Isoleucine and Lysine are biochemically different and thus may impart specific conformational differences between the IL-2/15 subfamily and other gamma c-cytokines.

Conservation of the gamma motif between gamma c-cytokines is supported by findings that a residue located in the D-helix region is critical for the binding of the gamma c-cytokines to the gamma c-subunit. (Bernard et al., 2004 J. Biol. Chem. 279: 24313-21).

Sequences corresponding to the D-helix, a target region for the gamma-c cytokines, are given in Table 6.

TABLE 6

| Position | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|
| IL-2 (SEQ ID NO: 156) | I | V | E | F | L | N | R | W | I | T | F | C | Q | S | I | I | S | T | L | T | | |
| IL-15 (SEQ ID NO: 155) | I | K | E | F | L | Q | S | F | V | H | I | V | Q | M | F | I | N | T | S | | | |
| IL-9 (SEQ ID NO: 158) | A | L | T | F | L | E | S | L | L | E | L | F | Q | K | E | K | M | R | G | M | | R |
| BNZgamma (SEQ ID NO: 130) | I | K | E | F | L | Q | S | F | I | H | I | V | Q | S | I | I | N | T | S | | | |
| IL-4 (SEQ ID NO: 159) | L | E | N | F | L | E | R | L | K | T | I | M | R | E | K | Y | S | K | C | S | | S |
| IL-7 (SEQ ID NO: 160) | D | L | C | F | L | K | R | L | - | - | L | - | Q | E | I | K | T | C | W | K | I | L |
| IL-21 (SEQ ID NO: 161) | P | K | E | F | L | E | R | F | K | S | L | L | Q | K | M | I | H | Q | H | L | | S |

In this example, the polypeptide BNZ-gamma is designed so that the ligand-receptor activity related to IL-2, IL-15 and IL-9 is selectively inhibited while IL-4, IL-7 and IL-21 are not inhibited. The polypeptide BNZ-gamma comprises an individual sequence fragment comprising residues 1-8, which uniquely maps to homologous positions 1-8 of IL-15. The sequence fragment also comprises residues 3-5, which as an individual sequence fragment redundantly maps to residues 3-5 of IL-15 and IL-2, and residues 4-5, which as an individual sequence fragment redundantly maps to IL-2, IL-15 and IL-9. Similarly, residue 7 as an individual sequence fragment redundantly maps to IL-15 and IL-9. BNZ gamma further comprises an individual sequence fragment at position 9 which uniquely maps to IL-2 at position 9. BNZ gamma further comprises an individual sequence fragment at positions 10-13 which uniquely maps to IL-15 at positions 10-13. The sequence fragment also comprises residue 13, which as an individual sequence fragment redundantly maps to IL-2, IL-15 and IL-9. BNZ gamma further comprises an individual sequence fragment at positions 13-16 which uniquely maps to homologous positions 13-16 of IL-2. BNZ gamma further comprises an individual sequence fragment at positions 16-19, overlapping with the previous sequence fragment at position 16 and uniquely mapping to positions 16-19 of IL-15.

Thus, referring to BNZ gamma one may observe both specific details and general characteristics of the method disclosed herein. For example, target polypeptides are not necessarily equally represented in the sequence fragments which comprise an inhibitor polypeptide. 16 of 19 listed BNZ gamma residues map to three sequence fragments of IL-15, 8 of 19 residues map to three sequence fragments of IL-2, and 4 of 19 residues map to three sequence fragments of IL-9. None of the sequence fragments that map to IL-9 are unique to IL-9. Nonetheless BNZ gamma demonstrates inhibitory activity against all of IL-2, IL-15 and IL-9. Notably, a number of sequence fragments could also be mapped to at least one of IL-4, IL-7 and IL-21. For example, residues at positions 4-5 are absolutely conserved within the family, and sequence fragments of 1-2 residues may easily be identified that redundantly map to one or more non-target polypeptides. However, BNZ gamma does not exhibit inhibitory activity against ligand-receptor interactions involving these proteins.

The IL-17 cytokine family compromises six cytokines IL-17A, IL-17B, IL-17C, IL-17D, IL-17E (IL-25), and IL-17F. These are pro-inflammatory cytokines that contribute to the pathogenesis of several inflammatory diseases. A major source of IL-17 is a linage of T cells known as T helper (Th)-17 cells which are distinct from Th-1 and Th-2 cells. The IL-17 cytokine family belongs to the Cystine-Knot cytokine family and its members are the topic of intense research. It is believed that they share one common receptor, namely IL-17RA. Using steps of the methods as disclosed herein, one may identify amino acids that are predicted to be critical in receptor binding.

Target region sequences of IL-17 family members and of inhibitory polypeptide BNZ17-1 are shown in Table 7.

TABLE 7

| Residue | 1 2 3 4 5 6 7 8 9 10 | 11 | 12 | 13 | 14 | 15 | 16 | 17 | 18 | 19 | 20 | 21 | 22 | 23 | 24 | 25 | 26 | 27 | 28 |
|---|---|---|---|---|---|---|---|---|---|---|---|---|---|---|---|---|---|---|---|
| IL-17A (SEQ ID NO: 142) | Y N R S T S P W N L | H | R | N | E | D | P | E | R | Y | P | S | V | I | W | E | A | K | C |
| IL-17F (SEQ ID NO: 143) | N S R - I S P W R Y | E | L | D | R | D | L | N | R | L | P | Q | D | L | Y | H | A | R | C |
| BNZ17-1 (SEQ ID NO: 144) | Y S R S T S P W R Y | H | R | D | R | D | P | N | R | Y | P | S | D | L | Y | H | A | K | C |
| IL17B (SEQ ID NO: 145) | N K R S L S P W G Y | S | I | N | H | D | P | S | R | I | P | V | D | L | P | E | A | R | C |
| IL-17C (SEQ ID NO: 146) | H Q R S I S P W R Y | R | V | D | T | D | E | D | R | Y | P | Q | K | L | A | F | A | E | C |

TABLE 7-continued

| Residue | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 |
|---|---|---|---|---|---|---|---|---|---|---|---|---|---|---|---|---|---|---|---|---|---|---|---|---|---|---|---|---|
| IL17D (SEQ ID NO: 147) | N | L | R | S | V | S | P | W | A | Y | R | I | S | Y | D | P | A | R | Y | P | R | Y | L | P | E | A | Y | C |
| IL-17E (IL25) (SEQ ID NO: 148) | N | S | R | - | I | S | P | W | R | Y | E | L | D | R | D | L | N | R | L | P | Q | D | L | Y | H | A | R | C |

The target regions identified for IL-17 family members are substantially more similar to one another than are those of IL-6 or gamma-c family members. In particular, residues at 11 positions in the target region are absolutely conserved across all family members. Nonetheless, BNZ17-1 specifically inhibits IL-17A and IL-17F to the exclusion of the remaining family members.

The polypeptide BNZ17-1 comprises a sequence fragment comprising residues 1-8, which uniquely maps to residues 1-8 of IL-17A. Residues 3 and 6-8 are also universally conserved in the family. Overlapping with this fragment is a unique sequence fragment spanning residues 6-10 of BNZ17-1, comprising residues 5-9 of IL-17F, three of which are the absolutely conserved residues mentioned above. The polypeptide BNZ17-1 also comprises a sequence fragment comprising residues 11-12, which uniquely maps to residues 11-12 of IL-17A. The polypeptide BNZ17-1 also comprises a sequence fragment comprising residues 13-15, which uniquely maps to residues 12-14 of IL-17F. The polypeptide BNZ17-1 also comprises a sequence fragment comprising residues 15-16, which uniquely maps to residues 15-16 of IL-17A, and which overlaps with the previous sequence fragment at a single residue. The polypeptide BNZ17-1 also comprises a sequence fragment comprising residues 17-18, which uniquely maps to residues 16-17 of IL-17F. The polypeptide BNZ17-1 also comprises a sequence fragment comprising residues 18-19, which uniquely maps to residues 18-19 of IL-17A. The polypeptide BNZ17-1 also comprises a sequence fragment comprising residues 20-21, which uniquely maps to residues 20-21 of IL-17A. The polypeptide BNZ17-1 also comprises a sequence fragment comprising residues 22-23, which uniquely maps to residues 20-21 of IL-17F. The polypeptide BNZ17-1 also comprises a sequence fragment comprising residues 23-24, which uniquely maps to residues 22-23 of IL-17A. The polypeptide BNZ17-1 also comprises a sequence fragment comprising residues 25-29, which uniquely maps to residues 23-27 of IL-17F. The polypeptide BNZ17-1 also comprises a sequence fragment comprising residues 29-31, which uniquely maps to residues 28-30 of IL-17A. Residues 29 and 31 are also universally conserved, and thus also map to IL-17F among other members of the family.

Referring to BNZ17-1, one may again observe both specific details and general characteristics of the method disclosed herein. Sequence fragments comprise unique sequences of each target polypeptide but also comprise residues at positions which are absolutely conserved among family members, even those not selectively targeted. Nonetheless, the polypeptide exhibits specific inhibition of IL-17A and IL-17F to the exclusion of other family members.

A substantial number of residues match those of off-target family members, both at universally conserved positions and at variable positions with respect to the target region alignment, but target specificity is not affected.

The sequence of an exemplary cross-family inhibitory polypeptide comprises IKEFLQSFIHIVQSIINTSLTH-LIERSSRAVLQSLLRASRQ (SEQ ID NO: 149). The polypeptide comprises the BNZ gamma molecule discussed, above, to which is fused at its carboxy-terminus the BNZ130-1 molecule. The product is a cross-family inhibitory polypeptide that specifically inhibits each of IL-2, IL-15 and IL-9, and also specifically inhibits all of IL-6 and IL-27 without inhibiting other members of either family.

As demonstrated above and disclosed generally, two single family polypeptide inhibitors may be covalently tethered by an intervening linker sequence to form a cross family polypeptide inhibitor having the specificity of each of its single family polypeptide inhibitors.

The sequence of an exemplary cross-family inhibitory polypeptide comprises IKEFLQSFIHIVQSIINT-SASASASASASASALTHLIERSSRAVLQSLLRASRQ (SEQ ID NO: 150). The polypeptide comprises the BNZ gamma molecule, above, to which is fused at its N-terminus or carboxy-terminus or side chain a polypeptide linker comprising the sequence ASASASASASASA (SEQ ID NO: 151), to which is fused at its carboxy-terminus or N-terminus or side-chain the BNZ130-1 molecule. The product is a cross-family inhibitory polypeptide that specifically inhibits each of IL-2, IL-15 and IL-9, and also specifically inhibits IL-6 and IL-27. The polypeptide linker is unstructured and hydrophilic, so as to not interfere with solubility of the cross-family inhibitory polypeptide or with the ability of either of the BNZ gamma constituent or the BNZ130-1 constituent to affect its respective targets. Other polypeptide linker sequences are contemplated. The linker can be amino-acid or synthetic materials such as PEG, for example a bi-functional PEG molecule linker. The polypeptide linker maybe designed so it will be cleaved off in vivo to release the two peptides to act independently.

As demonstrated above and disclosed generally, two single family polypeptide inhibitors may be covalently tethered by an intervening linker sequence to form a cross family polypeptide inhibitor having the specificity of each of its single family polypeptide inhibitors.

As another example illustrative of both specific details and general aspects of the compositions and methods disclosed herein, one may review a cross-family inhibitory polypeptide generated to target specific members of the gamma-c cytokine family, the IL-6 cytokine family and the IL-17 cytokine family. In particular, one may review a specific inhibitor of gamma-c cytokines IL-2, IL-15 and IL-9; IL-6 family cytokines IL-6 and IL-27; and IL-17 family members IL-17A and IL-17F.

The sequence of an exemplary cross-family inhibitory polypeptide comprises IKEFLQSFIHIVQSIINT-SASASASASASASALTHLIERSSRAVLQSLLRAS-RQASASASASAS ASAYSRSTSPWRYHRDRDPN-RYLPSDLYHAKC (SEQ ID NO: 152). The polypeptide comprises the BNZ gamma molecule, above, to which is fused at its carboxy-terminus a polypeptide linker comprising the sequence ASASASASASASA (SEQ ID NO: 151), to which is fused at its carboxy-terminus the BNZ130-1 molecule, to which is fused at its carboxy-terminus a polypeptide linker comprising the sequence ASASASASASASA (SEQ ID NO: 151), to which is fused at its carboxy-terminus a polypeptide linker comprising the sequence of BNZ17-1. In some embodiments the lin Pesu M, Candotti F, Husa M, Hofmann S R, Notarangelo L D, and O'Shea J J. Jak3, severe combined immunodeficiency, and a new class of immunosuppressive drugs. 2005 Immunol. Rev. 203:127-142.

Pesu, M., Laurence, A., Kishore, N., Zwillich, S., Chan, G., O'Shea, J. J., Therapeutic targeting of Janus kinases. Immunol. 2008 Rev. 223:132-142.

Rochman, Y., Spolski, R., Leonard, W. J., New Insights into the regulation of T cells by gamma c family cytokines. 2009 Nat. Rev. Immunol. 9:480-90.

Sakaguchi, S., Yamaguchi, T., Nomura, T., Ono, M., Regulatory T cells and immune tolerance. 2008 Cell 133: 775-87.

Sato, N., Sabzevari, H., Fu, S., Ju, W., Bamford, R. N., Waldmann, T. A., and Tagaya, Y., Development of an IL-15-Autocrine CD8 T-cell Leukemia in IL-15 Transgenic mice requires the cis-expression of IL-15R alpha. Blood 2011 in press.

Sugamura, K., Asao, H., Kondo, M., Tanaka, N., Ishii, N., Nakamura, M., Takeshita, T., The common gamma-chain for multiple cytokine receptors. 1995 Adv. Immunol. 59: 225-277.

Sugamura, K., Asao, H., Kondo, M., Tanaka, N., Ishii, N., Ohbo, K., Nakamura, M., Takeshita, T., The interleukin-2 receptor gamma chain: its role in the multiple cytokine receptor complexes and T cell development in XSCID. 1996 Annu. Rev. Immunol. 14:179-205.

Tagaya, Y., Burton, J. D., Miyamoto, Y., Waldmann, T A., Identification of a novel receptor/signal transduction pathway for IL-15/T in mast cells. 1996 EMBO J. 15:4928-39.

Tagaya, Y., Memory CD8 T cells now join "Club 21". 2010 J. Leuk. Biol. 87:13-15.

Takai, K., Sawasaki, T., and Endo. Y. The Wheat-Germ Cell-Free Expression System, 2010 Curr. Pharm. Biotechnol. 11:272-8.

Tanaka, T., et al., A novel monoclonal antibody against murine IL-2 receptor beta-chain. Characterization of receptor expression in normal lymphoid cells and EL-4 cells. 1991 J. Immunol. 147:2222-28.

Takeshita, T., Asao, H., Ohtani, K., Ishii, N., Kumaki, S., Tanaka, N., Manukata, H., Nakamura, M., Sugamura, K., Cloning of the Gamma chain of the Human IL2 receptor. 1992 Science 257:379-382.

Waldmann, T. A., Anti-Tac (daclizumab, Zenapax) in the treatment of leukemia, autoimmune diseases, and in the prevention of allograft rejection: a 25-year personal odyssey. 2007 J. Clin. Immunol. 27: 1-18.

Enose-Akahata Y, Oh, U., Grant, C., Jacobson, S. Retrovirally induced CTL degranulation mediated by IL-15 expression and infection of mononuclear phagocytes in patients with HTLV-I-associated neurologic disease. Blood 112:2400-10 (2008).

Fukushima, N., Nishiura, Y., Nakamura, T., Kohno, S., Eguchi, K. Blockade of IL-2 receptor suppresses HTLV-I and IFN-gamma expression in patients with HTLV-I-associated myelopathy/tropical spastic paraparesis. Intern Med 46, 347-51 (2007).

Goon, P. K. et al. High circulating frequencies of tumor necrosis factor alpha- and interleukin-2-secreting human T-lymphotropic virus type 1 (HTLV-1)-specific CD4+ T cells in patients with HTLV-1-associated neurological disease. J Virol 77, 9716-22 (2003)

Santos, S. B. Et al. Modulation of T cell responses in HTLV-1 carriers and in patients with myelopathy associated with HTLV-1. Neuroimmunomodulation 13, 145-51 (2006)

Tendler, C. L. et al. Transactivation of interleukin 2 and its receptor induces immune activation in human T-cell lymphotropic virus type I-associated myelopathy: pathogenic implications and a rationale for immunotherapy. Proc Natl Acad Sci USA 87, 5218-22 (1990)

Araki, A. et al. Role of interleukin-21 isoform in dextran sulfate sodium (DSS)-induced colitis. Cytokine 62, 262-71 (2013)

Caruso R, Marafini I, Sedda S, Del Vecchio Blanco G, Giuffrida P, MacDonald T T, Corazza G R, Pallone F, Di Sabatino A, Monteleone G. Analysis of the cytokine profile in the duodenal mucosa of refractory coeliac disease patients. Clin Sci 126, 451-8 (2014)

DePaolo, R. W. et al. Co-adjuvant effects of retinoic acid and IL-15 induce inflammatory immunity to dietary antigens. Nature 471, 220-4 (2011).

Festen, E. A. et al. Genetic variants in the region harbouring IL2/IL21 associated with ulcerative colitis. Gut 58, 799-804 (2009).

Maiuri, L. et al. IL-15 drives the specific migration of CD94+ and TCR-γδ+ intraepithelial lymphocytes in organ cultures of treated celiac patients. Am J Gastroenterol 96, 150-6 (2001)

Meresse, B. et al. Coordinated induction by IL15 of a TCR-independent NKG2D signaling pathway converts CTL into lymphokine-activated killer cells in celiac disease. Immunity 21:357-66 (2004)

Amadi-Obi, A. et al. TH17 cells contribute to uveitis and scleritis and are expanded by IL-2 and inhibited by IL-27/STAT1. Nat Med 13, 711-8 (2007).

Wang, L. et al. Key role for IL-21 in experimental autoimmune uveitis. Proc Natl Acad Sci USA 108, 9542-7 (2011).

Yeh, S. et al. High-dose humanized anti-IL-2 receptor alpha antibody (daclizumab) for the treatment of active, non-infectious uveitis. J Autoimmun 31:91-7 (2008)

Akbari, et al. Essential role of NKT cells producing IL-4 and IL-13 in the development of allergen-induced airway hyperreactivity. Nat Med 9, 582-8 (2003).

Antoniu. S. A. MEDI-528, an anti-IL-9 humanized antibody for the treatment of asthma. Curr Opin Mol Ther 12, 233-9 (2010)

Beghè, B. et al. Polymorphisms in the interleukin-4 and interleukin-4 receptor alpha chain genes confer susceptibility to asthma and atopy in a Caucasian population. Clin Exp Allergy 33, 1111-7 (2003).

Chen, W. IL-13 receptor α2 contributes to development of experimental allergic asthma. J Allergy Clin Immunol 132, 951-8 (2013)

Cheng, G. Anti-interleukin-9 antibody treatment inhibits airway inflammation and hyperreactivity in mouse asthma model. Am J Respir Crit Care Med 166:409-16 (2002).

Daneshmandi, S., Pourfathollah, A. A., Pourpak, Z., Heidarnazhad, H., Kalvanagh, P. A. Cytokine gene polymorphism and asthma susceptibility, progress and control level. Mol Biol Rep 39, 1845-53 (2012).

Kasaian, M. T. et al. An IL-4/IL-13 dual antagonist reduces lung inflammation, airway hyperresponsiveness, and IgE production in mice. Am J Respir Cell Mol Biol 49, 37-46 (2013)

Nicolaides, N. C. et al. Interleukin 9: a candidate gene for asthma. Proc Natl Acad Sci USA 94, 13175-80 (1994).

Oh, C. K., Leigh, R., McLaurin, K. K., Kim, K., Hultquist, M., Molfino, N. A. A randomized, controlled trial to evaluate the effect of an anti-interleukin-9 monoclonal antibody in adults with uncontrolled asthma. Respir Res 14:93 (2013)

Schmidt-Weber, C. B. Anti-IL-4 as a new strategy in allergy. *Chem Immunol Allergy* 96:120-5 (2012)

Spiess, C. et al. Development of a human IgG4 bispecific antibody for dual targeting of interleukin-4 (IL-4) and interleukin-13 (IL-13) cytokines. *J Biol Chem* 288, 26583-93 (2013).

Walsh, G. M. Therapeutic potential of targeting interleukin 5 in asthma. *BioDrug* 27:559-63 (2013)

Wechsler, M. E. Inhibiting interleukin-4 and interleukin-13 in difficult-to-control asthma. *N Engl J Med* 368, 2511-3 (2013)

Cavanillas, M. L. et al. Polymorphisms in the IL2, IL2RA and IL2RB genes in multiple sclerosis risk. *Eur J Hum Genet* 18, 794-9 (2010)

Forte, G. I. et al. Search for genetic factors associated with susceptibility to multiple sclerosis. *Ann N Y Acad Sci* 1067, 264-9 (2006)

Li, H., Nourbakhsh, B., Ciric, B., Zhang, G. X., & Rostami, A. Neutralization of IL-9 ameliorates experimental autoimmune encephalomyelitis by decreasing the effector T cell population. *J Immunol* 185, 4095-100 (2010).

Martin, R. Humanized anti-CD25 antibody treatment with daclizumab in multiple sclerosis. *Neurodegener Dis* 5, 23-6 (2008).

Nowak, E. C. et al. IL-9 as a mediator of Th17-driven inflammatory disease. J Exp Med 206, 1653-60 (2009)

Petitto, J. M., Streit, W. J., Huang, Z., Butfiloski, E., & Schiffenbauer, J. Interleukin-2 gene deletion produces a robust reduction in susceptibility to experimental autoimmune encephalomyelitis in C57BL/6 mice. *Neurosci Lett* 285, 66-70 (2000).

Saikali, P., Antel, J. P., Pittet, C. L., Newcombe, J., Arbour, N. Contribution of astrocyte-derived IL15 to CD8 T cell effector functions in multiple sclerosis. *J Immunol.* 185, 5693-703 (2010).

Schneider, R. et al. B cell-derived IL-15 enhances CD8 T cell cytotoxicity and is increased in multiple sclerosis patients. *J Immunol* 187, 4119-28 (2011).

Baslund, B. et al. Targeting interleukin-15 in patients with rheumatoid arthritis: a proof-of-concept study. *Arthritis Rheum* 52, 2686-92 (2005).

Daha, N. A. et al. Confirmation of STAT4, IL2/IL21, and CTLA4 polymorphisms in rheumatoid arthritis. *Arthritis Rheum* 60, 1255-60 (2009).

De Benedetti, F. et al. Randomized trial of tocilizumab in systemic juvenile idiopathic arthritis. *N Engl J Med* 367, 2385-95 (2012)

Hartgring, S. A., Bijlsma, J. W., Lafeber, F. P., van Roon, J. A. Interleukin-7 induced immunopathology in arthritis. *Ann Rheum Dis* 65 Suppl 3:iii69-74 (2006)

Hartgring, S. A. et al. Elevated expression of interleukin-7 receptor in inflamed joints mediates interleukin-7-induced immune activation in rheumatoid arthritis. *Arthritis Rheum.* 60, 2595-605 (2009)

Kishimoto T. IL-6: from its discovery to clinical applications. *Int Immunol* 22, 347-52 (2010) Liu, R. et al. A regulatory effect of IL-21 on T follicular helper-like cell and B cell in rheumatoid arthritis. *Arthritis Res Ther* 14, R255 (2012).

Pickens, S. R. et al. Characterization of interleukin-7 and interleukin-7 receptor in the pathogenesis of rheumatoid arthritis. *Arthritis Rheum.* 63, 2884-93 (2011).

Waldmann, T. A. The biology of IL-15: implications for cancer therapy and the treatment of autoimmune disorders. *J Investig Dermatol Symp Proc* 16, S28-30 (2013)

Young, D. A. et al. Blockade of the interleukin-21/interleukin-21 receptor pathway ameliorates disease in animal models of rheumatoid arthritis. *Arthritis Rheum.* 56, 1152-63 (2007).

Notredame, C., Higgins, D. G, Heringa, J. T-Coffee: A novel method for fast and accurate multiple sequence alignment. *J Mol Biol.* 302, 205-17 (2000).

Wang, X., Rickert, M., Garcia, K. C. Structure of the quaternary complex of interleukin-2 with its alpha, beta, and gamma c receptors. *Science* 310, 1159-63 (2005).

Ring, A. M. et al. Mechanistic and structural insight into the functional dichotomy between IL-2 and IL-15. *Nat Immunol* 13, 1187-95 (2012).

LaPorte, S. L. et al. Molecular and structural basis of cytokine receptor pleiotropy in the interleukin-4/13 system. *Cell* 132, 259-72 (2008)

Vanderhoek, J. Y., Tare, N. S., Bailey, J. M., Goldstein, A. L., Pluznik, D. H. New role for 15-hydroxyeicosatetraenoic acid. Activator of leukotriene biosynthesis in PT-18 mast/basophil cells. *J Biol Chem* 257, 12191-5 (1982).

Hu-Li J, Ohara J, Watson C, Tsang W, Paul W E. Derivation of a T cell line that is highly responsive to IL-4 and IL-2 (CT.4R) and of an IL-2 hyporesponsive mutant of that line (CT.4S). *J Immunol* 142, 800-7 (1989)

Thévenet, P., Shen, Y., Maupetit, J., Guyon, F., Derreumaux, P. & Tufféry, P. PEP-FOLD: an updated de novo structure prediction server for both linear and disulfide bonded cyclic peptides. *Nucleic Acids Res* 40, W288-293 (2012)

Maupetit, J., Derreumaux. P., Tufféry, P. PEP-FOLD: an online resource for de novo peptide structure prediction. *Nucleic Acids Res* 37 (Web Server issue), W498-503 (2009)

Maupetit, J., Derreumaux, P., Tuffery. P. *A fast and accurate method for large-scale de novo peptide structure prediction.* J Comput Chem 31, 726-38 (2010).

Duhovny, D., Nussinov, R., & Wolfson, H. J. Efficient Unbound Docking of Rigid Molecules. In Gusfield et al., Ed. Proceedings of the 2'nd Workshop on Algorithms in Bioinformatics (WABI) Rome, Italy, Lecture Notes in Computer Science 2452, pp. 185-200, (Springer, New York 2002)

Schneidman-Duhovny, D. et al. Taking geometry to its edge: fast unbound rigid (and hinge-bent) docking. *Proteins* 52, 107-12 (2003)

Schneidman-Duhovny, D., Inbar, Y., Nussinov, R., & Wolfson, H. J. PatchDock and SymmDock: servers for rigid and symmetric docking. *Nucl. Acids. Res* 33, W363-367 (2005)

Zhang, C., Vasmatzis, G., Cornette, J. L. & DeLisi, C. Determination of atomic desolvation energies from the structures of crystallized proteins. *J Mol Biol* 267, 707-726 (1997)

Kingsford, C. L., Chazelle, B. & Singh M. Solving and analyzing side-chain positioning problems using linear and integer programming. *Bioinformatics,* 21, 1028-1036

LaPorte, S. L. et al. Molecular and structural basis of cytokine receptor pleiotropy in the interleukin-4/13 system. *Cell* 132, 259-72 (2008)

Vanderhoek, J. Y., Tare, N. S., Bailey, J. M., Goldstein, A. L., Pluznik, D. H. New role for 15-hydroxyeicosatetraenoic acid. Activator of leukotriene biosynthesis in PT-18 mast/basophil cells. *J Biol Chem* 257, 12191-5 (1982).

Andrusier, N., Nussinov, R., & Wolfson, H. J. FireDock: Fast Interaction Refinement in Molecular Docking. *Proteins* 69, 139-59 (2007)

What is claimed is:

1. A therapeutic composite peptide conjugate, wherein the therapeutic composite peptide conjugate inhibits an activity of at least two cytokines selected from a family of cytokines that bind to a common receptor, wherein the therapeutic composite peptide conjugate comprises a therapeutic composite peptide conjugated to a moiety;
wherein the therapeutic peptide conjugate is 11-50 amino acids in length;
wherein the therapeutic peptide comprises a region 1-20 amino acids in length that aligns with a corresponding region of a single target ligand or receptor; and
wherein the single target ligand or receptor is of any one of SEQ ID NO:122, SEQ ID NO:123, SEQ ID NO:125, SEQ ID NO:126, SEQ ID NO:127, SEQ ID NO:128, SEQ ID NO:129, SEQ ID NO:142, SEQ ID NO:143, SEQ ID NO:145, SEQ ID NO:146, SEQ ID NO:147, SEQ ID NO:148, SEQ ID NO:155, SEQ ID NO:156, SEQ ID NO:158, SEQ ID NO:159, SEQ ID NO:160, and SEQ ID NO:161.

2. The therapeutic composite peptide conjugate of claim 1, wherein the moiety is a selected from the group consisting of a biological protein, BSA, albumin, immunoglobulin, antibody fragment, Fc region of IgG, a scaffold protein, carbohydrate, and polyethylene glycol.

3. The therapeutic composite peptide conjugate of claim 2, wherein the therapeutic composite peptide is conjugated to an N-terminus, C-terminus and/or a side residue of the moiety.

4. The therapeutic composite peptide conjugate of claim 1, wherein the moiety enables efficient delivery and improved biological stability therapeutic composite peptide conjugate in vivo.

5. The therapeutic composite peptide conjugate of claim 1, wherein the family of cytokines is selected from the group consisting of γc-family of cytokines, IL-6 family of cytokines, and IL-17 family of cytokines.

6. The therapeutic composite peptide conjugate of claim 5, wherein the γc-family of cytokines consists of IL-2, IL-4, IL-7, IL-9, IL-15, and IL-21, the IL-6 family of cytokines consists of IL-6, IL-11, CNTF, CT-1, OSM, LIF, and IL-27, and the IL-17 family of cytokines consists of IL-17A, IL-17B, IL-17C, IL-17D, IL-17E (IL-25), and IL-17F.

7. The therapeutic composite peptide conjugate of claim 1, wherein the therapeutic composite peptide conjugate is used to ameliorate and/or treat a disease selected from the group consisting of a γc-cytokine-mediated disease, an HTLV-1-associated myelopathy (HAM)/tropical spastic paraparesis (TSP) associated disease, and an inflammatory respiratory disease.

8. The therapeutic composite peptide conjugate of claim 7, wherein the γc-cytokine-mediated disease is selected from the group consisting of CD4-leukemia, CD8-leukemia, LGL-leukemia, systemic lupus erythematosus, Sjögren's syndrome, Wegener's granulomatosis, Celiac disease, Hashimoto's thyroiditis, rheumatoid arthritis, inflammatory bowel disease, diabetes mellitus, psoriasis, multiple sclerosis, uveitis, inflammation of the eye, and graft-versus-host disease (GvHD).

9. The therapeutic composite peptide conjugate of claim 7, wherein the HAM/TSP associated disease is selected from the group consisting of Adult T-cell Leukemia (ATL), HTLV-associated Myelopathy/Tropical Spastic Paraparesis (HAM/TSP), and other non-neoplastic inflammatory diseases associated with HTLV.

10. The therapeutic composite peptide conjugate of claim 7, wherein the inflammatory respiratory disease is selected from the group consisting of asthma, sinusitis, hay fever, bronchitis, chronic obstructive pulmonary disease (COPD), allergic rhinitis, acute and chronic otitis, and lung fibrosis.

11. The therapeutic composite peptide conjugate of claim 1, wherein the therapeutic composite peptide conjugate is used for a cosmetic purpose.

12. The therapeutic composite peptide conjugate of claim 11, wherein the cosmetic purpose is selected from the group consisting of treatment of acne, treatment of hair loss, treatment of sunburn, nail maintenance, and reduction in the appearance of aging.

* * * * *